United States Patent
Permuth et al.

(10) Patent No.: US 12,215,388 B2
(45) Date of Patent: *Feb. 4, 2025

(54) THERANOSTIC TOOLS FOR MANAGEMENT OF PANCREATIC CANCER AND ITS PRECURSORS

(71) Applicant: H. LEE MOFFITT CANCER CENTER AND RESEARCH INSTITUTE, INC., Tampa, FL (US)

(72) Inventors: Jennifer Permuth, Tampa, FL (US); Daniel Jeong, Tampa, FL (US); Jung Choi, Wesley Chapel, FL (US); Yoganand Balagurunathan, Tampa, FL (US); Dung-Tsa Chen, Tampa, FL (US); Mokenge Malafa, Tampa, FL (US)

(73) Assignee: Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/610,001

(22) PCT Filed: May 3, 2018

(86) PCT No.: PCT/US2018/030994
§ 371 (c)(1),
(2) Date: Oct. 31, 2019

(87) PCT Pub. No.: WO2018/204725
PCT Pub. Date: Nov. 8, 2018

(65) Prior Publication Data
US 2020/0063215 A1 Feb. 27, 2020

Related U.S. Application Data

(60) Provisional application No. 62/501,040, filed on May 3, 2017.

(51) Int. Cl.
C12Q 1/6886 (2018.01)

(52) U.S. Cl.
CPC ...... *C12Q 1/6886* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 7,919,237 B2 | 4/2011 | Dimitrov et al. |
| 8,415,102 B2 | 4/2013 | Geiss et al. |
| 8,519,115 B2 | 8/2013 | Webster et al. |
| 10,240,208 B2 | 3/2019 | Malafa et al. |
| 2013/0324589 A1 | 12/2013 | Croce et al. |
| 2017/0022571 A1 | 1/2017 | Malafa et al. |

FOREIGN PATENT DOCUMENTS

WO WO 2015/153679 * 10/2015

OTHER PUBLICATIONS

Lambin (European Journal of Cancer (2012) 48 pp. 441-446).*
Pritchard (Nature Reviews Genetics vol. May 13, 2012 pp. 358-369).*
Permuth (Proceedings: AACR 107th Annual Meeting 2016; Apr. 16-20, 2016; New Orleans, LA).*
Permuth (Oncotarget Aug. 31, 2016 vol. 7 No. 52 pp. 85785-85797).*
Hanania (Oncotarget Aug. 31, 2016 vol. 7 No. 52 pp. 85776-85784).*
Springer (Gastroenterology 2015 vol. 149 pp. 1501-1510).*
Permuth (Poster 970A/27 titled Using a Radiogenomic Approach to Classify Pancreatic Cancer Precursors presented at AACR 107th Annual Meeting 2016; Apr. 16-20, 2016; New Orleans, LA).*
Abdalla, M. et al., "Effect of RNA Isolation Method on microRNA Quantity and Quality in Plasma: A Comparative Study," Norgen Biotek Corporation Application Note 49: RNA Sample Preparation, 2011, pp. 1-4.
Bergmann, U. et al., "Increased expression of insulin receptor substrate-1 in human pancreatic cancer," *Biochem. Biophys. Res. Commun.*, 1996, vol. 220, No. 3, pp. 886-890, abstract.
Blondal, T. et al., "Assessing sample and miRNA profile quality in serum and plasma or other biofluids," *Methods*, 2013, vol. 59, No. 1, pp. S1-S6.
Canto, M.I. et al., "International Cancer of the Pancreas Screening (CAPS) Consortium summit on the management of patients with increased risk for familial pancreatic cancer," *Gut*, 2013, vol. 62, No. 3, pp. 339-347.
Chen, D.T. et al., "Prognostic and predictive value of a malignancy-risk gene signature in early-stage non-small cell lung cancer," *J. Natl. Cancer Inst.*, 2011, vol. 103, No. 24, pp. 1859-1870.
Chen, D.T. et al., "Proliferative genes dominate malignancy-risk gene signature in histologically-normal breast tissue," *Breast Cancer Res. Treat.*, 2010, vol. 119, No. 2, pp. 335-346.
Chiyomaru, T. et al., "Genistein up-regulates tumor suppressor microRNA-574-3p in prostate cancer," *PLOS One*, 2013, vol. 8, No. 3, e58929.
Farina, N.H. et al., "Standardizing analysis of circulating microRNA: clinical and biological relevance," *J. Cell. Biochem.*, 2014, vol. 115, No. 5, pp. 805-811.
Fourie, N.H. et al., "Elevated circulating miR-150 and miR-342-3p in patients with irritable bowel syndrome," *Exp. Mol. Pathol.*, 2014, vol. 96, No. 3, pp. 422-425.

(Continued)

*Primary Examiner* — Amanda Haney
(74) *Attorney, Agent, or Firm* — Meunier Carlin & Curfman LLC

(57) ABSTRACT

The present invention concerns materials and methods for identifying and classifying pancreatic ductal adenocarcinoma (PDAC) precursors or intraductal papillary mucinous neoplasm (IPMN) using messenger RNAs, microRNAs, long non-coding RNAs, radiomic features, radiologic measures of abdominal/visceral obesity, and combinations thereof, as diagnostic markers for integration with clinical management and interventions for personalized care.

15 Claims, 11 Drawing Sheets

Specification includes a Sequence Listing.

(56) References Cited

OTHER PUBLICATIONS

Frampton, A.E. et al., "Loss of miR-126 is crucial to pancreatic cancer progression," *Expert Rev. Anticancer Ther.*, 2012, vol. 12, No. 7, pp. 881-884, abstract.
Ganepola, G.A. et al., "Novel blood-based microRNA biomarker panel for early diagnosis of pancreatic cancer," *World J. Gastrointestinal Onco.*, 2014, vol. 6, pp. 22-33.
Gao, L. et al., "miR-335 functions as a tumor suppressor in pancreatic cancer by targeting OCT4," *Tumour Biology*, 2014, vol. 35, No. 8, pp. 8309-8318, abstract.
Geiss, G.K. et al., "Direct multiplexed measurement of gene expression with color-coded probe pairs," *Nat. Biotechnol.*, 2008, vol. 26, No. 3, pp. 317-325, abstract.
Greenbaum, D. et al., "Comparing protein abundance and mRNA expression levels on a genomic scale," *Genome Biol.*, 2003, vol. 4, No. 9, p. 117.
Henry, J.C. et al., "MicroRNA from Pancreatic Duct Aspirate Differentiates Cystic Lesions of the Pancreas," *Ann. Surg. Oncol.*, 2013, vol. 20, No. Suppl. 3, pp. S661-S666, abstract.
Hirata, H. et al., "Genistein downregulates onco-miR-1260b and upregulates sFRP1 and Smad4 via demethylation and histone modification in prostate cancer cells," *Br. J. Cancer*, 2014, vol. 110, No. 6, pp. 1645-1654.
Hruban, R.H. et al., "Precursors to pancreatic cancer," *Gastroenterol. Clin. North. Am.*, 2007, vol. 36, No. 4, pp. 831-849.
Hu, J. et al., "Human miR-1228 as a stable endogenous control for the quantification of circulating microRNAs in cancer patients," *Int. J. Cancer*, 2014, vol. 135, No. 5, pp. 1187-1194.
Jiao, L.R. et al., "MicroRNAs targeting oncogenes are downregulated in pancreatic malignant transformation from benign tumors," *PLOS One*, 2012, vol. 7, No. 2, e32068.
Kapoor, S., "miR-145 and its influence on tumor growth in systemic malignancies," *Eur. J. Cancer Prev.*, 2014, vol. 23, No. 3, p. 233, abstract.
Kirschner, M.B. et al., "The Impact of Hemolysis on Cell-Free microRNA Biomarkers," *Front Genet.*, 2013, vol. 4, Article 94, pp. 1-13.
Lee, L.S. et al. "Investigating microRNA expression profiles in pancreatic cystic neoplasms," *Clinical and Translational Gastroenterology*, 2014, vol. 5, e47, pp. 1-6.
Li, A. et al., "Pancreatic cancers epigenetically silence SIP1 and hypomethylate and overexpress miR-200a/200b in association with elevated circulating miR-200a and miR-200b levels," *Cancer Res.*, 2010, vol. 70, No. 13, pp. 5226-5237.
Li, A. et al., "MicroRNA Array Analysis Finds Elevated Serum miR-1290 Accurately Distinguishes Patients with Low-Stage Pancreatic Cancer from Healthy and Disease Controls," *Clin. Cancer Res.*, 2013, vol. 19, No. 13, pp. 3600-3610.
Li, B.H. et al., "Reduced miR-100 expression in cervical cancer and precursors and its carcinogenic effect through targeting PLK1 protein," *Eur. J. Cancer*, 2011, vol. 47, No. 14, pp. 2166-2174, abstract.
Liu, J. et al., "MicroRNA-100 is a potential molecular marker of non-small cell lung cancer and functions as a tumor suppressor by targeting polo-like kinase 1," *BMC Cancer*, 2012, vol. 12, p. 519.
Liu, R. et al., "Serum microRNA expression profile as a biomarker in the diagnosis and prognosis of pancreatic cancer," *Clin. Chem.*, 2012, vol. 58, No. 3, pp. 610-618.
Lubezky, N. et al., "MicroRNA expression signatures in intraductal papillary mucinous neoplasm of the pancreas," *Surgery*, 2013, vol. 153, pp. 663-672.
Matthaei, H. et al., "miRNA biomarkers in cyst fluid augment the diagnosis and management of pancreatic cysts," *Clin. Cancer Res.*, 2012, vol. 18, No. 17, pp. 4713-4724.
Mitchell, P.S. et al., "Circulating microRNAs as stable blood-based markers for cancer detection," *Proc. Natl. Acad. Sci. USA*, 2008, vol. 105, No. 30, pp. 10513-10518.
Nissim, S. et al., "Genetic markers of malignant transformation in intraductal papillary mucinous neoplasm of the pancreas: a meta-analysis," *Pancreas*, 2012, vol. 41, No. 8, pp. 1195-1205.

Permuth-Wey, J. et al., "A genome-wide investigation of microRNA expression identifies biologically-meaningful microRNAs that distinguish between high-risk and low-risk intraductal papillary mucinous neoplasms of the pancreas," *PLOS One*, 2015, vol. 10, No. 1, e0116869.
Permuth-Wey, J. et al., "Tackling a clinical challenge: Using microRNAs to differentiate between low-and high-risk Pancreatic Cysts," *Cancer Res*, 2013, vol. 73, No. 8 Suppl., Abstract No. LB-70.
Permuth-Wey, J. et al., "Tackling a clinical challenge: Using microRNAs to differentiate between low-and high-risk Pancreatic Cysts," poster presented at Proceedings of the 104th Annual Meeting of the American Association for Cancer Research, Apr. 6-10, 2013, Washington, D.C.
Pritchard, C.C. et al., "Blood cell origin of circulating microRNAs: a cautionary note for cancer biomarker studies," *Cancer Prev. Res. (Phila.)*, 2012, vol. 5, No. 3, pp. 492-497.
Sachs, T. et al., "The incidental asymptomatic pancreatic lesion: nuisance or threat?," *J. Gastrointest. Surg.*, 2009, vol. 13, No. 3, pp. 405-415, abstract.
Schultz, N.A. et al., "MicroRNA biomarkers in whole blood for detection of pancreatic cancer," *JAMA*, 2014, vol. 311, No. 4, pp. 392-404, abstract.
Su, Y. et al., "Aberrant expression of microRNAs in gastric cancer and biological significance of miR-574-3p," *International Immunopharmacology*, 2012, vol. 13, No. 4, pp. 468-475.
Sun, D. et al., "miR-99 family of MicroRNAs suppresses the expression of prostate-specific antigen and prostate cancer cell proliferation," *Cancer Res.*, 2011, vol. 71, No. 4, pp. 1313-1324.
Suryawanshi, S. et al., "Plasma microRNAs as novel biomarkers for endometriosis and endometriosis-associated ovarian cancer," *Clin. Cancer Res.*, 2013, vol. 19, No. 5, pp. 1213-1224.
Tanaka, M. et al., "International consensus guidelines 2012 for the management of IPMN and MCN of the pancreas," *Pancreatology*, 2012, vol. 12, No. 3, pp. 183-197.
Tang, S. et al., "Sweating the small stuff: microRNAs and genetic changes define pancreatic cancer," *Pancreas*, 2013, vol. 42, No. 5, pp. 740-759.
Wang, H. et al., "MicroRNA-342 inhibits colorectal cancer cell proliferation and invasion by directly targeting DNA methyltransferase 1," *Carcinogenesis*, 2011, vol. 32, No. 7, pp. 1033-1042.
Wang, J. et al., "MicroRNAs in plasma of pancreatic ductal adenocarcinoma patients as novel blood-based biomarkers of disease," *Cancer Prev. Res. (Phila.)*, 2009, vol. 2, No. 9, pp. 807-813.
Weichert, W. et al., "Overexpression of Polo-like kinase 1 is a common and early event in pancreatic cancer," *Pancreatology*, 2005, vol. 5, Nos. 2-3, pp. 259-265, abstract.
Wu, J. et al., "Recurrent GNAS mutations define an unexpected pathway for pancreatic cyst development," *Sci. Transl. Med.*, 2011, vol. 3, No. 92, 92ra66.
Yachida, S. et al., "Distant metastasis occurs late during the genetic evolution of pancreatic cancer," *Nature*, 2010, vol. 467, No. 7319, pp. 1114-1117.
Zhang, D.X. et al., "Prognostic factors in patients with pancreatic cancer," *Exp. Ther. Med.*, 2012, vol. 3, No. 3, pp. 423-432.
Zhang, J.J. et al., "Association of increased DNA methyltransferase expression with carcinogenesis and poor prognosis in pancreatic ductal adenocarcinoma," *Clin. Transl. Oncol.*, 2012, vol. 14, No. 2, pp. 116-124.
Gagner, M. and Palermo, M. "Laparoscopic Whipple procedure: review of the literature" *J. Hepatobiliary Pancreatic Surgery*, 2009, vol. 16, pp. 726-730.
"Can Pancreatic Cancer Be Prevented?" Written by The American Cancer Society Medical and Editorial Content Team. 2016. Downloaded from www.cancer.org/cancer/pancreatic-cancer/causes-risksprevention/prevention.html on Jan. 10, 2018.
Fineberg, H. "The paradox of disease prevention celebrated in principle, resisted in practice" *JAMA*, 2013, vol. 310, No. 1, pp. 85-90.
Permuth et al. "A pilot study of radiologic measures of abdominal adiposity: weighty contributors to early pancreatic carcinogenesis worth evaluating?" *Cancer Biol. Med.*, 2017, 14(1):66-73.
Permuth, J.B. "A novel radiogenomic approach may improve prediction of malignant pathology in patients with intraductal papillary

(56) References Cited

OTHER PUBLICATIONS mucinous neoplasms of the pancreas" presented at AACR, 107$^{th}$ Annual Meeting, Apr. 16-20, 2016, New Orleans, LA.

Permuth, J.B. et al. "Using a Radiogenomic Approach to Classify Pancreatic Cancer Precursors" presented at AACR, 107$^{th}$ Annual Meeting, Apr. 16-20, 2016, New Orleans, LA.

* cited by examiner

SEQUENCE LISTING

```
<160> NUMBER OF SEQ ID NOS: 49

<210> SEQ ID NO 1
<211> LENGTH: 19
<212> TYPE: DNA
<213> ORGANISM: Artificial sequence
<220> FEATURE:
<223> OTHER INFORMATION: primer

<400> SEQUENCE: 1
tccagcaaat acacctggg                                                  19

<210> SEQ ID NO 2
<211> LENGTH: 17
<212> TYPE: DNA
<213> ORGANISM: Artificial sequence
<220> FEATURE:
<223> OTHER INFORMATION: primer

<400> SEQUENCE: 2
caggagccca gcctttg                                                    17

<210> SEQ ID NO 3
<211> LENGTH: 18
<212> TYPE: DNA
<213> ORGANISM: Artificial sequence
<220> FEATURE:
<223> OTHER INFORMATION: primer

<400> SEQUENCE: 3
gacgggtctg ttgttgcc                                                   18

<210> SEQ ID NO 4
<211> LENGTH: 18
<212> TYPE: DNA
<213> ORGANISM: Artificial sequence
<220> FEATURE:
<223> OTHER INFORMATION: primer

<400> SEQUENCE: 4
caggaccagg gctctttg                                                   18
```

```
<210> SEQ ID NO 5
<211> LENGTH: 20
<212> TYPE: DNA
<213> ORGANISM: Artificial sequence
<220> FEATURE:
<223> OTHER INFORMATION: primer

<400> SEQUENCE: 5
ggcctttctg ctgacaagtt                                              20

<210> SEQ ID NO 6
<211> LENGTH: 18
<212> TYPE: DNA
<213> ORGANISM: Artificial sequence
<220> FEATURE:
<223> OTHER INFORMATION: primer

<400> SEQUENCE: 6
tggcccagac tcttccag                                                18

<210> SEQ ID NO 7
<211> LENGTH: 18
<212> TYPE: DNA
<213> ORGANISM: Artificial sequence
<220> FEATURE:
<223> OTHER INFORMATION: primer

<400> SEQUENCE: 7
gcctgttgga catcctgg                                                18

<210> SEQ ID NO 8
<211> LENGTH: 18
<212> TYPE: DNA
<213> ORGANISM: Artificial sequence
<220> FEATURE:
<223> OTHER INFORMATION: primer

<400> SEQUENCE: 8
cttgttcccc accagcac                                                18

<210> SEQ ID NO 9
<211> LENGTH: 18
<212> TYPE: DNA
<213> ORGANISM: Artificial sequence
<220> FEATURE:
<223> OTHER INFORMATION: primer

<400> SEQUENCE: 9
aggcaccaca gaaagcca                                                18

<210> SEQ ID NO 10
<211> LENGTH: 18
<212> TYPE: DNA
<213> ORGANISM: Artificial sequence
<220> FEATURE:
<223> OTHER INFORMATION: primer

<400> SEQUENCE: 10
tgggagagtg aggtggga                                                18

<210> SEQ ID NO 11
<211> LENGTH: 18
<212> TYPE: DNA
<213> ORGANISM: Artificial sequence
<220> FEATURE:
<223> OTHER INFORMATION: primer
```

<400> SEQUENCE: 11
gggaacagcc aaagggat                                                 18

<210> SEQ ID NO 12
<211> LENGTH: 22
<212> TYPE: DNA
<213> ORGANISM: Artificial sequence
<220> FEATURE:
<223> OTHER INFORMATION: primer

<400> SEQUENCE: 12
ggcaaaatgt ctactctcca gg                                            22

<210> SEQ ID NO 13
<211> LENGTH: 18
<212> TYPE: DNA
<213> ORGANISM: Artificial sequence
<220> FEATURE:
<223> OTHER INFORMATION: primer

<400> SEQUENCE: 13
ggtctcaccc atgcaagc                                                 18

<210> SEQ ID NO 14
<211> LENGTH: 18
<212> TYPE: DNA
<213> ORGANISM: Artificial sequence
<220> FEATURE:
<223> OTHER INFORMATION: primer

<400> SEQUENCE: 14
cggcgggata aaccttct                                                 18

<210> SEQ ID NO 15
<211> LENGTH: 18
<212> TYPE: DNA
<213> ORGANISM: Artificial sequence
<220> FEATURE:
<223> OTHER INFORMATION: primer

<400> SEQUENCE: 15
tctcactgcc ttccctgc                                                 18

<210> SEQ ID NO 16
<211> LENGTH: 18
<212> TYPE: DNA
<213> ORGANISM: Artificial sequence
<220> FEATURE:
<223> OTHER INFORMATION: primer

<400> SEQUENCE: 16
agcacctcgt ctggctca                                                 18

<210> SEQ ID NO 17
<211> LENGTH: 18
<212> TYPE: DNA
<213> ORGANISM: Artificial sequence
<220> FEATURE:
<223> OTHER INFORMATION: primer

<400> SEQUENCE: 17
ctggaccaaa tatggggg                                                 18

<210> SEQ ID NO 18
<211> LENGTH: 19

```
<212> TYPE: DNA
<213> ORGANISM: Artificial sequence
<220> FEATURE:
<223> OTHER INFORMATION: primer

<400> SEQUENCE: 18
catgcatgag tatgctggc                                              19

<210> SEQ ID NO 19
<211> LENGTH: 18
<212> TYPE: DNA
<213> ORGANISM: Artificial sequence
<220> FEATURE:
<223> OTHER INFORMATION: primer

<400> SEQUENCE: 19
aaccgaaaat gcaccagc                                               18

<210> SEQ ID NO 20
<211> LENGTH: 18
<212> TYPE: DNA
<213> ORGANISM: Artificial sequence
<220> FEATURE:
<223> OTHER INFORMATION: primer

<400> SEQUENCE: 20
ctcctctgct tggacgga                                               18

<210> SEQ ID NO 21
<211> LENGTH: 20
<212> TYPE: DNA
<213> ORGANISM: Artificial sequence
<220> FEATURE:
<223> OTHER INFORMATION: primer

<400> SEQUENCE: 21
agttcaaaca catcaccccc                                             20

<210> SEQ ID NO 22
<211> LENGTH: 18
<212> TYPE: DNA
<213> ORGANISM: Artificial sequence
<220> FEATURE:
<223> OTHER INFORMATION: primer

<400> SEQUENCE: 22
ttcatcaagg aggccagc                                               18

<210> SEQ ID NO 23
<211> LENGTH: 18
<212> TYPE: DNA
<213> ORGANISM: Artificial sequence
<220> FEATURE:
<223> OTHER INFORMATION: primer

<400> SEQUENCE: 23
cgtagcctcc tccacgaa                                               18

<210> SEQ ID NO 24
<211> LENGTH: 18
<212> TYPE: DNA
<213> ORGANISM: Artificial sequence
<220> FEATURE:
<223> OTHER INFORMATION: primer

<400> SEQUENCE: 24
```

```
agtgggacag ttccagcg                                             18

<210> SEQ ID NO 25
<211> LENGTH: 19
<212> TYPE: DNA
<213> ORGANISM: Artificial sequence
<220> FEATURE:
<223> OTHER INFORMATION: primer

<400> SEQUENCE: 25
catggatgac ttgcttggg                                            19

<210> SEQ ID NO 26
<211> LENGTH: 18
<212> TYPE: DNA
<213> ORGANISM: Artificial sequence
<220> FEATURE:
<223> OTHER INFORMATION: primer

<400> SEQUENCE: 26
gggtgaggca agaccctt                                             18

<210> SEQ ID NO 27
<211> LENGTH: 18
<212> TYPE: DNA
<213> ORGANISM: Artificial sequence
<220> FEATURE:
<223> OTHER INFORMATION: primer

<400> SEQUENCE: 27
ggaagggatc tgctgggt                                             18

<210> SEQ ID NO 28
<211> LENGTH: 21
<212> TYPE: DNA
<213> ORGANISM: Artificial sequence
<220> FEATURE:
<223> OTHER INFORMATION: primer

<400> SEQUENCE: 28
tcaagggtga tacagtgcaa a                                         21

<210> SEQ ID NO 29
<211> LENGTH: 18
<212> TYPE: DNA
<213> ORGANISM: Artificial sequence
<220> FEATURE:
<223> OTHER INFORMATION: primer

<400> SEQUENCE: 29
atcttcctgc ccctgacc                                             18

<210> SEQ ID NO 30
<211> LENGTH: 21
<212> TYPE: DNA
<213> ORGANISM: Artificial sequence
<220> FEATURE:
<223> OTHER INFORMATION: primer

<400> SEQUENCE: 30
ttggaggtga aaattgtctg g                                         21

<210> SEQ ID NO 31
<211> LENGTH: 18
<212> TYPE: DNA
<213> ORGANISM: Artificial sequence
```

```
<220> FEATURE:
<223> OTHER INFORMATION: primer

<400> SEQUENCE: 31
gctcccctcg tcgaaagt                                                     18

<210> SEQ ID NO 32
<211> LENGTH: 18
<212> TYPE: DNA
<213> ORGANISM: Artificial sequence
<220> FEATURE:
<223> OTHER INFORMATION: primer

<400> SEQUENCE: 32
gcgtgcagcg gtttagtt                                                     18

<210> SEQ ID NO 33
<211> LENGTH: 18
<212> TYPE: DNA
<213> ORGANISM: Artificial sequence
<220> FEATURE:
<223> OTHER INFORMATION: primer

<400> SEQUENCE: 33
ggcctcctgg agtcacaa                                                     18

<210> SEQ ID NO 34
<211> LENGTH: 17
<212> TYPE: DNA
<213> ORGANISM: Artificial sequence
<220> FEATURE:
<223> OTHER INFORMATION: primer

<400> SEQUENCE: 34
ggcagtcttt tcgggca                                                      17

<210> SEQ ID NO 35
<211> LENGTH: 18
<212> TYPE: DNA
<213> ORGANISM: Artificial sequence
<220> FEATURE:
<223> OTHER INFORMATION: primer

<400> SEQUENCE: 35
ccttggctca ggtgctgt                                                     18

<210> SEQ ID NO 36
<211> LENGTH: 21
<212> TYPE: DNA
<213> ORGANISM: Artificial sequence
<220> FEATURE:
<223> OTHER INFORMATION: primer

<400> SEQUENCE: 36
tttgcaaaag ctagatccca a                                                 21

<210> SEQ ID NO 37
<211> LENGTH: 18
<212> TYPE: DNA
<213> ORGANISM: Artificial sequence
<220> FEATURE:
<223> OTHER INFORMATION: primer

<400> SEQUENCE: 37
gggcttctgg aatgagca                                                     18
```

```
<210> SEQ ID NO 38
<211> LENGTH: 18
<212> TYPE: DNA
<213> ORGANISM: Artificial sequence
<220> FEATURE:
<223> OTHER INFORMATION: primer

<400> SEQUENCE: 38
agcaagaggg gtgggaag                                                18

<210> SEQ ID NO 39
<211> LENGTH: 18
<212> TYPE: DNA
<213> ORGANISM: Artificial sequence
<220> FEATURE:
<223> OTHER INFORMATION: primer

<400> SEQUENCE: 39
acatccccca gcttgttg                                                18

<210> SEQ ID NO 40
<211> LENGTH: 18
<212> TYPE: DNA
<213> ORGANISM: Artificial sequence
<220> FEATURE:
<223> OTHER INFORMATION: primer

<400> SEQUENCE: 40
tgcagacaaa ccacccct                                                18

<210> SEQ ID NO 41
<211> LENGTH: 18
<212> TYPE: DNA
<213> ORGANISM: Artificial sequence
<220> FEATURE:
<223> OTHER INFORMATION: primer

<400> SEQUENCE: 41
agggcctgat cttttggc                                                18

<210> SEQ ID NO 42
<211> LENGTH: 18
<212> TYPE: DNA
<213> ORGANISM: Artificial sequence
<220> FEATURE:
<223> OTHER INFORMATION: primer

<400> SEQUENCE: 42
cagccacagc ctcccttta                                               18

<210> SEQ ID NO 43
<211> LENGTH: 18
<212> TYPE: DNA
<213> ORGANISM: Artificial sequence
<220> FEATURE:
<223> OTHER INFORMATION: primer

<400> SEQUENCE: 43
catatggggc cagttcca                                                18

<210> SEQ ID NO 44
<211> LENGTH: 18
<212> TYPE: DNA
<213> ORGANISM: Artificial sequence
<220> FEATURE:
<223> OTHER INFORMATION: primer
```

```
<400> SEQUENCE: 44
tgtgagtggc ggtctgaa                                                       18

<210> SEQ ID NO 45
<211> LENGTH: 22
<212> TYPE: RNA
<213> ORGANISM: Homo sapiens

<400> SEQUENCE: 45
uaacacuguc ugguaacgau gu                                                  22

<210> SEQ ID NO 46
<211> LENGTH: 21
<212> TYPE: RNA
<213> ORGANISM: Homo sapiens

<400> SEQUENCE: 46
agaggauacc cuuuguaugu u                                                   21

<210> SEQ ID NO 47
<211> LENGTH: 21
<212> TYPE: RNA
<213> ORGANISM: Homo sapiens

<400> SEQUENCE: 47
gugcauugua guugcauugc a                                                   21

<210> SEQ ID NO 48
<211> LENGTH: 22
<212> TYPE: RNA
<213> ORGANISM: Homo sapiens

<400> SEQUENCE: 48
cacgcucaug cacacaccca ca                                                  22

<210> SEQ ID NO 49
<211> LENGTH: 115
<212> TYPE: RNA
<213> ORGANISM: Homo sapiens

<400> SEQUENCE: 49
ggugccgagg gccguccggc auccuaggcg ggucgcugcg guaccucccu ccugucugug         60 gcgguggggau cccguggccg uguuuuccug guggcccggc cgugccugag guuuc            115
```

THERANOSTIC TOOLS FOR MANAGEMENT OF PANCREATIC CANCER AND ITS PRECURSORS

CROSS-REFERENCE TO RELATED APPLICATIONS

The present application 18 the National Stage of International Application No. PCT/US2018/030994, filed May 3, 2018, which claims the benefit of U.S. Provisional Application Ser. No. 62/501,040, filed May 3, 2017, which is hereby incorporated by reference herein in its entirety, including any figures, tables, nucleic acid sequences, amino acid sequences, or drawings.

GOVERNMENT SUPPORT

This invention was made with Government support under Grant No. CA076292 and 1R37CA229810-01A1 (PI Daniel Jeong) awarded by the National Institutes of Health. The Government has certain rights in the invention.

SEQUENCE LISTING

The Sequence Listing for this application is labeled "2OZ1697.TXT" which was created on Oct. 26, 2019 and is 9 KB. The entire contents of the sequence listing is incorporated herein by reference in its entirety.

BACKGROUND OF THE INVENTION

Intraductal papillary mucinous neoplasms (IPMN) are incidentally-detected pancreatic cysts that are challenging to manage due to the inability to predict which cysts can be safely monitored, which are likely to progress to invasive pancreatic cancer, and which may have an associated invasive component. Differentiating between high-risk and low-risk intraductal papillary mucinous neoplasms (IPMNs) of the pancreas is a significant clinical problem.

Pancreatic ductal adenocarcinoma (PDAC) is the fourth leading cause of cancer mortality in the United States, claiming the lives of nearly 40,000 individuals each year. Surgical resection offers the best chance for improved survival, but 80-85% of cases are unresectable at diagnosis. These statistics underscore the urgent need to develop strategies to detect PDAC at an early, operable stage.

It is established that PDAC does not arise de novo, but instead marks the end of progression from one of three types of non-invasive precursor lesions arising within exocrine pancreatic ducts: pancreatic intraepithelial neoplasia (PanIN), mucinous cystic neoplasms (MCNs), and intraductal papillary mucinous neoplasms (IPMNs). While PanINs are microscopic lesions in ducts <5 mm in diameter, MCNs and IPMNs are macroscopic mucinous cysts accounting for over half of the estimated 150,000 asymptomatic pancreatic cysts detected incidentally in the general population each year due to increased computed tomography and magnetic resonance imaging. Although improvements in imaging, cytology, and molecular studies have enabled proper classification and management of some benign non-neoplastic pancreatic cysts, mucinous cysts such as IPMNs are challenging for the patient and clinical team to manage due to the inability to accurately predict which lesions can be monitored, which are likely to progress to invasion, and which may have an associated invasive component. Since data highlight a two-decade window of opportunity for early detection efforts in PDAC, IPMNs represent prime targets for the early detection and prevention of progression to invasive, fatal disease.

IPMNs present within the main pancreatic duct (MD-IPMN), side branch ducts (BD-IPMN), or both (mixed-IPMN), and are further classified based on the degree of dysplasia which ranges from adenoma (low-grade dysplasia, LG) and borderline (moderate-grade dysplasia, MG) to carcinoma in situ (high-grade dysplasia, HG) and invasive carcinoma. MD-IPMNs are associated with a higher grade and faster growth compared to BD-IPMNs, with the 5-year risk of developing HG or invasive disease from an adenoma to be ~63% for MD-IPMNs and 15% for BD-IPMNs. Other predictors of malignant potential include main duct dilation (>5 mm), mural nodules, cyst size (>3 cm), and symptoms such as jaundice and abdominal pain. Consensus guidelines recommend resection for surgically-fit patients with MD-IPMNs and careful observation for asymptomatic BD-IPMNs measuring <3 cm in the absence of mural nodules, main-duct dilation, or positive cytology. However, these guidelines do not reliably predict the degree of dysplasia. To date, the only way to treat IPMNs and accurately identify the grade of dysplasia is through surgical resection and pathological evaluation, but the risks of morbidity (i.e. long-term diabetes) and mortality associated with a Whipple procedure or a distal or total pancreatectomy may outweigh the benefits, especially for patients with LG disease. Alternatively, taking a 'watch and wait' approach could lead to a missed opportunity for successful intervention for a patient harboring occult invasive disease.

BRIEF SUMMARY OF THE INVENTION

The present invention concerns materials and methods for identifying and classifying pancreatic ductal adenocarcinoma (PDAC) precursors using messenger RNAs, microRNAs, long non-coding RNAs, radiomic features, radiologic measures of abdominal/visceral obesity, and combinations thereof, as diagnostic markers for integration with clinical management and interventions for personalized care.

Precancerous Intraductal Papillary Mucinous Neoplasms (IPMNs) account for nearly half of the 150,000 pancreatic cysts discovered incidentally on CT or MRI scans each year. There is an unmet need to develop a readily-available, cost-effective, and accurate blood-based biomarker test that can act as a diagnostic adjunct to radiologic characteristics and help improve diagnostic performance, especially for individuals who only present with "worrisome features" (WF). miRNAs represent ideal candidates for overcoming some limitations of single blood-based biomarkers because they reflect physiological and pathological conditions and act as extracellular messengers of biological signals derived from the cross talk between the tumor and its microenvironment.

The inventors have determined that the addition of miRNAs obtained pre-operatively from blood (e.g., plasma) increases diagnostic performance and can aid with medical decision-making, especially when combined with a new set of quantitative 'radiomic' features hidden to the radiologist's eyes. One aspect of the invention is a method that combines a blood-based five microRNA (miRNA) signature along with radiomic features to distinguish pre-cancerous malignant Intraductal Papillary Mucinous Neoplasms (IPMNs) from benign ones. PMNs are pancreatic cancer precursors incidentally discovered by cross-sectional imaging. Consensus guidelines for IPMN management rely on standard radiologic features to predict pathology. However, these criteria lack accuracy in predicting final pathology and can result in resection of benign disease (over-treatment) or no surgical intervention for malignant disease (under-treatment). Using a retrospective cohort of 38 surgically-resected, pathologically-confirmed IPMNs (20 benign; 18 malignant) with preoperative computed tomography (CT) images and matched plasma-based miRNA genomic classifier (MGC) data, the inventors determined that quantitative radiomic CT features (+/− the MGC) can more accurately predict IPMN pathology than standard radiologic features that classify patients as 'high-risk' or 'worrisome' for malignancy. The MGC, "high-risk," and "worrisome" radiologic features had area under the receiver operating characteristic curve (AUC) values of 0.83, 0.84, and 0.54, respectively. Fourteen radiomic features differentiated malignant from benign IPMNs (p<0.05) and collectively had an AUC=0.77. Combining radiomic features with the MGC revealed an AUC=0.92 and superior sensitivity (83%), specificity (89%), PPV (88%), and NPV (85%) than other models.

BRIEF DESCRIPTION OF THE DRAWINGS

FIG. 2A: Box plots of the distribution of the 9-mRNA signature score (designated by the first principal component (PC1)) within the malignant and benign groups. FIG. 2B: Receiver operating characteristic (ROC) curve analysis showed that the 9-mRNA signature PC1 yielded an area under the curve (AUC) value of 0.748 in differentiating between groups.

FIG. 4C and FIG. 4D: (1) Axial CT image through L2-L3 intervertebral disc level. (2) Axial CT subtracted image at superior endplate of L3. Abdominal wall and paraspinal muscle area were segmented and thresholds set to voxels with Hounsfield units (HU) −29 to 150. Visceral fat, intra-abdominal organs, and vasculature were subtracted. Although skeletal muscle indices can be obtained in a complementary manner to visceral fat measurements, these were not directly analyzed in this study. (3) Total abdominal fat with HU thresholds applied to include fat density voxels with HU −249 to −49 (green). (4) Manual segmentation of visceral fat regions (green).

FIG. 6A) Box plots of the distribution of the 8-lncRNA signature score (designated by the first principal component (PC1)) within the malignant and benign groups. FIG. 6B) Receiver operating characteristic (ROC) curve analysis showed that the 8-lncRNA signature PC1 yielded an area under the curve (AUC) value of 0.77 (95% CI: 0.62-0.92) in differentiating between groups.

FIG. 8A: Axial venous phase images through the abdomen demonstrate a cystic mass in the pancreatic head/neck measuring up to 3.5 cm. This lesion contains a non-enhancing soft tissue mural nodule (arrow). FIG. 8B: Axial venous phase images through the abdomen demonstrate an ovoid, homogeneous appearing cystic mass measuring up to 4.8 cm in greatest dimension. No internal enhancing soft tissue nodules were seen within the lesion.

BRIEF DESCRIPTION OF THE SEQUENCES

Figure 1:
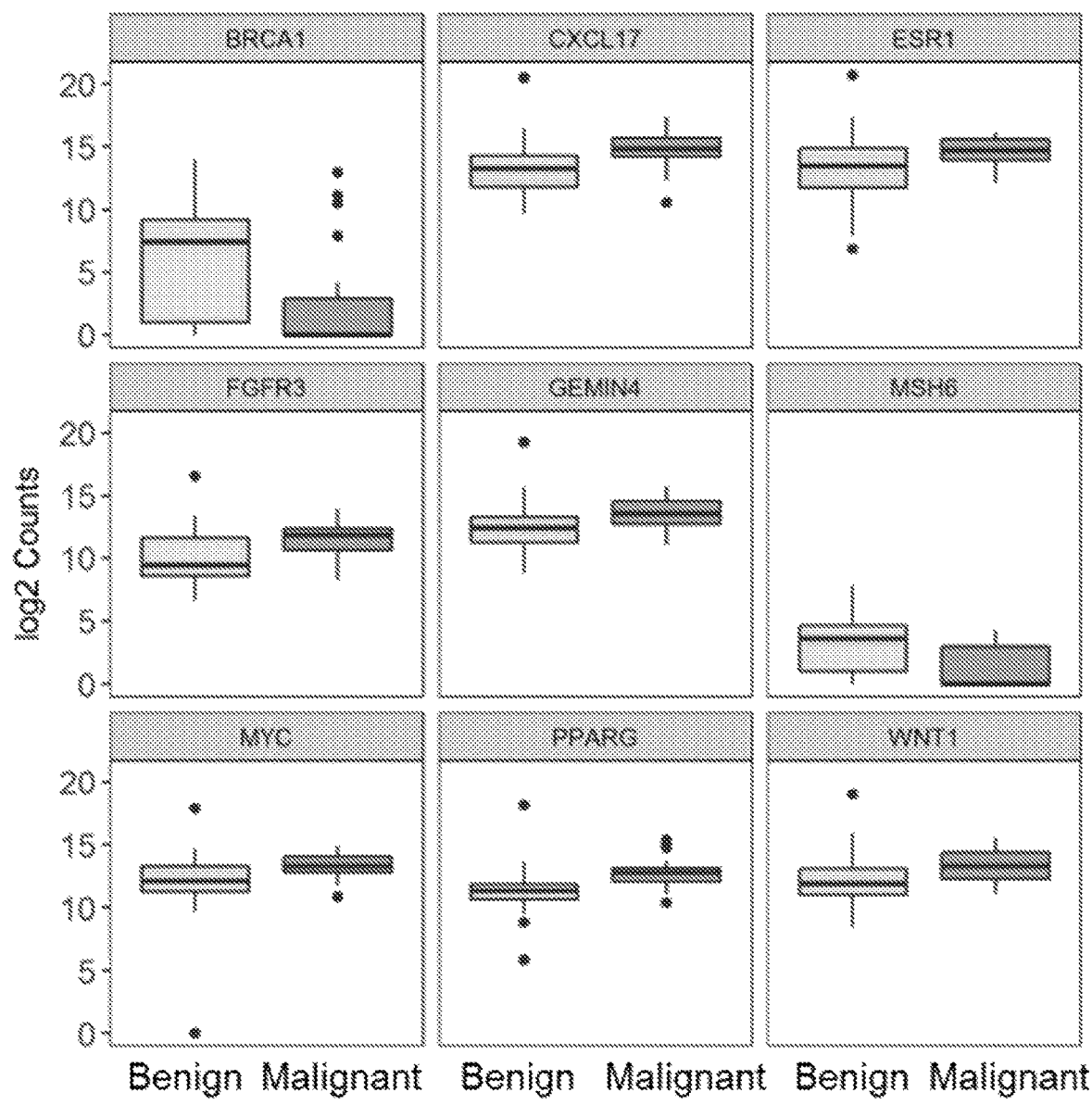
FIG. 1. Nine mRNAs in circulation discriminated malignant (n=30) from benign (n=21) IPMN cases (p<0.05). Box plots displaying the distribution of the abundance of each individual mRNA within the malignant and benign groups.

SEQ ID NOs:1 and 2 are forward and reverse primers for GKN2.
SEQ ID NOs:3 and 4 are forward and reverse primers for CD19.
SEQ ID NOs:5 and 6 are forward and reverse primers for BRCA1.
SEQ ID NOs:7 and 8 are forward and reverse primers for HRAS.
SEQ ID NOs:9 and 10 are forward and reverse primers for CXCL17.
SEQ ID NOs:11 and 12 are forward and reverse primers for ESR1.
SEQ ID NOs:13 and 14 are forward and reverse primers for FGFR3.
SEQ ID NOs:15 and 16 are forward and reverse primers for GEMIN4.
SEQ ID NOs:17 and 18 are forward and reverse primers for MSH6.
SEQ ID NOs:19 and 20 are forward and reverse primers for MYC.
SEQ ID NOs:21 and 22 are forward and reverse primers for PPARG.

SEQ ID NOs:23 and 24 are forward and reverse primers for WNT1.

SEQ ID NOs:25 and 26 are forward and reverse primers for GAS5.

SEQ ID NOs:27 and 28 are forward and reverse primers for SRA.

SEQ ID NOs:29 and 30 are forward and reverse primers for ADARB2-AS1.

SEQ ID NOs:31 and 32 are forward and reverse primers for ANRIL.

SEQ ID NOs:33 and 34 are forward and reverse primers for GLIS3-AS1.

SEQ ID NOs:35 and 36 are forward and reverse primers for LINC00472

SEQ ID NOs:37 and 38 are forward and reverse primers for MEG3.

SEQ ID NOs:39 and 40 are forward and reverse primers for PANDA.

SEQ ID NOs:41 and 42 are forward and reverse primers for PVT1.

SEQ ID NOs:43 and 44 are forward and reverse primers for UCA1.

```
SEQ ID NO: 45 is human miRNA "hsa-miR-200a-3p":
UAACACUGUCUGGUAACGAUGU (Accession No.
MIMAT0000682)

SEQ ID NO: 46 is human miRNA "hsa-miR-1185-5p":
AGAGGAUACCCUUUGUAUGUU (Accesion No. MIMAT0005798)

SEQ ID NO: 47 is human miRNA "hsa-miR-33a-5p":
GUGCAUUGUAGUUGCAUUGCA (Accession No. MIMAT0000091)

SEQ ID NO: 48 is human miRNA "hsa-miR-574-3p":
CACGCUCAUGCACACACCCACA (Accession No.

MIMAT0003239)

SEQ ID NO: 49 is human miRNA "hsa-mir-663b"
GGUGCCGAGGGCCGUCCGGCAUCCUAGGCGGGUCGCUGCGGUACCUCCCU

CCUGUCUGUGGCGGUGGGAUCCCGUGGCCGUGUUUUCCUGGUGGCCCGGC

CGUGCCUGAGGUUUC (Accession No. MI0006336)
```

DETAILED DESCRIPTION OF THE INVENTION

Permuth-Wey et al. ("Plasma MicroRNAs as Novel Biomarkers for Patients with Intraductal Papillary Mucinous Neoplasms of the Pancreas," Cancer Prev Res., 8(9):826-834, September 2015); Permuth et al. ("Combining radiomic features with a miRNA classifier may improve prediction of malignant pathology for pancreatic intraductal papillary mucinous neoplasms," Oncotarget, 7(52):85785-85797, December 2016); and International Patent Application Publication Number WO2015/153679 (Malafa M P et al., to H. Lee Moffitt Cancer Center and Research Institute, Inc., "MicroRNA Assay for Detection and Management of Pancreatic Cancer Precursors", international application number PCT/US2015/023702, published Oct. 8, 2015) are each incorporated herein by reference in their entirety, including all figures, tables, and sequences).

In the treatments methods of the invention involving administering a treatment to the subject, the treatment may be, for example, surgery (e.g., resection), radiation, and/or administration of an anti-cancer agent such as a chemotherapuetics (e.g., DNA-binding alkylating agents) and immune modulators (see, for example, Wong K K et al., "The Role of Precision Medicine in Pancreatic Cancer: Challenges of Targeted Therapy, Immune Modulating Treatment, Early Detection, and Less Invasive Operations," Cancer Transl Med., 2:41-7, 2016; Wolfgang C L et al., "Recent Progress in Pancreatic Cancer," CA Cancer J Clin, 63(5):318-348, September 2013; Grutzman R et al., "Intraductal Papillary Mucinous Neoplasia (IPMN) of the Pancrease, its Diagnosis, Treatment and Prognosis," Dtsch Arztebl Int., 108:46:788-794, November 2011; Grutzman R et al. "Intraductal Papillary Mucinous Tumours of the Pancreas: Biology, Diagnosis, and Treatment, The Oncologist, 15:1294-1309, 2010, which are each incorporated herein by reference in their entirety).

Examples of interventions for pancreatic cancer and lesions such as IPMNs include, but are not limited to:

Surgeries (Surgical Interventions):

Enucleation (removing just the tumor): If a pancreatic neuroendocrine tumor is small, just the tumor itself is removed. This is called enucleation.

Whipple procedure (pancreaticoduodenectomy): removing the head of the pancreas and sometimes the body of the pancreas as well. Nearby structures such as part of the small intestine, part of the bile duct, the gallbladder, lymph nodes near the pancreas, and sometimes part of the stomach are also removed.

Distal pancreatectomy: removing only the tail of the pancreas or the tail and a portion of the body of the pancreas.

Total pancreatectomy: removing the entire pancreas, as well as the gallbladder, part of the stomach and small intestine, and the spleen.

Palliative surgery: If the cancer has spread too far to be removed completely, any surgery being considered would be palliative (intended to relieve or prevent symptoms).

Ablative Treatments:

Ablation refers to treatments that destroy tumors, usually with extreme heat or cold.

Radiofrequency ablation (RFA): Using high-energy radio waves for treatment. A thin, needle-like probe is placed through the skin and into the tumor. An electric current then passes through the tip of the probe, which heats the tumor and destroys the cancer cells. This treatment is used mainly for small tumors.

Microwave thermotherapy: This procedure is similar to RFA, except microwaves are used to heat and destroy the tumor.

Cryosurgery (also known as cryotherapy or cryoablation): Destroying a tumor by freezing it. A thin metal probe is guided into the tumor, and very cold gasses pass through the probe to freeze the tumor, killing the cancer cells.

Embolization: Embolization involves injecting substances into an artery to try to block the blood flow to cancer cells, causing them to die.

Arterial embolization: This is also known as trans-arterial embolization (or TAE). A catheter (a thin, flexible tube) is put into an artery through a small cut in the inner thigh and threaded up into the artery feeding the tumor and small particles are injected into the artery to plug it up.

Chemoembolization: This is also known as trans-arterial chemoembolization (or TACE), which combines embolization with chemotherapy. This involves using tiny beads that give off a chemotherapy drug for the embolization. TACE can also be done by giving chemotherapy through the catheter directly into the artery, then plugging up the artery.

Radioembolization: This combines embolization with radiation therapy. This involves injecting small radioactive beads (called microspheres) into the artery. The beads lodge in the blood vessels near the tumor, where they give off small amounts of radiation to the tumor site for several days. The radiation travels a very short distance, so its effects are limited mainly to the tumor.

Anti-Cancer Agents Such as Drugs:
  Abraxane (Paclitaxel Albumin-stabilized Nanoparticle Formulation)
  Afinitor (Everolimus)
  Erlotinib Hydrochloride
  Everolimus
  Fluorouracil Injection
  Gemcitabine Hydrochloride
  Mitomycin C
  Mitozytrex (Mitomycin C)
  Mutamycin (Mitomycin C)
  Sunitinib Malate
  Sutent (Sunitinib Malate)
  Lanreotide Acetate
  Lutathera (Lutetium Lu 177-Dotatate)
  Lutetium Lu 177-Dotatate
  Somatuline Depot (Lanreotide Acetate)
  Folfirinox: FOL=Leucovorin Calcium (Folinic Acid); F=Fluorouracil; IRIN=Irinotecan Hydrochloride; OX=Oxaliplatin (this is different from what you identified below)
  Gemcitabine Hydrochloride and Cisplatin
  Gemcitabine Hydrochloride and Oxaliplatin
  OFF: O=Oxaliplatin; F=Fluorouracil; and F=Leucovorin Calcium (Folinic Acid)

Examples of chemotherapeutic treatment for pancreatic cancer and lesions such as IPMNs include, but are not limited to: erlotinib, Gemcitabine (Gemzar), 5-fluorouracil (5-FU), Irinotecan (Camptosar), Oxaliplatin (Eloxatin), Albumin-bound paclitaxel (Abraxane), Capecitabine (Xeloda), Cisplatin, Paclitaxel (Taxol), Docetaxel (Taxotere), and Irinotecan liposome (Onivyde). Examples of combination treatments include: a combination of Albumin-bound paclitaxel and gemcitabine; combination of Irinotecan liposome, 5-FU, and folinic acid (leucovorin); and combination of 5-FU, irinotecan and oxaliplatin (Folfirinox).

Other examples of anti-cancer agents that can be used as monotherapy or combination treatments are listed in Table 20.

Each method disclosed and claimed herein can be used in combination with any other method disclosed or claimed herein, carried out concurrently or consecutively in any order.

In some embodiments of the methods of the invention, the detecting or probing step comprises isolating the nucleic acid or portion thereof prior to the mixing step. In a further embodiment, the hybridization comprises hybridization of a cDNA to a cDNA, thereby forming a non-natural complex; or hybridization of a cDNA to an mRNA, thereby forming a non-natural complex. In a further embodiment, the probing step comprises amplifying the nucleic acid in the sample.

In some embodiments, the expression level of a marker such as an miRNA, mRNA, or lncRNA is measured by a technique selected from the group consisting of quantitative real-time PCR (qPCR), reverse transcription polymerase chain reaction (RT-PCR), rapid amplification of cDNA ends (RACE-PCR), multiplex RT-PCR, Northern blotting, nuclease protection assays, in situ hybridization, serial analysis of gene expression (SAGE), RNA microarray, RNA microarray and gene chips, and RNA sequencing (RNA-seq). Other measurement methods are described in WO2015/153679, which is incorporated by reference herein in its entirety.

As used herein, an "expression profile" comprises one or more values corresponding to a measurement of the relative abundance, level, presence, or absence of expression of a discriminative gene, messenger RNA (mRNA), microRNA (miRNA), or long non-coding RNA (lncRNA). An expression profile can be derived from a subject prior to or subsequent to a diagnosis of cancer (e.g., pancreatic cancer, intraductal papillary mucinous neoplasm, etc.), can be derived from a biological sample collected from a subject at one or more time points prior to or following treatment or therapy, can be derived from a biological sample collected from a subject at one or more time points during which there is no treatment or therapy (e.g., to monitor progression of disease or to assess development of disease in a subject diagnosed with or at risk for cancer), or can be collected from a healthy subject.

Isolated mRNA can be used in hybridization or amplification assays that include, but are not limited to, Southern or Northern analyses, PCR analyses and probe arrays, NanoString Assays. One method for the detection of mRNA levels involves contacting the isolated mRNA or synthesized cDNA with a nucleic acid molecule (probe) that can hybridize to the mRNA encoded by the gene being detected. The nucleic acid probe can be, for example, a cDNA, or a portion thereof, such as an oligonucleotide of at least 7, 15, 30, 50, 100, 250, or 500 nucleotides in length and sufficient to specifically hybridize under stringent conditions to the non-natural cDNA or mRNA biomarker of the present invention.

The present invention also includes arrays with oligonucleotide probes attached to a solid support for carrying out the methods described herein, wherein the probes hybridize with target sequences within one or more of the target markers described herein (mRNA, miRNA, lncRNA). In some embodiments, the array has oligonucleotide probes targeting 2, 3, 4, 5, 6, 7, 8, 9, 10, 11, 12, 13, 14, 15, 16, 17, 18, 19, or 20 or more markers described herein. In some embodiments, the array has oligonucleotide probes that target no more than 50, 100, or 500 total markers.

In some embodiments, once the mRNA is obtained from a sample, it is converted to complementary DNA (cDNA) in a hybridization reaction. cDNA does not exist in vivo and therefore is a non-natural molecule. In a further embodiment, the cDNA is then amplified, for example, by the polymerase chain reaction (PCR) or other amplification method known to those of ordinary skill in the art. The product of this amplification reaction, i.e., amplified cDNA is necessarily a non-natural product. As mentioned above, cDNA is a non-natural molecule. Second, in the case of PCR, the amplification process serves to create hundreds of millions of cDNA copies for every individual cDNA molecule of starting material. The number of copies generated are far removed from the number of copies of mRNA that are present in vivo.

In one embodiment, cDNA is amplified with primers that introduce an additional DNA sequence (adapter sequence) onto the fragments (with the use of adapter-specific primers). Amplification therefore serves to create non-natural double stranded molecules from the non-natural single stranded cDNA, by introducing barcode, adapter and/or reporter sequences onto the already non-natural cDNA. In one embodiment, during amplification with the adapter-specific primers, a detectable label, e.g., a fluorophore, is added to single strand cDNA molecules. Amplification therefore also serves to create DNA complexes that do not occur in nature, at least because (i) cDNA does not exist in vivo, (i) adapter sequences are added to the ends of cDNA molecules to make DNA sequences that do not exist in vivo, (ii) the error rate associated with amplification further creates DNA sequences that do not exist in vivo, (iii) the disparate structure of the cDNA molecules as compared to what exists in nature and (iv) the chemical addition of a detectable label to the cDNA molecules.

In some embodiments, the synthesized cDNA (for example, amplified cDNA) is immobilized on a solid surface via hybridization with a probe, e.g., via a microarray. In another embodiment, cDNA products are detected via real-time polymerase chain reaction (PCR) via the introduction of fluorescent probes that hybridize with the cDNA products. For example, in one embodiment, biomarker detection is assessed by quantitative fluorogenic RT-PCR (e.g., with TaqMan® probes). For PCR analysis, well known methods are available in the art for the determination of primer sequences for use in the analysis.

Biomarkers provided herein in some embodiments, are detected via a hybridization reaction that employs a capture probe and/or a reporter probe. For example, the hybridization probe is a probe derivatized to a solid surface such as a bead, glass or silicon substrate. In another embodiment, the capture probe is present in solution and mixed with the patient's sample, followed by attachment of the hybridization product to a surface, e.g., via a biotin-avidin interaction (e.g., where biotin is a part of the capture probe and avidin is on the surface). The hybridization assay in one embodiment, employs both a capture probe and a reporter probe. The reporter probe can hybridize to either the capture probe or the biomarker nucleic acid. Reporter probes, e.g., are then counted and detected to determine the level of biomarker(s) in the sample. The capture and/or reporter probe, in one embodiment contain a detectable label, and/or a group that allows functionalization to a surface.

For example, the nCounter gene analysis system (see, e.g., Geiss et al. (2008) *Nat. Biotechnol.* 26, pp. 317-325, which is incorporated herein by reference in its entirety for all purposes, may be used to carry out the methods provided herein.

Hybridization assays described in U.S. Pat. Nos. 7,473,767 and 8,492,094, the disclosures of which are incorporated by reference in their entireties for all purposes, may be used to carry out the methods provided herein, i.e., to detect the biomarkers and biomarker combinations described herein.

Biomarker levels may be monitored using a membrane blot (such as used in hybridization analysis such as Northern, Southern, dot, and the like), or microwells, sample tubes, gels, beads, or fibers (or any solid support comprising bound nucleic acids). See, for example, U.S. Pat. Nos. 5,770,722, 5,874,219, 5,744,305, 5,677,195 and 5,445,934, each incorporated herein by reference in their entireties.

In some embodiments, microarrays are used to detect biomarker levels. Microarrays are particularly well suited for this purpose because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected by laser scanning Hybridization intensities for each probe on the array are determined and converted to a quantitative value representing relative gene expression levels. See, for example, U.S. Pat. Nos. 6,040,138, 5,800,992 and 6,020,135, 6,033,860, and 6,344,316, each incorporated by reference in their entireties. High-density oligonucleotide arrays are particularly useful for determining the biomarker profile for a large number of RNAs in a sample.

Techniques for the synthesis of these arrays using mechanical synthesis methods are described in, for example, U.S. Pat. No. 5,384,261. Although a planar array surface is generally used, the array can be fabricated on a surface of virtually any shape or even a multiplicity of surfaces. Arrays can be nucleic acids (or peptides) on beads, gels, polymeric surfaces, fibers (such as fiber optics), glass, or any other appropriate substrate. See, for example, U.S. Pat. Nos. 5,770,358, 5,789,162, 5,708,153, 6,040,193 and 5,800,992, each incorporated by reference in their entireties. Arrays can be packaged in such a manner as to allow for diagnostics or other manipulation of an all-inclusive device. See, for example, U.S. Pat. Nos. 5,856,174 and 5,922,591, each incorporated by reference in their entireties.

Serial analysis of gene expression (SAGE) in one embodiment is employed in the methods described herein. SAGE is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, Velculescu et al. *Science* 270:484-87, 1995; Cell 88:243-51, 1997, which is incorporated herein by reference in its entirety.

An additional method of biomarker level analysis at the nucleic acid level is the use of a sequencing method, for example, RNAseq, next generation sequencing, and massively parallel signature sequencing (MPSS), as described by Brenner et al. (*Nat. Biotech.* 18:630-34, 2000, incorporated by reference in its entirety). This is a sequencing approach that combines non-gel-based signature sequencing with in vitro cloning of millions of templates on separate 5 .mu.m diameter microbeads. First, a microbead library of DNA templates is constructed by in vitro cloning. This is followed by the assembly of a planar array of the template-containing microbeads in a flow cell at a high density (typically greater than $3.0 \times 10^6$ microbeads/cm$^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

Immunohistochemistry methods are also suitable for detecting the levels of the biomarkers of the present invention. Samples can be frozen for later preparation or immediately placed in a fixative solution. Tissue samples can be fixed by treatment with a reagent, such as formalin, gluteraldehyde, methanol, or the like and embedded in paraffin. Methods for preparing slides for immunohistochemical analysis from formalin-fixed, paraffin-embedded tissue samples are well known in the art.

Various statistical methods can be used to aid in the comparison of the biomarker levels obtained from the subject and reference biomarker levels. Reference biomarker levels can represent the level of a state of normalcy or health or a state of disease for comparison.

As used herein, the term "(therapeutically) effective amount" refers to an amount of an agent (e.g., an anti-cancer agent) effective to treat a disease or disorder in a mammal, such as pancreatic cancer or an IPMN. In the case of cancer or other proliferation disorder, the therapeutically effective amount of the agent may reduce (i.e., slow to some extent and preferably stop) unwanted cellular proliferation; reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve, to some extent, one or more of the symptoms associated with the cancer. To the extent the administered agent prevents growth of and/or kills existing cancer cells, it may be cytostatic and/or cytotoxic. For cancer therapy, efficacy can, for example, be measured by assessing the time to disease progression (TTP) and/or determining the response rate (RR).

As used herein, the term "growth inhibitory amount" of the anti-cancer agent refers to an amount which inhibits growth or proliferation of a target cell, such as a tumor cell, either in vitro or in vivo, irrespective of the mechanism by which cell growth is inhibited (e.g., by cytostatic properties, cytotoxic properties, etc.). In a preferred embodiment, the growth inhibitory amount inhibits (i.e., slows to some extent and preferably stops) proliferation or growth of the target cell in vivo or in cell culture by greater than about 20%, preferably greater than about 50%, most preferably greater than about 75% (e.g., from about 75% to about 100%).

As used herein, the term "anti-cancer agent" refers to a substance or treatment (e.g., radiation therapy) that inhibits the function of cancer cells, inhibits their formation, and/or causes their destruction in vitro or in vivo. Examples include, but are not limited to, cytotoxic agents (e.g., 5-fluorouracil, TAXOL), chemotherapeutic agents, and anti-signaling agents (e.g., the PI3K inhibitor LY). Anti-cancer agents include but are not limited to those listed Table 20.

As used herein, the term "cytotoxic agent" refers to a substance that inhibits or prevents the function of cells and/or causes destruction of cells in vitro and/or in vivo. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents, toxins such as small molecule toxins or enzymatically active toxins of bacterial, fungal, plant or animal origin, and antibodies, including fragments and/or variants thereof.

As used herein, the term "chemotherapeutic agent" is a chemical compound useful in the treatment of cancer, such as, for example, taxanes, e.g., paclitaxel (TAXOL, BRISTOL-MYERS SQUIBB Oncology, Princeton, N.J.) and doxetaxel (TAXOTERE, Rhone-Poulenc Rorer, Antony, France), chlorambucil, vincristine, vinblastine, anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON, GTx, Memphis, TN), and anti-androgens such as flutamide, nilutamide, bicalutamide, leuprolide, and goserelin, etc. Examples of chemotherapeutic agents that may be used in conjunction with the compounds of the invention are listed in Table 14. In some embodiments, the chemotherapeutic agent is one or more anthracyclines. Anthracyclines are a family of chemotherapy drugs that are also antibiotics. The anthracyclines act to prevent cell division by disrupting the structure of the DNA and terminate its function by: (1) intercalating into the base pairs in the DNA minor grooves; and (2) causing free radical damage of the ribose in the DNA. The anthracyclines are frequently used in leukemia therapy. Examples of anthracyclines include daunorubicin (CERUBIDINE), doxorubicin (ADRIAMYCIN, RUBEX), epirubicin (ELLENCE, PHARMORUBICIN), and idarubicin (IDAMYCIN).

As used herein, the term "tumor" refers to all neoplastic cell growth and proliferation, whether malignant or benign, and all pre-cancerous and cancerous cells and tissues. For example, a particular cancer may be characterized by a solid tumor mass or a non-solid tumor. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture, or weight of the tissue. However, some primary tumors are not palpable and can be detected only through medical imaging techniques such as X-rays (e.g., mammography), or by needle aspirations. The use of these latter techniques is more common in early detection. Depending upon the agent, anti-cancer agents can be administered locally at the site of a tumor (e.g., by direct injection) or remotely.

As used in this specification, the singular forms "a", "an", and "the" include plural reference unless the context clearly dictates otherwise. Thus, for example, a reference to "a cell" includes one or more cells. A reference to "a mRNA" includes one or more such mRNA, and so forth.

The practice of the present invention can employ, unless otherwise indicated, conventional techniques of molecular biology, microbiology, recombinant DNA technology, electrophysiology, and pharmacology that are within the skill of the art. Such techniques are explained fully in the literature (see, e.g., Sambrook, Fritsch & Maniatis, Molecular Cloning: A Laboratory Manual, Second Edition (1989); DNA Cloning, Vols. I and II (D. N. Glover Ed. 1985); Perbal, B., A Practical Guide to Molecular Cloning (1984); the series, Methods In Enzymology (S. Colowick and N. Kaplan Eds., Academic Press, Inc.); Transcription and Translation (Hames et al. Eds. 1984); Gene Transfer Vectors For Mammalian Cells (J. H. Miller et al. Eds. (1987) Cold Spring Harbor Laboratory, Cold Spring Harbor, N.Y.); Scopes, Protein Purification: Principles and Practice (2nd ed., Springer-Verlag); and PCR: A Practical Approach (McPherson et al. Eds. (1991) IRL Press)), each of which are incorporated herein by reference in their entirety.

EXEMPLIFIED EMBODIMENTS

1. A method for detecting microRNAs (miRNA) in human blood and assessing radiomic features, comprising:
   detecting the level of one or more miRNAs (e.g., 1, 2, 3, 4, 5, or more) in a human blood sample selected from among: miR-200a-3p, miR-1185-5p, miR-33a-5p, miR-574-4p, and miR-664b; and
   extracting quantitative radiomic features from a medical image of the subject.

2. The method of embodiment 1, wherein the one or more miRNAs are each of miR-200a-3p, miR-1185-5p, miR-33a-5p, miR-574-4p, and miR-664b.

3. The method of embodiment 1, wherein the human blood sample is a sample of whole blood, serum, or plasma.

4. The method of embodiment 1, wherein the human blood sample is plasma.

5. The method of any one of embodiments 1 to 4, wherein the one or more miRNAs are each of miR-200a-3p, miR-1185-5p, miR-33a-5p, miR-574-4p, and miR-664b, and the human blood sample is plasma.

6. The method of any one of embodiments 1 to 5, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

7. The method of any one of embodiment 1 to 6, wherein the medical image is a computed tomography (CT) scan (e.g., multi-phase CT scan) or magnetic resonance imaging (MRI).

8. The method of any one of embodiment 1 to 7, wherein the quantitative radiomic features comprise one or more radiomic features in Table 12 (Fourier Descriptor Layer 1, Histogram Energy Layer 1, Histogram Entropy Layer 1, Co-occurrence matrix features OF1 G1 CONTRAST Layer 1, Run-length features G1 D0 HGRE Layer 1, Run-length features G1 D0 LGRE Layer 1, Laws features E5 E5 Energy Layer 1, Laws features L5 S5 Energy Layer 1, Laws features R5 E5 Energy Layer 1, Wavelet decomposition P1 L3 C1 Layer 1, Wavelet decomposition P1 L3 C2 Layer 1, Border length (Pxl), Width (Pxl), and Radius of largest enclosed ellipse).

9. The method of embodiment 8, wherein the quantitative radiomic features comprise each of the radiomic features in Table 12 (Fourier Descriptor Layer 1, Histogram Energy Layer 1, Histogram Entropy Layer 1, Co-occurrence matrix features OF1 G1 CONTRAST Layer 1, Run-length features G1 D0 HGRE Layer 1, Run-length features G1 D0 LGRE Layer 1, Laws features E5 E5 Energy Layer 1, Laws features L5 S5 Energy Layer 1, Laws features R5 E5 Energy Layer 1, Wavelet decomposition P1 L3 C1 Layer 1, Wavelet decomposition P1 L3 C2 Layer 1, Border length (Pxl), Width (Pxl), and Radius of largest enclosed ellipse).

10. An integrated blood-based miRNA and radiomic method of assessing the severity or potential pathology of a intraductal papillary mucinous neoplasm (IPMN) in a human subject, comprising:
  detecting the level of one or more miRNAs (e.g., 1, 2, 3, 4, 5, or more) in a human blood sample selected from among: miR-200a-3p, miR-1185-5p, miR-33a-5p, miR-574-4p, and miR-664b;
  extracting quantitative radiomic features from a medical image of the subject; comparing the detected level and extracted radiomic features to a reference level and reference radiomic features; and
  classifying the severity or potential pathology of the IPMN based on the results of the comparing step.

11. The method of embodiment 10, wherein the one or more miRNAs are each of miR-200a-3p, miR-1185-5p, miR-33a-5p, miR-574-4p, and miR-664b.

12. The method of embodiment 10 or 11, wherein the human blood sample is a sample of whole blood, serum, or plasma.

13. The method of any one of embodiments 10 to 12, wherein the human blood sample is plasma.

14. The method of embodiment 10, wherein the one or more miRNAs are each of miR-200a-3p, miR-1185-5p, miR-33a-5p, miR-574-4p, and miR-664b, and the human blood sample is plasma.

15. The method of any one of embodiments 10 to 14, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

16. The method of any one of embodiments 10 to 15, wherein the medical image is a computed tomography (CT) scan (e.g., multi-phase CT scan) or magnetic resonance imaging (MRI).

17. The method of any one of embodiment 10 to 15, wherein the quantitative radiomic features comprise one or more radiomic features in Table 12 (Fourier Descriptor Layer 1, Histogram Energy Layer 1, Histogram Entropy Layer 1, Co-occurrence matrix features OF1 G1 CONTRAST Layer 1, Run-length features G1 D0 HGRE Layer 1, Run-length features G1 D0 LGRE Layer 1, Laws features E5 E5 Energy Layer 1, Laws features L5 S5 Energy Layer 1, Laws features R5 E5 Energy Layer 1, Wavelet decomposition P1 L3 C1 Layer 1, Wavelet decomposition P1 L3 C2 Layer 1, Border length (Pxl), Width (Pxl), and Radius of largest enclosed ellipse).

18. The method of embodiment 17, wherein the quantitative radiomic features comprise each of the radiomic features in Table 12 (Fourier Descriptor Layer 1, Histogram Energy Layer 1, Histogram Entropy Layer 1, Co-occurrence matrix features OF1 G1 CONTRAST Layer 1, Run-length features G1 D0 HGRE Layer 1, Run-length features G1 D0 LGRE Layer 1, Laws features E5 E5 Energy Layer 1, Laws features L5 S5 Energy Layer 1, Laws features R5 E5 Energy Layer 1, Wavelet decomposition P1 L3 C1 Layer 1, Wavelet decomposition P1 L3 C2 Layer 1, Border length (Pxl), Width (Pxl), and Radius of largest enclosed ellipse).

19. The method of any one of embodiments 10 to 18, wherein the comparing is done using principal component analysis (PCA), machine learning (e.g., random forest technique), or other statistical method.

20. The method of any one of embodiments 10 to 19, wherein the method provides a surrogate for distinguishing between high risk and low risk radiologic features, or between high risk stigmata and worrisome features.

21. The method of any one of embodiments 10 to 19, wherein the classifying comprises classifying the IPMN as benign IPMN or not benign (e.g., having malignant IPMN pathology).

22. A method for treating an intraductal papillary mucinous neoplasm (IPMN) in a subject, comprising administering a treatment to the subject, wherein the IPMN has previously been classified using the method of any one of embodiments 10 to 21.

23. The method of embodiment 22, wherein:
  (a) the IPMN is classified as benign (low risk) and the treatment comprises one or both of follow-up imaging (e.g., MM and/or CT), and endoscopic ultrasound with or without fine needle aspiration; or
  (b) the IPMN is classified as not benign (e.g., high risk or having malignant IPMN pathology) and the treatment comprises administering one or more of: a surgical intervention, radiation therapy, or anti-cancer agent (e.g., chemotherapy, immunotherapy, etc.).

24. The method of embodiment 23, wherein the treatment of (b) comprises surgical resection.

25. A method for treating an intraductal papillary mucinous neoplasm (IPMN) in a subject, comprising carrying out the method of any one of embodiments 10 to 21, and administering a treatment to the subject.

26. The method of embodiment 25, wherein:
  (a) the IPMN is classified as benign (low risk) and the treatment comprises one or both of follow-up imaging (e.g., MM and/or CT), and endoscopic ultrasound with or without fine needle aspiration; or
  (b) the IPMN is classified as not benign (e.g., high risk or having malignant IPMN pathology) and the treatment comprises administering one or more of: a surgical intervention, radiation therapy, or anti-cancer agent (e.g., chemotherapy, immunotherapy, etc.).

27. The method of embodiment 26, wherein the treatment of (b) comprises surgical resection.

28. A method for detecting messenger RNA (mRNA) in human blood, comprising:
detecting the level of one or more mRNAs (e.g., 1, 2, 3, 4, or more) in a human blood sample selected from among: gastrokine 2 (GKN2), cluster of differentiation 19 (CD19), breast cancer 1 (BRCA1), and transforming protein p21 (HRAS).

29. The method of embodiment 28, wherein the human blood sample is a sample of whole blood, serum, or plasma.

30. The method of embodiment 28 or 29, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

31. A method of assessing whether a human subject has an intraductal papillary mucinous neoplasm (IPMN), comprising:
detecting the level of one or more mRNAs (e.g., 1, 2, 3, 4, or more) in a blood sample from the subject selected from among: gastrokine 2 (GKN2), cluster of differentiation 19 (CD19), breast cancer 1 (BRCA1), and transforming protein p21 (HRAS); comparing the detected level with a reference level; and classifying the blood sample as indicating the presence of an IPMN or the absence of an IPMN (or normal pancreatic (duct) tissue) based on the results of the comparing step.

32. The method of embodiment 31, wherein the human blood sample is a sample of whole blood, serum, or plasma.

33. The method of embodiment 31 or 32, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

34. A method for treating an intraductal papillary mucinous neoplasm (IPMN) in a subject, comprising administering a treatment for the IPMN to the subject, wherein the subject has previously been identified as having the IPMN using the method of 28 or 31.

35. A method for treating an intraductal papillary mucinous neoplasm (IPMN) in a subject, comprising carrying out the method of any one of embodiments 26 or 29, and administering a treatment for the IPMN to the subject.

36. A method for detecting messenger RNA (mRNA) in human blood, comprising:
detecting the level of one or more mRNAs (e.g., 1, 2, 3, 4, 5, 6, 7, 8, 9, or more) in a human blood sample selected from among: breast cancer 1 (BRCA1), C-X-C motif chemokine ligand 17 (CXCL17), estrogen receptor 1 (ESR1), fibroblast growth factor receptor 3 (FGFR3), Gem-associated protein 4 (GEMIN4), MutS homolog 6 (MSH6), Myc proto-oncogene protein (MYC), peroxisome proliferator-activator receptor gamma (PPARG), and Wnt family member 1 (WNT1).

37. The method of embodiment 36, wherein the human blood sample is a sample of whole blood, serum, or plasma.

38. The method of embodiment 36 or 37, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

39. A method for distinguishing between indolent/benign and aggressive/malignant intraductal papillary mucinous neoplasms (IPMNs), comprising:
detecting the level of one or more mRNAs (e.g., 1, 2, 3, 4, 5, 6, 7, 8, 9, or more) in a blood sample from the subject selected from among: breast cancer 1 (BRCA1), C-X-C motif chemokine ligand 17 (CXCL17), estrogen receptor 1 (ESR1), fibroblast growth factor receptor 3 (FGFR3), Gem-associated protein 4 (GEMIN4), MutS homolog 6 (MSH6), Myc proto-oncogene protein (MYC), peroxisome proliferator-activator receptor gamma (PPARG), and Wnt family member 1 (WNT1); comparing the detected level with a reference level; and classifying the blood sample as indicating indolent or benign IPMN or aggressive or malignant, based on the results of the comparing step.

40. The method of embodiment 39, wherein the human blood sample is a sample of whole blood, serum, or plasma.

41. The method of embodiment 39 or 40, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

42. A method for treating an intraductal papillary mucinous neoplasm (IPMN) in a subject, comprising administering a treatment for the IPMN to the subject, wherein the subject has previously been identified as having the IPMN using the method of any one of embodiments 39 or 39.

43. A method for treating an intraductal papillary mucinous neoplasm (IPMN) in a subject, comprising carrying out the method of embodiment 37 or 38, and administering a treatment for the IPMN to the subject.

44. A method of assessing the severity or potential pathology of a intraductal papillary mucinous neoplasm (IPMN) in a human subject, comprising:
obtaining a quantitative radiological measure of abdominal/visceral obesity in the subject; comparing the obtained quantitative radiological measure of abdominal/visceral obesity with a reference radiological measure of abdominal/visceral obesity; and classifying the severity and/or predicted pathology of the IPMN based on the results of the comparing step.

45. The method of embodiment 44, wherein the radiological measure comprises one or more of total abdominal fat (TAF) area, visceral fat area (VFA), subcutaneous fat (SFA), and visceral to subcutaneous fat ratio (V/S).

46. The method of embodiment 44 or 45, wherein the radiological measure is obtained by computed tomography (CT) scan or magnetic resonance imaging (MRI).

47. A method for treating an intraductal papillary mucinous neoplasm (IPMN) in a subject, comprising administering a treatment for the IPMN to the subject, wherein the IPMN has been previously assessed using the method of embodiment 44 or 45.

48. A method for treating an intraductal papillary mucinous neoplasm (IPMN) in a subject, comprising carrying out the method of embodiment 42 or 43, and administering a treatment for the IPMN to the subject.

49. A method for detecting long non-coding RNAs in human blood, comprising:
detecting the level of one or more long non-coding RNAs (lncRNAs) (e.g., 1, 2, 3, 4, 5, 6, 7, 8, 9, 10, or more) in a human blood sample selected from among: GAS5, SRA, ADARB2-AS1, ANRIL, GLIS3-AS1, LINC00472, MEG3, PANDA, PVT1, and UCA1.

50. The method of embodiment 49, wherein the human blood sample is a sample of whole blood, serum, or plasma.

51. The method of embodiment 49 or 50, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

52. A method of assessing whether a human subject has an intraductal papillary mucinous neoplasm (IPMN), comprising:
   detecting the level of one or both long non-coding RNAs (lncRNAs) in a human blood sample selected from among: GAS5, and SRA; comparing the detected level with a reference level; and classifying the blood sample as indicating the presence of an IPMN or the absence of an IPMN (or normal pancreatic (duct) tissue) based on the results of the comparing step.

53. The method of embodiment 52, wherein the human blood sample is a sample of whole blood, serum, or plasma.

54. The method of embodiment 52 or 53, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

55. A method of assessing the severity or potential pathology of a intraductal papillary mucinous neoplasm (IPMN) in a human subject, comprising:
   detecting the level of one or more one or more long non-coding RNAs (lncRNAs) (e.g., 1, 2, 3, 4, 5, 6, 7, 8 or more) in a human blood sample selected from among: ADARB2-AS1, ANRIL, GLIS3-AS1, LINC00472, MEG3, PANDA, PVT1, and UCA1;
   comparing the detected level with a reference level; and
   classifying the severity or potential pathology of the IPMN based on the results of the comparing step.

56. The method of embodiment 55, wherein the human blood sample is a sample of whole blood, serum, or plasma.

57. The method of embodiment 54 or 55, wherein said detecting is carried out by Northern blot analysis, nuclease protection assay (NPA), microarray hybridization assay or other hybridization assay (e.g., NanoString assay), and polymerase chain reaction (e.g., reverse transcription-polymerase chain reaction (RT-PCR)).

58. A method for treating an intraductal papillary mucinous neoplasm (IPMN) in a subject, comprising administering a treatment for the IPMN to the subject, wherein the subject has previously been identified as having the IPMN using the method of any one of embodiments 49 to 57.

59. A method for treating an intraductal papillary mucinous neoplasm (IPMN) in a subject, comprising carrying out the method of any one of embodiments 49 to 57, and administering a treatment for the IPMN to the subject.

In the treatments methods of the invention, including those in the above Exemplified Embodiments, the treatment may be, for example, surgery (e.g., resection), radiation, administration of one or more anti-cancer agents such as a chemotherapuetics to the subject, or a combination of two or more of the foregoing.

In the methods of treatment of the invention, including those in the above Exemplified Embodiments, further examples of treatment include, but are not limited to:
Surgeries (Surgical Interventions):
   Enucleation (removing just the tumor): If a pancreatic neuroendocrine tumor is small, just the tumor itself is removed. This is called enucleation.

Whipple procedure (pancreaticoduodenectomy): removing the head of the pancreas and sometimes the body of the pancreas as well. Nearby structures such as part of the small intestine, part of the bile duct, the gallbladder, lymph nodes near the pancreas, and sometimes part of the stomach are also removed.

Distal pancreatectomy: removing only the tail of the pancreas or the tail and a portion of the body of the pancreas.

Total pancreatectomy: removing the entire pancreas, as well as the gallbladder, part of the stomach and small intestine, and the spleen.

Palliative surgery: If the cancer has spread too far to be removed completely, any surgery being considered would be palliative (intended to relieve or prevent symptoms).

Ablative Treatments:
   Ablation refers to treatments that destroy tumors, usually with extreme heat or cold.

Radiofrequency ablation (RFA): Using high-energy radio waves for treatment. A thin, needle-like probe is placed through the skin and into the tumor. An electric current then passes through the tip of the probe, which heats the tumor and destroys the cancer cells. This treatment is used mainly for small tumors.

Microwave thermotherapy: This procedure is similar to RFA, except microwaves are used to heat and destroy the tumor.

Cryosurgery (also known as cryotherapy or cryoablation): Destroying a tumor by freezing it. A thin metal probe is guided into the tumor, and very cold gasses pass through the probe to freeze the tumor, killing the cancer cells.

Embolization: Embolization involves injecting substances into an artery to try to block the blood flow to cancer cells, causing them to die.

Arterial embolization: This is also known as trans-arterial embolization (or TAE). A catheter (a thin, flexible tube) is put into an artery through a small cut in the inner thigh and threaded up into the artery feeding the tumor and small particles are injected into the artery to plug it up.

Chemoembolization: This is also known as trans-arterial chemoembolization (or TACE), which combines embolization with chemotherapy. This involves using tiny beads that give off a chemotherapy drug for the embolization. TACE can also be done by giving chemotherapy through the catheter directly into the artery, then plugging up the artery.

Radioembolization: This combines embolization with radiation therapy. This involves injecting small radioactive beads (called microspheres) into the artery. The beads lodge in the blood vessels near the tumor, where they give off small amounts of radiation to the tumor site for several days. The radiation travels a very short distance, so its effects are limited mainly to the tumor.

Anti-Cancer Agents Such as Drugs:
   Abraxane (Paclitaxel Albumin-stabilized Nanoparticle Formulation)
   Afinitor (Everolimus)
   Erlotinib Hydrochloride
   Everolimus
   Fluorouracil Injection
   Gemcitabine Hydrochloride
   Mitomycin C
   Mitozytrex (Mitomycin C)
   Mutamycin (Mitomycin C)
   Sunitinib Malate
   Sutent (Sunitinib Malate)
   Lanreotide Acetate
   Lutathera (Lutetium Lu 177-Dotatate)
   Lutetium Lu 177-Dotatate Somatuline Depot (Lanreotide Acetate)

Folfirinox: FOL=Leucovorin Calcium (Folinic Acid); F=Fluorouracil; IRIN=Irinotecan Hydrochloride; OX=Oxaliplatin (this is different from what you identified below)

Gemcitabine Hydrochloride and Cisplatin

Gemcitabine Hydrochloride and Oxaliplatin

OFF: O=Oxaliplatin; F=Fluorouracil; and F=Leucovorin Calcium (Folinic Acid)

Examples of chemotherapeutic treatments include, but are not limited to: erlotinib, Gemcitabine (Gemzar), 5-fluorouracil (5-FU), Irinotecan (Camptosar), Oxaliplatin (Eloxatin), Albumin-bound paclitaxel (Abraxane), Capecitabine (Xeloda), Cisplatin, Paclitaxel (Taxol), Docetaxel (Taxotere), and Irinotecan liposome (Onivyde). Examples of combination treatments include: a combination of Albumin-bound paclitaxel and gemcitabine; combination of Irinotecan liposome, 5-FU, and folinic acid (leucovorin); and combination of 5-FU, irinotecan and oxaliplatin (Folfirinox).

Other examples of anti-cancer agents that can be used as monotherapy or combination treatments are listed in Table 20.

The treatment may include a dendritic cell (DC) vaccine, or chimeric antigen receptor T-cell therapy (CAR T-cell therapy).

The treatment may include an anti-cancer agent, such as a chemotherapeutic or immunotherapy, in combination with a checkpoint inhibitor, such as Tremelimumab, Nivolumab, Ipilimumab, Pembrolizumab, Anti-PD-L1 Checkpoint Antibody (LY3300054), Galunisertib (LY2157299), and Durvalumab (MEDI4736).

Radiogenic Approach to Classify Pancreatic Cancer Precursors

IPMNs are cystic pancreatic cancer precursors increasingly being detected incidentally by imaging. The only way to treat IPMNs and examine severity (which ranges from low- and moderate-grade dysplasia to high-grade dysplasia and invasive carcinoma) is through surgical resection and pathological evaluation. Noninvasive approaches are needed to differentiate "benign" IPMNs that can be monitored from "malignant" IPMNs that warrant surgery. The inventors previously identified a plasma-based miRNA genomic classifier (MGC) that included miR-200a-3p, miR-1185-5p, miR-33a-5p, miR-574-4p, and miR-664b (SEQ ID Nos:45-49) and discriminated malignant from benign IPMNs (p=0.005).

"Radiomics" refers to transformation of medical images into mineable quantitative data that can be used to predict clinical outcomes. To date, a radiomic approach has not been used to predict IPMN pathology. The inventors endeavored to determine whether quantitative radiomic features extracted from preoperative computed tomography (CT) scans may more accurately predict IPMN pathology than standard radiologic features, when considered individually or in combination with the MGC.

As described in Example 4, preoperative CT images were obtained for a retrospective cohort of 38 surgically-resected, pathologically-confirmed IPMN cases (20 benign; 18 malignant) with matched preoperative MGC data. Images were reviewed for standard radiologic features characterized to be "high-risk" or "worrisome" for malignancy according to consensus guidelines. The region of interest in the pancreas was identified and segmented using a semi-automated algorithm (FIG. 8).

A total of 112 two-dimensional (2D) quantitative non-texture and texture features were extracted. Logistic regression models were used to explore associations between non-redundant radiomic features and IPMN pathology. Principal component analysis was performed to generate an index score (that was evaluated for its association with malignant pathology. Sensitivity, specificity, positive predictive value (PPV), negative predictive value (NPV), and accuracy of the radiomic features individually and in combination with the MGC were estimated.

Selected clinical and pathologic characteristics of the 38 cases (20 benign; 18 malignant) having matched pre-operative CT and MGC data are in Table 11.

Figure 9:
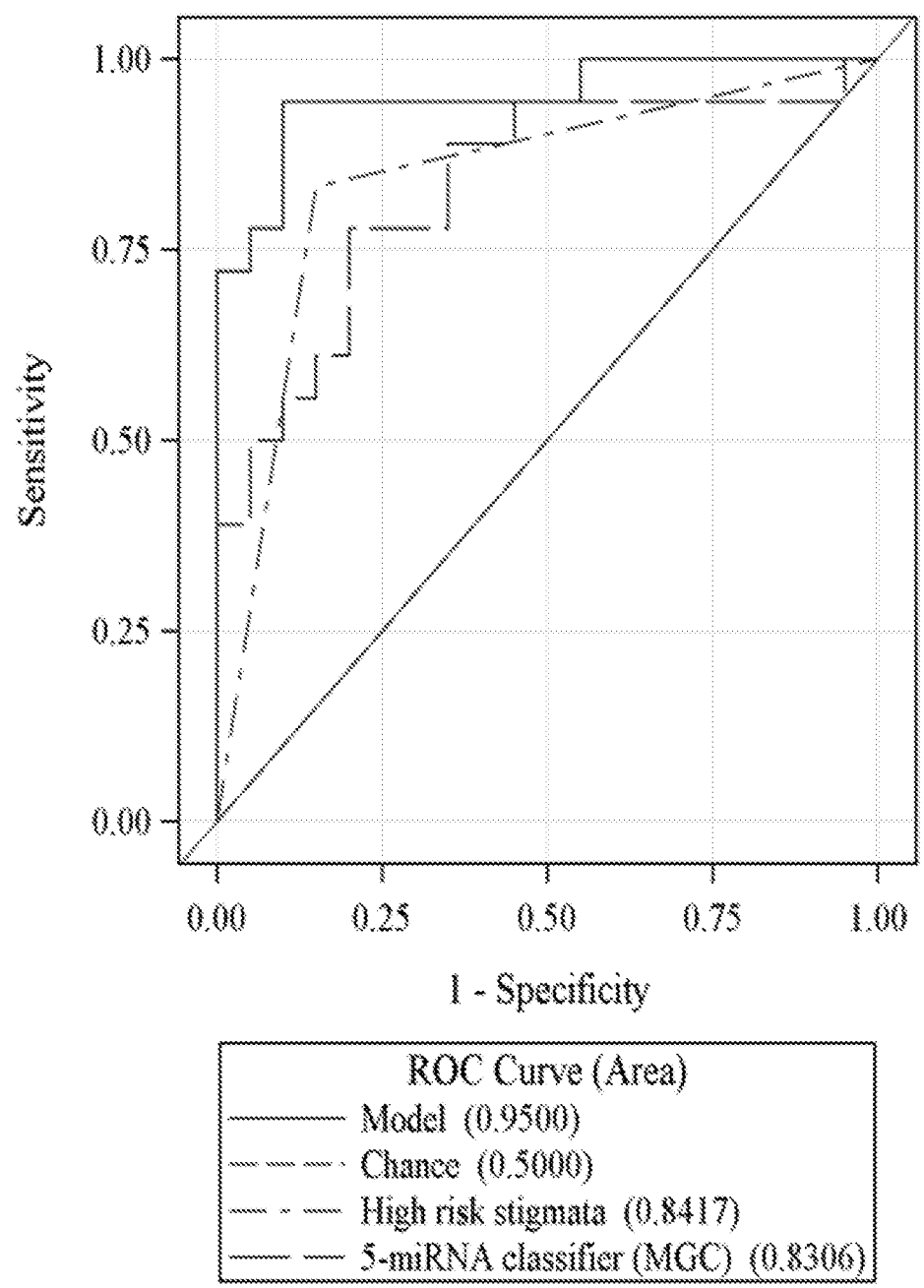
FIG. 9. A model that combines the 5 miRNA genomic classifier signature (MGC) with high risk stigmata is more accurate in predicting IPMN malignancy than either variable alone.
Figure 10:
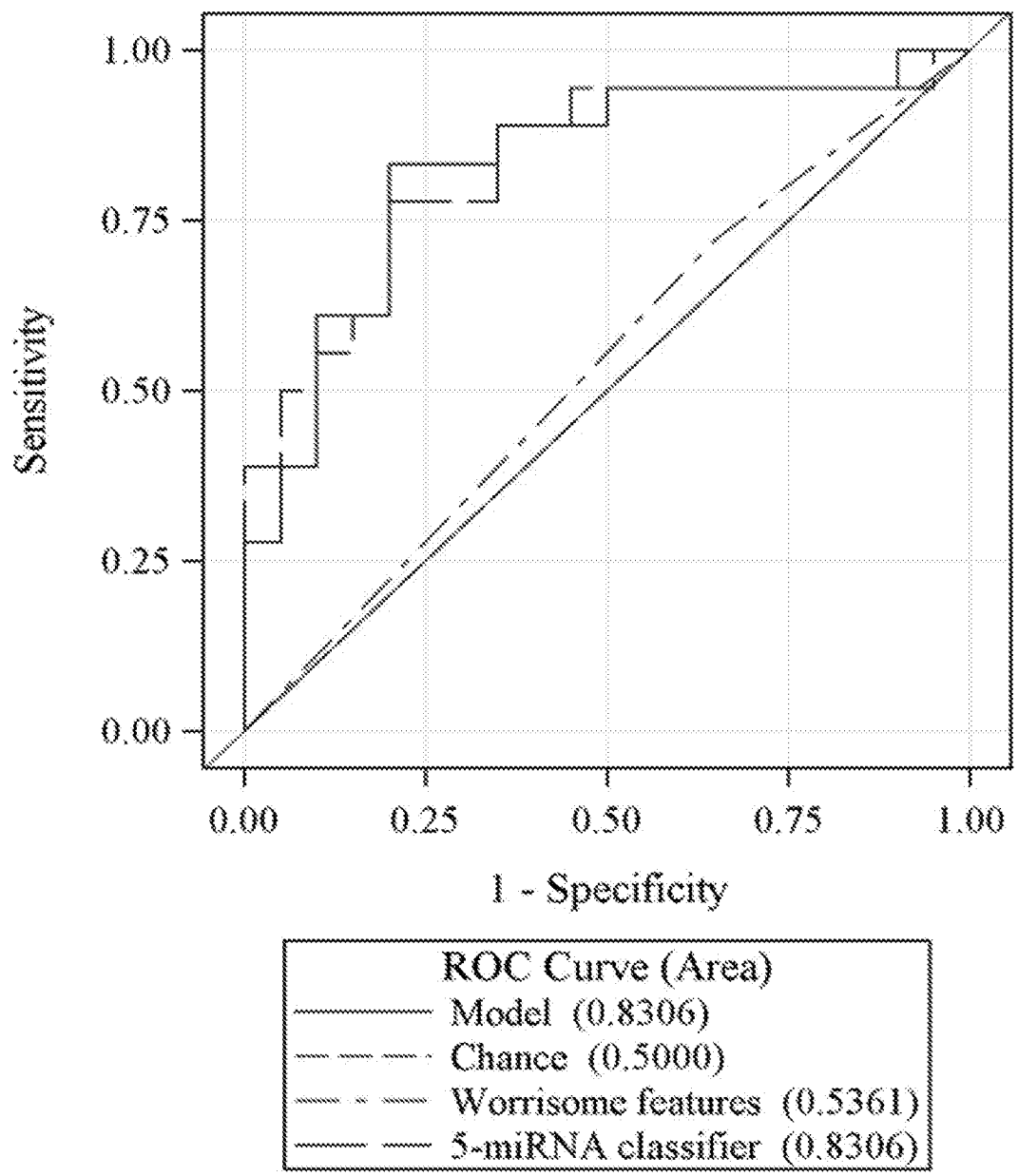
FIG. 10. Worrisome features performed poorly compared to the miRNA genomic classifier signature.

Multiple logistic regression analyses revealed that only high risk stigmata and the MGC retained significance (OR (95% CI): 43.0 (4.64-398), p=0.001 and OR (95% CI): 0.30 (0.10-0.86), p=0.026, respectively. The area underneath the curve (AUC) value was 0.95 for the model with both variables, compared to 0.84 and 0.83 for high risk stigmata and the MGC individually (FIG. 9). Worrisome features alone could not predict malignant pathology much better than chance (AUC=0.54); the AUC increased to 0.83 when incorporating the MGC (FIG. 10). A model that solely considered demographic characteristics and clinical predictors of IPMN pathology (age at diagnosis, gender, presence of symptoms) had an AUC (95% CI)=0.73 (0.56-0.89).

Figure 8A:
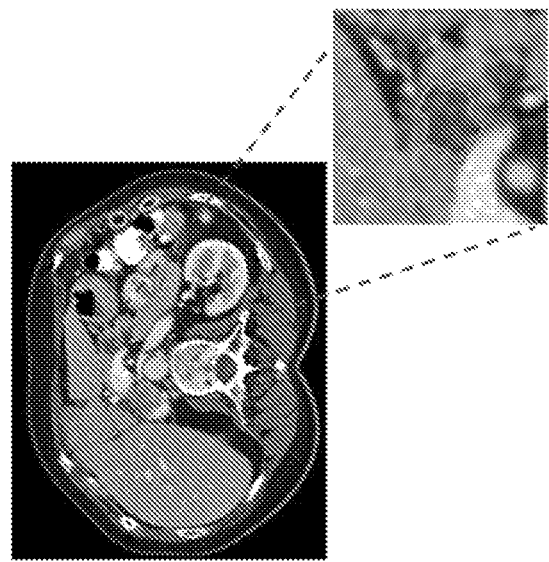
FIGS. 8A-8B. Semi-automated segmentation of two IPMN patient CT scans at the selected central slice.
Figure 8B:
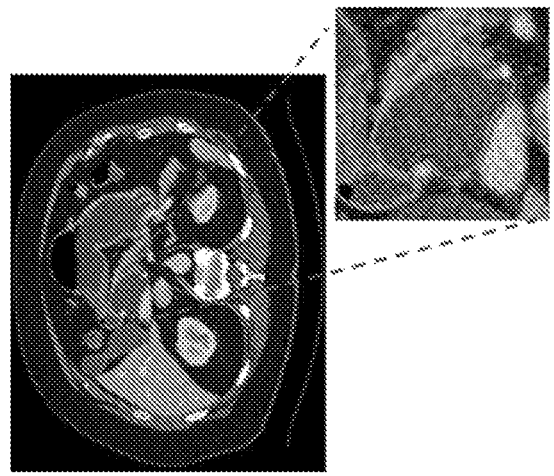
Figure 11:
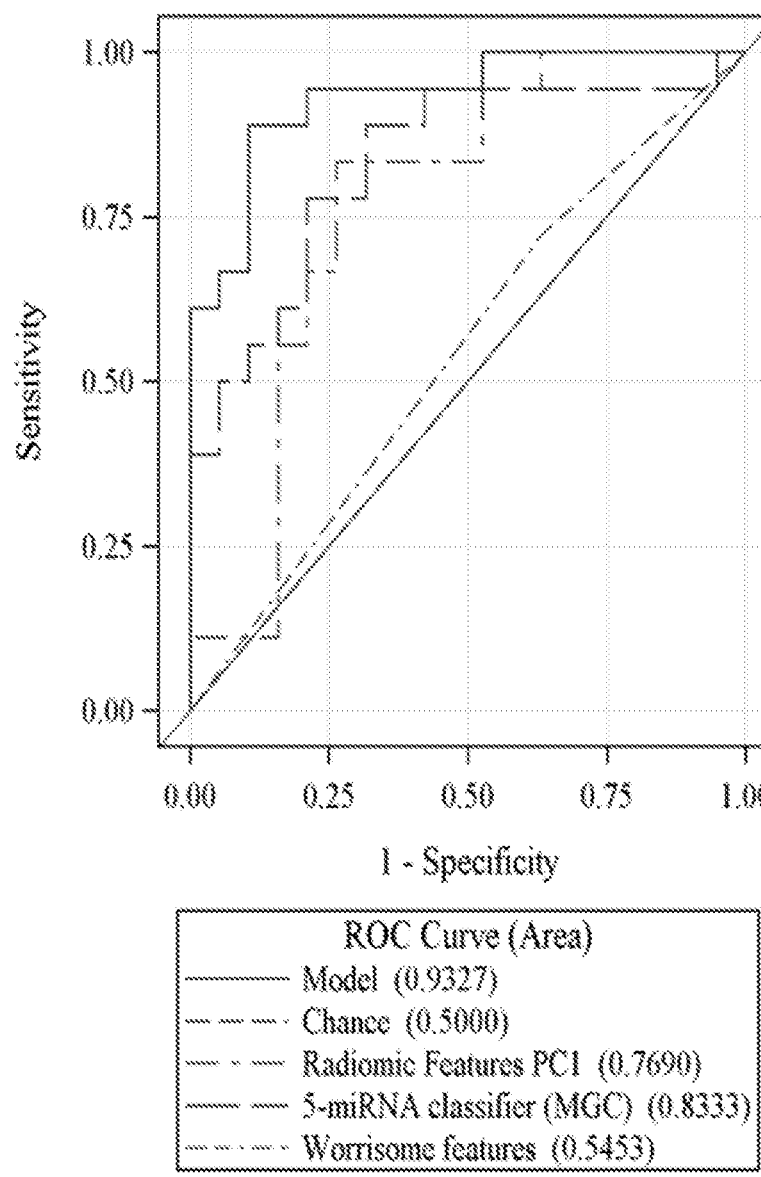
FIG. 11. ROC analysis suggests that a model combining radiomic features (PC1) with the 5-miRNA genomic classifier (MGC) is more accurate at predicting malignant IPMN pathology than either variable alone and is substantially more accurate for prediction than worrisome radiologic features. Moreover, a final model combining worrisome features, radiomic features, and the MGC has potential to have high accuracy, with an AUC value approximating 0.93.

Analysis of 112 extracted radiomic CT features revealed 14 textural and non-textural features that differentiated malignant from benign IPMNs (P<0.05) (Table 12). Collectively, the 14 radiomic features had an AUC=0.77. Radiomic features may help to minimize over- and under treatment (FIGS. 8A and 8B). A model combining radiomic features and the MGC had an AUC=0.92, and an AUC=0.93 when incorporating worrisome features (FIG. 11). Diagnostic performance of models including radiomic and MGC data was superior to other models (Table 13).

Incorporating radiomic and miRNA expression data from images and blood obtained through the standard of care can facilitate a noninvasive multimodal approach to rapidly and cost-effectively provide information to improve pre-operative prediction of IPMN pathology.

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1—Plasma RNAs as Biomarkers of Pre-Malignant Pancreatic Cysts

Pancreatic ductal adenocarcinoma (PDAC) is known for its aggressive behavior and lack of effective biomarkers to detect disease early. Circulating RNAs have been shown to be released by tumor cells into the bloodstream, to resist RNases, and be stably present at sufficient levels for molecular analyses. Studies of candidate circulating messenger RNAs (mRNAs) have previously performed using blood from PDAC cases, typically using labor-intensive RT-PCR approaches.

The inventors hypothesized that mRNAs may be shed from pancreas tissue into circulation and serve as diagnostic markers of early PDAC characterized by commonly-detected PDAC precursors known as intraductal papillary mucinous neoplasms (IPMNs). The inventors endeavored to simultaneously measure the abundance in plasma of >100 candidate mRNAs and: 1) discover mRNAs that distinguish IPMN cases from healthy controls; 2) identify mRNAs that differentiate "aggressive/malignant" IPMNs that warrant surgical removal from "indolent/benign" IPMNs that can be watched; and 3) determine the performance of mRNAs in predicting IPMN pathology individually and in combination with other data types (Permuth-Wey et al., 2015; Permuth et al., 2016).

smoked cigarettes than controls (36%). The distribution of low-, moderate-, high-grade, and invasive IPMN cases was 12%, 29%, 24%, and 35%, respectively. Selected characteristics of the IPMN cohort are summarized in Table 1.

TABLE 1

Characteristics of study participants.

| Variable | Benign[1] IPMNs (n = 21) | Malignant[2] IPMNs (n = 30) | pvalue |
|---|---|---|---|
| Age at diagnosis, mean (SD)(yrs) | 68.4 (9.8) | 68.6 (10.3) | 0.939 |
| Male:Female, n (%) | 8(38):13(62) | 19(63):11(37) | 0.075 |
| Body mass index (BMI), mean (SD) | 26.5 (4.6) | 27.9 (4.6) | 0.355 |
| Positive personal history of diabetes | 4 (19) | 4 (13) | 0.621 |
| Positive personal history of chronic pancreatitis | 5 (24) | 9 (30) | 0.126 |
| Had abdominal pain as presenting symptom | 7 (37) | 11 (37) | 0.165 |
| Had weight loss as presenting symptom | 3 (14) | 8 (27) | 0.110 |
| Had jaundice as presenting symptom | 1 (5) | 8 (27) | 0.012 |
| Pre-operative serum CA 19-9 levels, mean (SD)(ng/mL) | 91 (314) | 692 (1493) | 0.125 |
| Pre-operative serum albumin levels, mean (SD)(ng/mL) | 4.4 (0.98) | 3.9 (0.66) | 0.073 |
| Predominant tumor location | | | 0.013 |
| Pancreatic Head | 6 (29) | 14 (47) | |
| Pancreatic Body or Tail | 14 (67) | 12 (40) | |
| Diffuse | 1 (5) | 4 (13) | |
| Type of ductal communication | | | 0.003 |
| Main duct or mixed | 4 (22) | 10 (30) | |
| Branch duct | 14 (78) | 4 (13) | |
| Size of largest cyst on imaging, mean (range) (cm) | 2.8 (1.6) | 3.5 (1.4) | 0.145 |
| Solid component or mural nodule | | | 0.021 |
| Yes | 3 (14) | 8 (27) | |
| No | 15 (71) | 6 (20) | |

Data represent counts (percentages) unless otherwise indicated. Counts may not add up to the total due to missing values, and percentages may not equal 100 due to rounding.
[1]Benign IPMNs are represented by 6 low-grade and 15 moderate-grade IPMNs.
[2]Malignant IPMNs are represented by 12 high-grade and 18 invasive IPMNs.

Materials & Methods

In a retrospective cohort of 57 surgically-resected, pathologically-confirmed IPMN cases and 24 age- and gender-matched non-diseased controls from Moffitt Cancer Center, a Nanostring NCOUNTER™ custom codeset was used to evaluate archived pre-operative plasma for 117 candidate mRNAs identified from literature and previous studies (Permuth-Wey et al., 2015; Permuth-Wey et al., 2016).

Linear models for microarray and principal component analyses were used to identify mRNAs that differentiated between groups. Multivariable logistic regression analysis was used to assess whether mRNAs were associated with IPMN pathology independent of standard clinical and radiologic features "high-risk" or "worrisome" for malignancy. Diagnostic performance was estimated using receiver operating characteristic curve analysis.

Results

Eight samples were excluded (due to failed quality control) prior to normalization and statistical analysis, leaving samples from 73 participants (51 cases, 22 controls) for analysis. Cases and controls were well-matched on age (mean age: 68.5 vs 68.2 years). Most subjects were white, non-Hispanic. IPMN cases were more likely (47%) to have The data represent counts (percentages) unless otherwise indicated. Counts may not add up to the total due to missing values, and percentages may not equal 100 due to rounding. Benign IPMNs are represented by 6-low grade and 15 moderate-grade IPMNs. Malignant IPMNs are represented by 12 high-grade and 18 invasive IPMNs.

Four mRNAs differentiated IPMN cases from controls (P<0.05) (see Table 2).

TABLE 2

Genes differentially expressed (P < 0.05) in IPMN cases (n = 51) versus controls (n = 22).

| Gene | Overall mean | Case mean | Control mean | P. value | Adj. P. Val | FoldChange |
|---|---|---|---|---|---|---|
| GKN2 | 1.51 | 1.08 | 2.50 | 0.013 | 0.890 | 0.433 |
| CD19 | 7.83 | 7.37 | 8.87 | 0.023 | 0.890 | 0.831 |
| BRCA1 | 3.03 | 3.67 | 1.55 | 0.043 | 0.890 | 2.374 |
| HRAS | 7.29 | 7.74 | 6.24 | 0.047 | 0.890 | 1.240 |

Nine mRNAs differentiated between benign and malignant IPMNs (P<0.05) (FIG. 1).

Figure 2A:
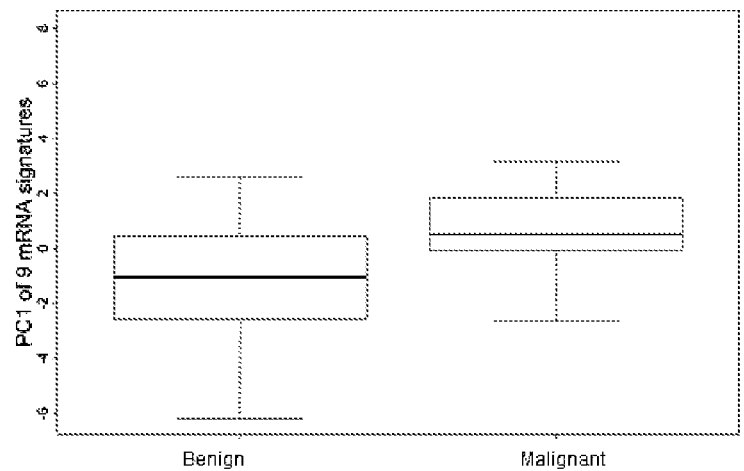
FIGS. 2A-B. The 9-mRNA signature associates with IPMN pathology.
Figure 2B:
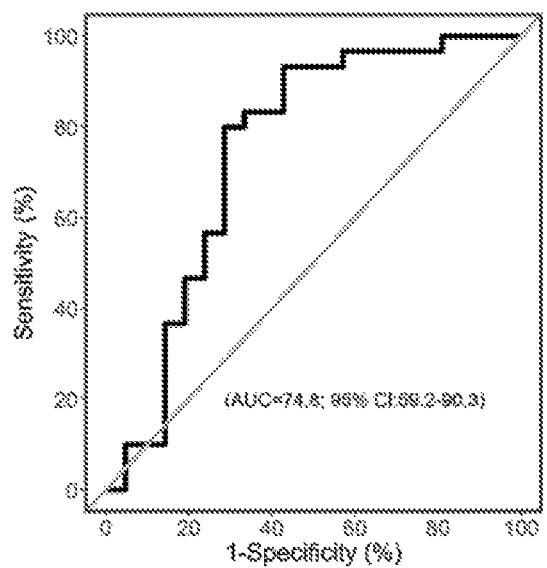

A 9-mRNA signature characterized by the first principal component had an AUC of 0.748 (95% CI: 59.2-90.3) in differentiating malignant from benign IPMNs, which was superior to "worrisome" radiologic features (FIGS. 2A-B).

Figure 3:
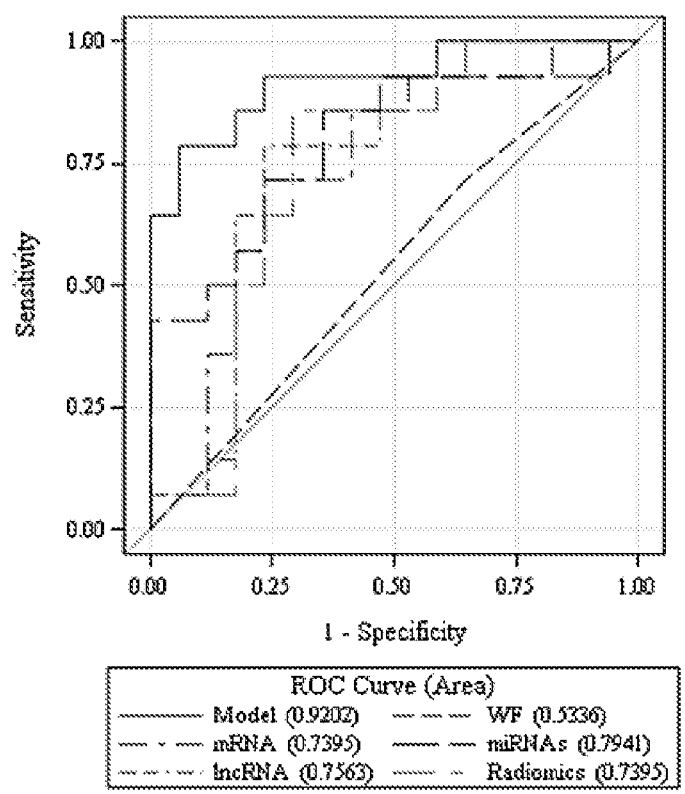
FIG. 3. ROC analysis suggests that genomic data (the 9-mRNA signature, a 5-miRNA signature, and an 8-lncRNA signature) and quantitative "radiomic" features are more accurate in predicting malignant IPMN pathology than standard worrisome radiologic features. A final model combining the genomic data with radiomic features and standard worrisome features (WF) has potential to have high accuracy in predicting malignant pathology, with an AUC value approximating 0.92.
Figure 4A:
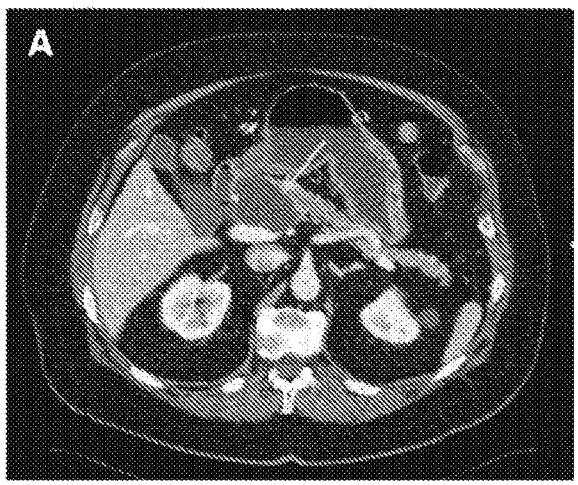
FIGS. 4A-4D. Axial post contrast CTs (FIG. 4A and FIG. 4B) and quantitative segmentation (FIG. 4C and FIG. 4D) for two representative side BD IPMN cases with main pancreatic ducts normal in caliber. Case 1 has a well-demarcated homogenous hypodense 4.8 cm cystic lesion in the pancreatic neck (yellow arrow). The cystic lesion abuts the gastroduodenal artery (red arrow) without definite encasement. Case 2 has a poorly defined 1.3 cm hypoenhancing pancreatic neck lesion (yellow arrow).
Figure 4B:
Figure 4C:
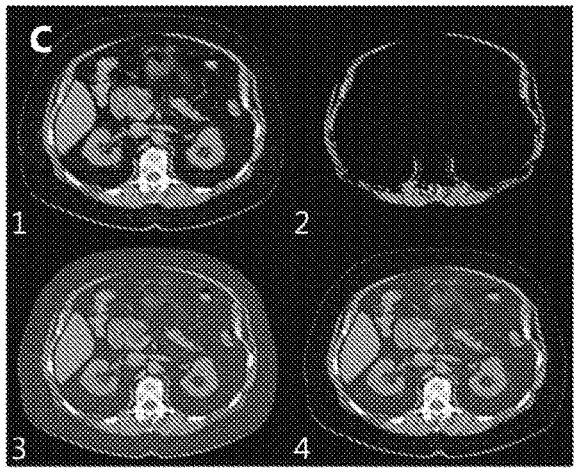
Figure 4D:
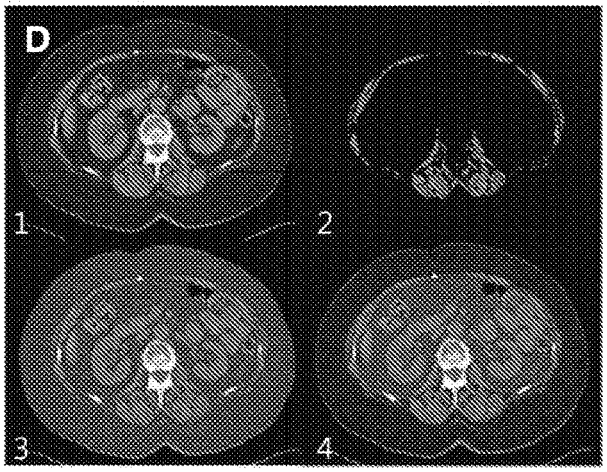

When combining a 5-microRNA (miRNA) signature (Permuth-Wey et al., 2015), a 14-feature quantitative "radiomic" imaging signature (Permuth et al., 2016), and an 8-long non-coding RNA (lncRNA) signature (Permuth et al., under review) for 31 cases (14 malignant, 17 benign), the AUC increased to 0.92, with a sensitivity, specificity, and positive and negative predictive value of 79%, 94%, 92%, and 84% (Table 3; FIG. 3).

TABLE 3

Diagnostic performance of preliminary models to predict malignant IPMNs[1]

| Model/Variables included | AUC (95% CI) | p value | FDR | Accuracy | SE | SP | PPV | NPV |
|---|---|---|---|---|---|---|---|---|
| Gender | 0.60 (0.43-0.78) | 0.242 | 0.255 | 0.61 | 0.50 | 0.71 | 0.58 | 0.63 |
| Jaundice | 0.61 (0.48-0.75) | 0.087 | 0.104 | 0.65 | 0.29 | 0.94 | 0.80 | 0.62 |
| High risk stigmata (HRS) | 0.84 (0.71-0.97) | <0.0001 | 0.003 | 0.84 | 0.86 | 0.82 | 0.80 | 0.88 |
| Worrisome features (WF) | 0.53 (0.36-0.70) | 0.690 | 0.690 | 0.52 | 0.71 | 0.35 | 0.48 | 0.60 |
| mRNA signature | 0.74 (0.56-0.92) | 0.018 | 0.036 | 0.74 | 0.71 | 0.76 | 0.71 | 0.76 |
| miRNA signature | 0.79 (0.63-0.96) | 0.035 | 0.053 | 0.74 | 0.86 | 0.65 | 0.67 | 0.85 |
| lncRNA signature | 0.76 (0.58-0.94) | 0.012 | 0.033 | 0.77 | 0.79 | 0.76 | 0.73 | 0.81 |
| mRNA + miRNA | 0.86 (0.70-1.00) | 0.019 | 0.036 | 0.84 | 0.86 | 0.82 | 0.80 | 0.88 |
| mRNA + lncRNA | 0.79 (0.62-0.95) | 0.036 | 0.053 | 0.77 | 0.79 | 0.76 | 0.73 | 0.81 |
| mRNA s+ miRNAs + lncRNAs | 0.84 (0.69-1.00) | 0.033 | 0.053 | 0.84 | 0.79 | 0.88 | 0.85 | 0.83 |
| Radiomics signature | 0.74 (0.55-0.93) | 0.014 | 0.033 | 0.77 | 0.86 | 0.71 | 0.71 | 0.86 |
| mRNA+Radiomics | 0.81 (0.66-0.96) | 0.010 | 0.033 | 0.77 | 0.71 | 0.82 | 0.77 | 0.78 |
| mRNA + miRNA + lncRNA + Radiomics | 0.91 (0.80-1.00) | 0.009 | 0.033 | 0.87 | 0.71 | 1.00 | 1.00 | 0.81 |
| WF + mRNAs | 0.74 (0.56-0.93) | 0.060 | 0.076 | 0.74 | 0.71 | 0.76 | 0.71 | 0.76 |
| HRS + WF + mRNAs | 0.93 (0.85-1.00) | 0.001 | 0.006 | 0.87 | 0.86 | 0.88 | 0.86 | 0.88 |
| WF + mRNAs + Radiomics | 0.85 (0.72-0.99) | 0.010 | 0.033 | 0.84 | 0.86 | 0.82 | 0.80 | 0.88 |
| WF + mRNAs + miRNAs + lncRNAs | 0.85 (0.69-1.00) | 0.060 | 0.076 | 0.84 | 0.86 | 0.82 | 0.80 | 0.88 |
| WF + mRNAs + miRNAs + lncRNAs + Radiomics | 0.92 (0.82-1.00) | 0.013 | 0.033 | 0.87 | 0.79 | 0.94 | 0.92 | 0.84 |

[1]31 IPMN cases (17 benign; 14 malignant) had data types (clinical data, mRNA, miRNA radiomic, lncRNA) included in these analyses.
AUC = area underneath the curve; FDR = false discovery rate; SE = sensitivity; SP = specificity; PPV = positive predictive value; NPV = negative predictive value; High risk stigmata = main pancreatic duct involvement/dilation > 10 mm, obstructive jaundice with a cystic lesion in pancreatic head, or an enhanced solid component/nodule within the cyst; Worrisome features = main pancreatic duct dilation 5-9 mm, cyst size > 3 cm, thickened enhanced cyst walls, non-enhanced mural nodules, or acute pancreatitis.

These results support the use of these markers in an RNA-based blood test as a diagnostic adjunct for predicting IPMN pathology.

REFERENCES

1. Permuth-Wey J, et al., "Plasma MicroRNAs as Novel Biomarkers for Patients with Intraductal Papillary Mucinous Neoplasms of the Pancreas. Cancer Prev Res (Phila). 2015 September; 8(9):826-34.
2. Permuth J B, Choi J, Balarunathan Y, Kim J, Chen D T, Chen L, Orcutt S, Doepker M P, Gage K, Zhang G, Latifi K, Hoffe S, Jiang K, Coppola D, Centeno B A, Magliocco A, Li Q, Trevino J, Merchant N, Gillies R, Malafa M, On Behalf Of The Florida Pancreas Collaborative. Combining radiomic features with a miRNA classifier may improve prediction of malignant pathology for pancreatic intraductal papillary mucinous neoplasms. Oncotarget. 2016 Dec. 27; 7(52):85785-85797.

Example 2—Radiologic Measures of Abdominal Adiposity as Diagnostic Markers of IPMN Severity/Pathology Intra-abdominal fat is a risk factor for pancreatic cancer (PC), but little is known about its contribution to PC precursors known as intraductal papillary mucinous neoplasms (IPMNs). Our goal was to evaluate quantitative radiologic measures of abdominal/visceral obesity as possible diagnostic markers of IPMN severity/pathology.

In a cohort of 34 surgically-resected, pathologically-confirmed IPMNs (17 benign; 17 malignant) with preoperative abdominal computed tomography (CT) images, the inventors calculated body mass index (BMI) and four radiologic measures of obesity: total abdominal fat (TAF) area, visceral fat area (VFA), subcutaneous fat area (SFA), and visceral to subcutaneous fat ratio (V/S). Measures were compared between groups using Wilcoxon two-sample exact tests and other metrics. Mean BMI for individuals with malignant IPMNs (28.9 kg/m$^2$) was higher than mean BMI for those with benign IPMNs (25.8 kg/m$^2$) (P=0.045). Mean VFA was higher for patients with malignant (199.3 cm$^2$) compared to benign IPMNs (120.4 cm$^2$), P=0.092. V/S was significantly higher (P=0.013) for patients with malignant versus benign IPMNs (1.25 vs. 0.69 cm$^2$), especially among females. The accuracy, sensitivity, specificity, and positive and negative predictive value of V/S in predicting malignant IPMN pathology were 74%, 71%, 76%, 75% and 72%, respectively. The findings herein support the use of measures of visceral fat from medical images as a diagnostic tool to predict IPMN pathology, acting as potential noninvasive diagnostic adjuncts for management and targets for intervention that may be more biologically-relevant than BMI.

Pancreatic ductal adenocarcinoma (PDAC), commonly known as pancreatic cancer (PC), is the fourth leading cause of cancer deaths world-wide, with high age-standardized incidence rates occurring in North America and Asia[1]. PC is diagnosed in more than 337,000 individuals each year, accounts for 4% of all cancer deaths, and has the lowest five-year relative survival rate of all leading cancers, at 8%[1]. Prognosis is poor because diagnosis typically occurs at a late, incurable stage, and prevention and early detection methods are lacking[1]. Risk factors including age, tobacco, diabetes, pancreatitis, heavy alcohol use, family history, and hereditary conditions explain only a proportion of PCs[1]. Being overweight (body mass index (BMI)≥25 kg/m$^2$) or obese (BMI≥30 kg/m$^2$) increases PC risk by 30%[2], has a population attributable fraction up to 16%[3], and influences PC survival[4-6]. Given the rise in the prevalence of obesity in North America and Asia[7, 8, 62] and the fact that obesity is a modifiable PC risk factor, an understanding of obesity's role in early pancreatic carcinogenesis is crucial for PC prevention and early detection. The inventors contend that commonly-detected PC precursors may be attributed to obesity, and that proper diagnosis and treatment of precursors and underlying obesity offer potential to reduce PC burden.

IPMNs are macrocystic PC precursors ('precancers') that[3] comprise half of the ~150,000 pancreatic cysts detected incidentally in 3% of computed tomography (CT) scans and 20% of magnetic resonance imaging (MRI) studies each year[9, 10, 3], making them more amenable to study than the microscopic PC precursor, pancreatic intraepithelial neoplasia (PanIN). Once detected, the only way to accurately determine IPMN severity/pathology (which spans from low-grade (LG) and moderate-grade (MG) to high-grade (HG) dysplasia & invasive carcinoma) is surgical resection, which is associated with an operative mortality of 2-4% and morbidity of 40-50%[11]. Consensus guidelines for IPMN management[12] depend on standard radiographic and clinical features and recommend that those with 'high risk stigmata' (main pancreatic duct (MD) involvement/dilatation ≥10 mm, jaundice, or an enhanced solid component/nodule) undergo resection, as most harbor HG or invasive disease[12]. IPMNs with 'worrisome features' (MD dilation 5-9 mm, size ≥3 cm, thickened cyst walls, non-enhanced mural nodules, or pancreatitis) are recommended for surveillance with an invasive endoscopic ultrasound-guided fine needle aspirate procedure despite poor sensitivity and complications[10, 13]. However, consensus guidelines[12] incorrectly predict pathology in 30-70% of cases[12, 14-18], causing under- and over-treatment. Thus, rationale exists for identifying noninvasive markers to improve diagnostic accuracy for IPMNs, especially those without high risk stigmata[19, 20].

Increased glucose uptake and energy metabolism is prominent in PDACs[21, 22, 39] and correlates with IPMN grade[23]. Therefore, metabolic dysregulation characterized by obesity may also associate with IPMN severity. Only one study of IPMNs[24] has specifically examined if obesity is associated with malignancy. Very high BMI (≥35 kg/m$^2$) was associated with a high prevalence of malignancy in side branch duct (BD) IPMNs. BD-IPMNs without high risk stigmata are challenging to manage[15-18, 25-27], and if obesity is a marker of malignant BD-IPMNs, this could aid in management. One major limitation of prior studies[2-6, 24, 5, 4] is that BMI was used to measure obesity. BMI is imprecise and cannot differentiate between subcutaneous fat accumulation (which represents the normal physiological buffer for excess energy intake) and abdominal/visceral adiposity[28], a facilitator of carcinogenesis through metabolic disturbances, inflammation, and fat infiltration in the pancreas[29-36, 33, 49]. Abdominal/visceral fat area (VFA) is a risk factor for pancreatic fat infiltration in patients with PC[37] and PanINs[38], and is associated with poor PC outcomes[31, 37, 39]. Routine abdominal CT scans are the gold-standard for investigating quantitative radiologic features of abdominal adiposity (such as VFA)[40], yet no published studies of these features exist for IPMN patients. The inventors sought to determine whether quantitative radiologic features of obesity extracted on abdominal CT scans can help to distinguish risk of malignant versus benign IPMNs.

Materials & Methods

Study Population and Data

The study population included a fixed cohort of 37 patients with IPMNs whose pre-operative CT images had recently been evaluated as part of a different study[20]. The cases were had initially been identified using a prospectively maintained clinical database of individuals who underwent a pancreatic resection for an IPMN between 2006 and 2011 at Moffitt Cancer Center and Research Institute (Moffitt) and provided written consent for medical images and clinical data to be donated for research through protocols approved by the Institutional Review Board (IRB) of the University of South Florida, including Total Cancer Care[41]. For all cases, demographic and clinical data (presenting systems, age at diagnosis, past medical and surgical history, and information on known and suspected cancer risk factors such as smoking, family history, and body mass index calculated from pre-surgical height and weight) was obtained from the electronic medical record and patient questionnaire. Detailed imaging studies, surgical details, pathology results, lab values (serum CA-19-9), and treatment information was collected from the medical record and Moffitt's Cancer Registry.

Histopathologic Analysis

Board-certified pathologists with expertise in PDAC and IPMN pathology (KJ, DC, BAC) previously histologically confirmed the diagnosis and degree of dysplasia using World Health Organization guidelines[42]. The final diagnosis represented the most severe grade of dysplasia observed in the neoplastic epithelium. None of the cases received pre-operative chemotherapy or radiation. 'Malignant' cases were classified as having high-grade dysplasia or invasive carcinoma and 'benign' cases were defined by low- or moderate-grade dysplasia.

CT Imaging, Acquisition, and Abdominal Obesity Assessment

Most of the CT scans from this series of patients were obtained on the Siemens Sensation (16, 40, or 64) using an abdominal or pancreatic CT angio (CTA) protocol according to standard operating procedures described previously[20]. Archived non-enhanced CT images performed within the three months prior to surgery, were acquired from Moffitt's GE Centricity Picture Archiving and Communication System (PACS). The imaging team, led by our board-certified abdominal radiologists (DJ and JC), were blinded to the final pathology. Contrast enhanced axial venous phase images were used and reviewed for high risk stigmata and worrisome features of the pancreatic lesions[12]. Non enhanced axial CT images were utilized and have previously shown to be adequate for visceral and subcutaneous fat measurements[43, 44]. Measures of total abdominal fat (TAF) area, visceral fat area (VFA), and subcutaneous fat area (SFA) were obtained using the volume segmentation and thresholding tools in AW server version 2.0 software (General Electric, Waukesha, WI, USA). The axial L2-L3 intervertebral disc level was used for analysis because adipose tissue at this level corresponds to whole body quantities[45] and is well distinguished from skeletal muscle and other structures[40, 46, 47]. CT attenuation thresholds to define adipose tissue were set between −249 and −49 Hounsfield Units[44]. TAF area on an L2-3 axial slice nearest the superior endplate of L3 was calculated by counting the volume of voxels that meet fat attenuation thresholds divided by slice thickness, which allowed standardization of measurements despite potentially different CT scan protocols. VFA was manually segmented along the fascial plane tracing the abdominal wall[48]. SFA was calculated by subtracting VFA from TAF. The VFA to SFA ratio (V/S) was calculated with V/S>0.4 cm$^2$ defined as viscerally obese[46, 49, 50]. Manual tracing of the visceral fascial plane allowed the radiologist to exclude any fat density regions within bowel or fatty lesions within organs.

Statistical Analyses

For select variables, descriptive statistics were calculated using frequencies and percents for categorical variables and means and standard deviations (SD) for continuous variables. The distributions of covariates were compared across groups using the Wilcoxon two sample two-sided exact test for continuous variables and Fisher's exact tests for categorical variables. Stratified analyses of BMI and radiologic obesity measures were conducted by gender. Spearman correlations were calculated to evaluate the relationship between BMI and quantitative radiologic obesity measures. Estimates of sensitivity, specificity, positive predictive value (PPV), and negative predictive value (NPV) were calculated for key variables. All statistical analyses were performed using SAS version 9.4 (SAS Institute, Cary, North Carolina).

Results

Study Population Characteristics

Radiologic measures of obesity were successfully calculated for 34 of the 37 cases; three cases did not have available scans in our PACS including the axial L2-L3 intervertebral disc level views for adiposity measurement. Clinical, epidemiologic, and imaging characteristics of the 34 cases (17 benign; 17 malignant) investigated in this analysis are in Table 4 and are in line with published data on other IPMN cohorts[51]. Seventy-six percent with malignant pathology had MD involvement on CT versus 24% with benign pathology (P=0.005). Mean lesion size was higher in the malignant compared to the benign group (3.4 versus 1.9 cm), P=0.003. Malignant IPMNs, particularly those deemed to be invasive, were predominately located in the pancreatic head. The majority of cases (82%) with malignant pathology had one or more high risk stigmata (MD involvement/dilatation ≥10 mm, obstructive jaundice with a cystic lesion in the pancreatic head, or an enhanced solid component within the cyst), versus 18% of those with benign pathology (P<0.001). Presence of one or more worrisome features (ie. MD dilation 5-9 mm, cyst size ≥3 cm, thickened enhanced cyst walls, non-enhanced mural nodules, or acute pancreatitis) was not associated with malignancy (P=0.708) in this cohort. BMI was higher in malignant (28.9 kg/m$^2$, 95% CI: 26.3-31.4 kg/m$^2$) versus benign cases (25.8 kg/m$^2$, 95% CI: 23.3-28.3 kg/m$^2$), with P=0.045. Mean BMI was similar in males and females, at 27.8 and 27.0 kg/m$^2$, respectively.

Analysis of Quantitative Radiologic Measures of Obesity

Mean VFA was higher in patients with malignant (199 cm$^2$) versus benign (120 cm$^2$) IPMNs, but did not reach statistical significance with the Wilcoxon two-sample exact test (P=0.092) (Table 5). Mean V/S was substantially higher in malignant versus benign IPMNs, with values of 1.25 cm$^2$ and 0.69 cm$^2$, respectively (P=0.013). We found no statistically significant differences between TAF and SFA in the malignant and benign groups.

Males had a higher mean VFA value (202.4 cm$^2$) than females (133.6 cm$^2$) and a higher mean V/S value (1.25 cm$^2$) than females (0.80 cm$^2$). Stratified analyses revealed that among both males and females, mean BMI, TAF, and VFA values were higher for patients with malignant compared to benign IPMNs, though results were not statistically significant (P>0.05) for either gender (Table 6). Among females, V/S was significantly higher for those having malignant IPMNs (P=0.038). While no correlation existed between BMI and V/S (r=0.16, P=0.35), significant positive correlations were found between BMI and VFA (r=0.68, P<0.0001) and between BMI and SFA (r=0.71, P<0.0001).

Of clinical importance, FIG. 4 displays CT scans from two IPMN patients who did not present with high risk stigmata on imaging. Both have similar BMIs but vastly different VFA and V/S values, with case 1 having higher VFA and V/S and a worrisome feature (cyst size >3 cm) and high-grade pathology and case 2 having lower VFA and V/S and low-grade pathology at resection. These data suggest that visceral fat may be added as another risk factor to potentially aid in directing management towards a necessary surgery to remove what turned out to be a high-grade lesion (case 1) and avoided an unnecessary surgery for a low-grade lesion (case 2). The accuracy, sensitivity, specificity, PPV, and NPV of V/S in predicting malignant IPMN pathology were 74%, 71%, 76%, 75% and 72%, respectively.

This project represents the first to study objectively quantitative radiologic measures of obesity as diagnostic markers of IPMN pathology. In addition to observing higher pre-operative body mass index (BMI) values in patients confirmed to have malignant IPMNs, visceral fat area (VFA) and visceral to subcutaneous ratio (V/S) values were also observed in the malignant IPMN group compared to those with benign IPMNs. We also observed that males with IPMNs had higher VFA and V/S values than female cases, in line with the observation that visceral fat is more common in males[28], and showed that women with benign IPMNs had a significantly lower V/S ratio (0.5 cm$^2$) than those with malignant IPMNs (1.4 cm$^2$), Women with benign IPMNs in our cohort appeared to have a higher subcutaneous fat area than other cohort members, consistent with data suggesting that subcutaneous fat may not be a marker of malignancy[28]. Previous authors have suggested that in an asymptomatic adult cohort, men have significantly higher V/S ratios[52]. However, no standardized gender-based V/S values are currently available which suggests further research is needed to define visceral obesity in each gender. Our small cohort, however, had relatively more females in the benign pathology group and more males in the malignant pathology group, so firm conclusions cannot be drawn based on these preliminary findings. Despite this, findings suggest that being overweight or obese, particularly in the intra-abdominal area, may be a prognostic marker for malignant potential of IPMNs. Given that abdominal/visceral adiposity has been shown to influence carcinogenesis and that BMI is an imprecise proxy for abdominal adiposity[29-36], biologically-driven[33, 49] radiologic measures of visceral fat may have greater clinical utility than BMI in predicting IPMN pathology. Further research with a larger sample size is clearly needed to distinguish the relationship between radiologic measures of visceral fat, gender, and malignancy.

Few studies have reported on quantitative radiologic measures of obesity in patients with PDAC. In a study of 9 PDAC cases and matched controls[53], no significant differences in SFA, VFA, TFA, or V/S were observed between the patients and controls. On the other hand, pre-operative visceral fat was shown to be a prognostic indicator in patients with PDAC, with increased visceral fat being associated with worse survival in patients with lymph node metastases[37]. Elevated visceral fat (defined by the visceral fat area to subcutaneous fat area ratio (V/S)) has also been shown to predict recurrence among locally advanced rectal cancer patients[50]. Collectively, these[37, 50] and other studies[31, 35] provide plausibility for our observation that VFA and V/S may be associated with more advanced IPMN pathology.

Characteristics of this cohort are representative of other IPMN cohorts, suggesting the potential for generalizability. With a larger sample size, multivariable modeling and receiver characteristic curve analyses may be helpful to determine the utility of gender-specific radiologic measures of abdominal obesity in discriminating malignant from benign IPMNs, independent of and in combination with novel molecular and radiologic markers[19, 20], standard clinical and radiologic features encompassed by consensus guidelines[12], and BMI.

In summary, use of quantitative radiologic measures of abdominal obesity could provide a noninvasive, rapid, low cost, and repeatable way of investigating features that may potentially aid in personalizing care for patients with pancreatic cancer precursors. Given that a reduction in abdominal adiposity by lifestyle, diet, and/or pharmacologic intervention would be impactful and could translate into a decreased burden of PC, obesity, and other diseases, further studies in this area are warranted.

TABLES

Table 4. Characteristics of IPMN cases in the study cohort (n = 34)

| Variable | Benign IPMNs (n = 17)[a] | Malignant IPMNs (n = 17)[b] | P |
|---|---|---|---|
| Age at diagnosis, mean (SD), years | 67.5 (10.9) | 71.8 (11.3) | 0.143 |
| Gender | | | 0.032 |

TABLES-continued

Table 4. Characteristics of IPMN cases in the study cohort (n = 34)

| Variable | Benign IPMNs (n = 17)[a] | Malignant IPMNs (n = 17)[b] | P |
|---|---|---|---|
| Male | 3 (18) | 10 (59) | |
| Female | 14 (82) | 7 (41) | |
| Race | | | 0.485 |
| White, non-Hispanic | 17 (100) | 15 (88) | |
| Black | 0 (0) | 2 (12) | |
| Jaundice as presenting symptom | | | 0.103 |
| Yes | 0 (0) | 4 (24) | |
| No | 17 (100) | 13 (76) | |
| Pre-operative serum CA 19-9 levels, mean (SD) (ng/mL) | 18.2 (19.1) | 185.5 (350.1) | 0.216 |
| Predominant tumor location | | | 0.084 |
| Pancreatic head | 6 (35) | 12 (71) | |

TABLE 5

Quantitative radiologic measures of obesity, by IPMN pathology.

| Parameter | Benign IPMNs (n = 17) | Malignant IPMNs (n = 17) | P |
|---|---|---|---|
| TAF area ($cm^2$) | 321.8 (169.5) | 391.0 (201.3) | 0.259 |
| VFA ($cm^2$) | 120.4 (68.4) | 199.3 (125.4) | 0.092 |
| SFA ($cm^2$) | 201.3 (132.1) | 191.6 (191.6) | 0.734 |
| V/S ($cm^2$) | 0.69 (0.5) | 1.25 (1.1) | 0.013 |

Data represent mean values and standard deviation. P value was estimated using Wilcoxon two sample exact tests.

TABLE 6

Gender-specific differences in Body Mass Index and Quantitative Radiologic Measures of Obesity, by IPMN Pathology.

| Parameter | Males (3 benign; 10 malignant) | P-value | Females (14 benign; 7 malignant) | P-value |
|---|---|---|---|---|
| Body Mass Index (BMI) ($kg/m^2$) | 24.0 (2.2); 29.0 (5.2) | 0.112 | 26.2 (5.3); 28.8 (4.8) | 0.224 |
| Total abdominal fat (TAF) area ($cm^2$) | 209.9 (78.9); 408.9 (227.4) | 0.371 | 328.4 (184.7); 365.3 (171) | 0.689 |
| Visceral fat area (VFA) ($cm^2$) | 174.7 (80.7); 210.7 (131.5) | 1.000 | 108.8 (62.7); 183.2 (124.3) | 0.197 |
| Subcutaneous fat area (SFA) ($cm^2$) | 116.3 (9.8); 198.3 (113.4) | 0.077 | 219.6 (139.5); 182.2 (95.7) | 0.743 |
| Visceral to Subcutaneous Ratio (V/S) ($cm^2$) | 1.5 (0.8); 1.2 (0.5) | 0.287 | 0.5 (0.2); 1.4 (1.7) | 0.038 |

Data represent mean values and standard deviation. P values estimated using the Wilcoxon two sample two-sided exact test.

TABLES-continued

Table 4. Characteristics of IPMN cases in the study cohort (n = 34)

| Variable | Benign IPMNs (n = 17)[a] | Malignant IPMNs (n = 17)[b] | P |
|---|---|---|---|
| Pancreatic body or tail | 11 (65) | 5 (29) | |
| Type of ductal communication | | | 0.005 |
| Main duct or mixed | 4 (24) | 13 (76) | |
| Branch duct | 13 (76) | 4 (24) | |
| Size of largest cyst, mean (SD) (cm) | 1.9 (1.1) | 3.4 (1.3) | 0.008 |
| Solid component or mural nodule | | | 0.141 |
| Yes | 3 (18) | 8 (47) | |
| No | 14 (82) | 9 (53) | |
| High risk stigmata | | | <0.001 |
| Yes | 3 (18) | 14 (82) | |
| No | 14 (82) | 3 (18) | |
| Worrisome features | | | 0.708 |
| Yes | 11 (65) | 13 (76) | |
| No | 6 (35) | 4 (24) | |
| BMI, mean (95% CI) ($kg/m^2$) | 25.8 (4.9) | 28.9 (4.9) | 0.045 |

Data represent counts (percentages) unless otherwise indicated. Counts may not add up to the total due to missing values, and percentages may not equal 100 due to rounding. P value estimated using the Wilcoxon two sample two-sided exact test for continuous variables and Fisher's exact tests for categorical variables.
[a]Benign IPMNs are represented by 2 low-grade and 15 moderate-grade IPMNs.
[b]Malignant IPMNs are represented by 11 high-grade and 6 invasive IPMNs.

REFERENCES

1. Yeo T P. Demographics, epidemiology, and inheritance of pancreatic ductal adenocarcinoma. Seminars in oncology. 2015; 42:8-18.
2. Marmot M, Atinmo T, Byers T, Chen J, Hirohata T, Jackson A, et al. Food, nutrition, physical activity, and the prevention of cancer: a global perspective. 2007.
3. Maisonneuve P, Lowenfels A B. Risk factors for pancreatic cancer: a summary review of meta-analytical studies. International journal of epidemiology. 2015; 44:186-98.
4. Yuan C, Bao Y, Wu C, Kraft P, Ogino S, Ng K, et al. Prediagnostic body mass index and pancreatic cancer survival. Journal of clinical oncology: official journal of the American Society of Clinical Oncology. 2013; 31:4229-34.
5. Coughlin S S, Calle E E, Patel A V, Thun M J. Predictors of pancreatic cancer mortality among a large cohort of United States adults. Cancer causes & control: CCC. 2000; 11:915-23.
6. Bracci P M. Obesity and pancreatic cancer: overview of epidemiologic evidence and biologic mechanisms. Molecular carcinogenesis. 2012; 51:53-63.
7. Flegal K M, Kruszon-Moran D, Carroll M D, Fryar C D, Ogden C L. Trends in Obesity Among Adults in the United States, 2005 to 2014. JAMA. 2016; 315:2284-91.
8. Koh J C, Loo W M, Goh K L, Sugano K, Chan W K, Chiu W Y, et al. Asian consensus on the relationship between obesity and gastrointestinal and liver diseases. Journal of gastroenterology and hepatology. 2016; 31:1405-13.
9. Megibow A J, Baker M E, Gore R M, Taylor A. The incidental pancreatic cyst. Radiol Clin North Am. 2011; 49:349-59.
10. Farrell J J. Prevalence, Diagnosis and Management of Pancreatic Cystic Neoplasms: Current Status and Future Directions. Gut and liver. 2015; 9:571-89.
11. Hines O J, Reber H A. Pancreatic surgery. Curr Opin Gastroenterol. 2008; 24:603-11.
12. Tanaka M, Fernandez-del Castillo C, Adsay V, Chari S, Falconi M, Jang J Y, et al. International consensus guidelines 2012 for the management of IPMN and MCN of the pancreas. Pancreatology. 2012; 12:183-97.
13. Panarelli N C, Sela R, Schreiner A M, Crapanzano J P, Klimstra D S, Schnoll-Sussman F, et al. Commercial molecular panels are of limited utility in the classification of pancreatic cystic lesions. Am J Surg Pathol. 2012; 36:1434-43.
14. Kim K W, Park S H, Pyo J, Yoon S H, Byun J H, Lee M G, et al. Imaging features to distinguish malignant and benign branch-duct type intraductal papillary mucinous neoplasms of the pancreas: a meta-analysis. Ann Surg. 2014; 259:72-81.
15. Roch A M, Ceppa E P, DeWitt J M, Al-Haddad M A, House M G, Nakeeb A, et al. International Consensus Guidelines parameters for the prediction of malignancy in intraductal papillary mucinous neoplasm are not properly weighted and are not cumulative. HPB: the official journal of the International Hepato Pancreato Biliary Association. 2014; 16:929-35.
16. Sahora K, Mino-Kenudson M, Brugge W, Thayer S P, Ferrone C R, Sahani D, et al. Branch duct intraductal papillary mucinous neoplasms: does cyst size change the tip of the scale? A critical analysis of the revised international consensus guidelines in a large single-institutional series. Ann Surg. 2013; 258:466-75.
17. Fritz S, Klauss M, Bergmann F, Strobel O, Schneider L, Werner J, et al. Pancreatic main-duct involvement in branch-duct IPMNs: an underestimated risk. Ann Surg. 2014; 260:848-55; discussion 55-6.
18. Goh B K, Tan D M, Ho M M, Lim T K, Chung A Y, Ooi L L. Utility of the sendai consensus guidelines for branch-duct intraductal papillary mucinous neoplasms: a systematic review. J Gastrointest Surg. 2014; 18:1350-7.
19. Permuth-Wey J, Chen D T, Fulp W J, Yoder S J, Zhang Y, Georgeades C, et al. Plasma MicroRNAs as Novel Biomarkers for Patients with Intraductal Papillary Mucinous Neoplasms of the Pancreas. Cancer Prev Res (Phila). 2015.
20. Permuth J B, Choi J, Balarunathan Y, Kim J, Chen D T, Chen L, et al. Combining radiomic features with a miRNA classifier may improve prediction of malignant pathology for pancreatic intraductal papillary mucinous neoplasms. Oncotarget. 2016.
21. Lee S M, Kim T S, Lee J W, Kim S K, Park S J, Han S S. Improved prognostic value of standardized uptake value corrected for blood glucose level in pancreatic cancer using F-18 FDG PET. Clin Nucl Med. 2011; 36:331-6.
22. Regel I, Kong B, Raulefs S, Erkan M, Michalski C W, Hartel M, et al. Energy metabolism and proliferation in pancreatic carcinogenesis. Langenbecks Arch Surg. 2012; 397:507-12.
23. Basturk O, Singh R, Kaygusuz E, Balci S, Dursun N, Culhaci N, et al. GLUT-1 expression in pancreatic neoplasia: implications in pathogenesis, diagnosis, and prognosis. Pancreas. 2011; 40:187-92.
24. Sturm E C, Roch A M, Shaffer K M, Schmidt C M, 2nd, Lee S J, Zyromski N J, et al. Obesity increases malignant risk in patients with branch-duct intraductal papillary mucinous neoplasm. Surgery. 2013; 154:803-8; discussion 8-9.
25. Correa-Gallego C, Ferrone C R, Thayer S P, Wargo J A, Warshaw A L, Fernandez-Del Castillo C. Incidental pancreatic cysts: do we really know what we are watching? Pancreatology. 2010; 10:144-50.
26. Salvia R, Malleo G, Marchegiani G, Pennacchio S, Paiella S, Paini M, et al. Pancreatic resections for cystic neoplasms: from the surgeon's presumption to the pathologist's reality. Surgery. 2012; 152: S135-42.
27. Lafemina J, Katabi N, Klimstra D, Correa-Gallego C, Gaujoux S, Kingham T P, et al. Malignant progression in IPMN: a cohort analysis of patients initially selected for resection or observation. Ann Surg Oncol. 2013; 20:440-7.
28. Ibrahim M M. Subcutaneous and visceral adipose tissue: structural and functional differences. Obesity reviews: an official journal of the International Association for the Study of Obesity. 2010; 11:11-8.
29. Batista M L, Jr., Olivan M, Alcantara P S, Sandoval R, Peres S B, Neves R X, et al. Adipose tissue-derived factors as potential biomarkers in cachectic cancer patients. Cytokine. 2013; 61:532-9.
30. Malietzis G, Aziz O, Bagnall N M, Johns N, Fearon K C, Jenkins J T. The role of body composition evaluation by computerized tomography in determining colorectal cancer treatment outcomes: a systematic review. European journal of surgical oncology: the journal of the European Society of Surgical Oncology and the British Association of Surgical Oncology. 2015; 41:186-96.
31. Vongsuvanh R, George J, Qiao L, van der Poorten D. Visceral adiposity in gastrointestinal and hepatic carcinogenesis. Cancer Lett. 2013; 330:1-10.
32. Mathur A, Marine M, Lu D, Swartz-Basile D A, Saxena R, Zyromski N J, et al. Nonalcoholic fatty pancreas disease. HPB: the official journal of the International Hepato Pancreato Biliary Association. 2007; 9:312-8.
33. Smits M M, van Geenen E J. The clinical significance of pancreatic steatosis. Nat Rev Gastroenterol Hepatol. 2011; 8:169-77.
34. O'Flanagan C H, Bowers L W, Hursting S D. A weighty problem: metabolic perturbations and the obesity-cancer link. Hormone molecular biology and clinical investigation. 2015; 23:47-57.
35. Feakins R M. Obesity and metabolic syndrome: pathological effects on the gastrointestinal tract. Histopathology. 2016; 68:630-40.
36. Polvani S, Tarocchi M, Tempesti S, Bencini L, Galli A. Peroxisome proliferator activated receptors at the crossroad of obesity, diabetes, and pancreatic cancer. World journal of gastroenterology: WJG. 2016; 22:2441-59.
37. Mathur A, Hernandez J, Shaheen F, Shroff M, Dahal S, Morton C, et al. Preoperative computed tomography measurements of pancreatic steatosis and visceral fat: prognostic markers for dissemination and lethality of pancreatic adenocarcinoma. HPB: the official journal of the International Hepato Pancreato Biliary Association. 2011; 13:404-10.
38. Rebours V, Gaujoux S, d'Assignies G, Sauvanet A, Ruszniewski P, Levy P, et al. Obesity and Fatty Pancreatic Infiltration Are Risk Factors for Pancreatic Precancerous Lesions (PanIN). Clin Cancer Res. 2015; 21:3522-8.

39. Eastwood S V, Tillin T, Wright A, Heasman J, Willis J, Godsland I F, et al. Estimation of CT-derived abdominal visceral and subcutaneous adipose tissue depots from anthropometry in Europeans, South Asians and African Caribbeans. PLoS One. 2013; 8:e75085.
40. Andreoli A, Garaci F, Cafarelli F P, Guglielmi G. Body composition in clinical practice. Eur J Radiol. 2016; 85:1461-8.
41. Fenstermacher D A, Wenham R M, Rollison D E, Dalton W S. Implementing personalized medicine in a cancer center. Cancer J. 2011; 17:528-36.
42. Adsay N V F T, Hruban R H, Klimstra D S, Kloppel G, et al, Intraductal Papillary Mucinous Neoplasm of the Pancreas. In: Bosman F T, Carneiro F, Hruban R H, Theise N D, editors. WHO classification of tumors of the digestive system. Lyon: WHO Press; 2010. p. 304-313.
43. Pickhardt P J, Jee Y, O'Connor S D, del Rio A M. Visceral adiposity and hepatic steatosis at abdominal CT: association with the metabolic syndrome. AJR Am J Roentgenol. 2012; 198:1100-7.
44. Ryckman E M, Summers R M, Liu J, Munoz del Rio A, Pickhardt P J. Visceral fat quantification in asymptomatic adults using abdominal CT: is it predictive of future cardiac events? Abdominal imaging. 2015; 40:222-6.
45. Martin L. Diagnostic criteria for cancer cachexia: data versus dogma. Curr Opin Clin Nutr Metab Care. 2016; 19:188-98.
46. Yip C, Dinkel C, Mahajan A, Siddique M, Cook G J, Goh V. Imaging body composition in cancer patients: visceral obesity, sarcopenia and sarcopenic obesity may impact on clinical outcome. Insights into imaging. 2015; 6:489-97.
47. Shen W, Punyanitya M, Wang Z, Gallagher D, St-Onge M P, Albu J, et al. Total body skeletal muscle and adipose tissue volumes: estimation from a single abdominal cross-sectional image. Journal of applied physiology (Bethesda, Md.: 1985). 2004; 97:2333-8.
48. Nattenmueller J, Hoegenauer H, Boehm J, Scherer D, Paskow M, Gigic B, et al. CT-based compartmental quantification of adipose tissue versus body metrics in colorectal cancer patients. European radiology. 2016.
49. Whitaker K M, Choh A C, Lee M, Towne B, Czerwinski S A, Demerath E W. Sex differences in the rate of abdominal adipose accrual during adulthood: The Fels Longitudinal Study. International journal of obesity (2005). 2016.
50. Clark W, Siegel E M, Chen Y A, Zhao X, Parsons C M, Hernandez J M, et al. Quantitative measures of visceral adiposity and body mass index in predicting rectal cancer outcomes after neoadjuvant chemoradiation. J Am Coll Surg. 2013; 216:1070-81.
51. Matthaei H, Schulick R D, Hruban R H, Maitra A. Cystic precursors to invasive pancreatic cancer. Nat Rev Gastroenterol Hepatol. 2011; 8:141-50.
52. Maurovich-Horvat P, Massaro J, Fox C S, Moselewski F, O'Donnell C J, Hoffmann U. Comparison of anthropometric, area- and volume-based assessment of abdominal subcutaneous and visceral adipose tissue volumes using multi-detector computed tomography. International journal of obesity (2005). 2007; 31:500-6.
53. Kwee T C, Kwee R M. Abdominal adiposity and risk of pancreatic cancer. Pancreas. 2007; 35:285-6.

Example 3—Circulating Long Non-Coding RNAs as Markers of IPMNs

Pancreatic ductal adenocarcinoma (PDAC) is an aggressive disease that lacks effective biomarkers for early detection. We hypothesized that circulating long non-coding RNAs (lncRNAs) may act as diagnostic markers of incidentally-detected cystic PDAC precursors known as intraductal papillary mucinous neoplasms (IPMNs) and predictors of their pathology. Using NanoString NCOUNTER technology, we measured the abundance of 28 candidate lncRNAs in pre-operative plasma from a cohort of pathologically-confirmed IPMN cases of various grades of severity and non-diseased controls. Results showed that two lncRNAs (GAS5 and SRA) aided in differentiating IPMNs from controls. An 8-lncRNA signature (including ADARB2-AS1, ANRIL, GLIS3-AS1, LINC00472, MEG3, PANDA, PVT1, and UCA1) performed better than standard clinical and radiologic features in distinguishing 'aggressive/malignant' IPMNs that warrant surgical removal from 'indolent/benign' IPMNs that can be observed. When the 8-lncRNA signature was combined with plasma miRNA data and quantitative 'radiomic' imaging features, the accuracy of IPMN pathology prediction improved. Our findings provide novel information on the ability to detect lncRNAs in plasma from patients with IPMNs and suggest that an lncRNA-based blood test may have utility as a diagnostic adjunct for identifying IPMNs and their pathology, especially when incorporated with biomarkers such as miRNAs, quantitative imaging features, and clinical data.

Pancreatic ductal adenocarcinoma (PDAC) is the third leading cause of cancer deaths in the United States, with a five-year survival rate of only 9%[1]. Most cases are diagnosed at a late, incurable stage due to the lack of accurate methods for early detection[1]. Serum carbohydrate antigen 19-9 (CA19-9) is used to suggest a diagnosis of PDAC and monitor disease recurrence or response to therapy. However, it's utility as a sensitive and specific marker of early PDAC is poor[2]. The detection and treatment of noninvasive precursor lesions offers hope in reducing PDAC-related morbidity and mortality. Intraductal papillary mucinous neoplasms (IPMNs) of the pancreas are a morphologically distinct set of tumors located in the duct epithelium and are characterized by papillary epithelial proliferation and mucin production, leading to cystic dilation of involved ducts[3]. These cystic PDAC precursor lesions ('precancers')[3] comprise almost half of the ~150,000 asymptomatic pancreatic cysts detected incidentally in the general population each year by computed tomography (CT) scans and magnetic resonance imaging (MRI)[4,5]. Despite their detection, the only way to examine their severity which ranges from noninvasive/pre-malignant (low-grade (LG), moderate-grade (MG), or high-grade (HG) dysplasia) to invasive carcinoma is through surgical resection, which carries significant risks of morbidity and mortality[6-8]. Studies reveal that the 5-year survival rate for patients with noninvasive IPMNs is greater than 70%, which is significantly higher than the 22-45% rate for individuals with resected invasive IPMNs and the 10-25% survival rate reported for individuals with resected conventional PDACs[9]. Thus, proper diagnosis of disease and its severity (noninvasive versus invasive IPMN versus conventional PDAC not associated with an IPMN) is important for medical management.

Consensus guidelines for IPMN management[10] depend on standard radiographic and clinical features and recommend that patients with 'high risk stigmata (HRS)' (main pancreatic duct (MD) involvement/dilatation ≥10 mm, obstructive jaundice with a cystic lesion in the pancreas head, or an enhanced solid component/nodule within the cyst) undergo resection, as most harbor high-grade or invasive disease[10]. More challenging to manage are IPMNs having 'worrisome features (WF)' (MD dilation 5-9 mm, cyst size ≥3 cm, thickened enhanced cyst walls, non-enhanced mural nodules, or acute pancreatitis). It is suggested that these lesions undergo endoscopic evaluation with endoscopic ultrasound with fine needle aspiration (EUS-FNA) despite suboptimal sensitivity and technical complications[5,11]. The guidelines provide an important framework for management, but there is disagreement between the preoperative diagnosis and pathologic examination in a large percentage (30-70%) of cases[10,12-16]. Novel, noninvasive markers of IPMN pathology are needed, especially for individuals who do not present with HRS.

Non-coding RNAs (ncRNAs) are outstanding candidate biomarkers of early neoplasia due to their stability in tissue[17,18] and biofluids[19,20] and their ability to regulate hundreds of genes and biological pathways. ncRNAs are typically classified according to their size; small ncRNAs are less than 200 nucleotides in length whereas long ncRNAs contain at least 200 nucleotides and resemble protein-coding transcripts but without functional open reading frames[21]. We[22,23] and others[24-26] have conducted genome-wide analysis of miRNAs, the best characterized class of small ncRNAs, using tissue and plasma or serum from IPMN patients and healthy controls. Collectively, these data support miRNAs as a promising diagnostic adjunct for stratifying IPMN patients for surveillance or resection. Furthermore, in a small retrospective cohort of IPMN cases, we found diagnostic performance to improve when combining plasma miRNA data with quantitative 'radiomic' features naked to the human eye extracted from routine CT scans[27]. LncRNAs are not as well studied as miRNAs even though they are the predominant transcribed RNAs[28] and have been shown to regulate gene expression and promote carcinogenesis through mechanisms such as transcriptional regulation, initiation of chromatin remodeling, modulating alternative splicing, altering protein activity or localization, and genomic imprinting[21,29,30]. Given emerging data on the role of lncRNAs in PDAC initiation, progression, and outcomes[31-39] and evidence to support lncRNA detection in circulation[38,40-44], we conducted the first study to measure the abundance of circulating lncRNAs from patients with IPMNs.

Here we quantified the abundance of 28 candidate lncRNAs in archived plasma obtained pre-operatively from individuals with noninvasive and invasive IPMNs and age- and gender-matched disease-free controls using the NCOUNTER technology (NanoString, Inc, Seattle, Washington) digital quantification method[45]. We then aimed to 1) discover circulating lncRNAs that may distinguish between patients with IPMNs and non-diseased controls, 2) identify circulating lncRNAs that may differentiate malignant/aggressive IPMNs (classified as those pathologically confirmed to have high-grade dysplasia or invasive disease) from benign/more indolent IPMNs (classified as those confirmed to have low- or moderate-grade dysplasia), and 3) determine the performance of circulating lncRNAs in predicting IPMN pathology individually and in combination with existing miRNA and quantitative imaging data described in our previous publications[22,27]. Our findings provide new information on circulating lncRNAs and their potential to help individualize risk assessment and management for individuals with IPMNs.

Materials & Methods

Study Population and Biospecimens

A prospectively maintained clinical database was retrospectively reviewed to identify individuals who underwent a pancreatic resection for an IPMN between 2006 and 2011 at Moffitt Cancer Center and Research Institute (Moffitt) and had provided written consent for blood to be donated pre-operatively for research through protocols approved by the Institutional Review Board (IRB) of the University of South Florida, including Total Cancer Care[70]. IRB approval was granted for study participation and the research described herein (IRB #Pro4971), written informed consent was obtained from study participants, and all methods were performed in accordance with relevant guidelines and regulations. The diagnosis and degree of dysplasia was pathologically confirmed using World Health Organization (WHO) guidelines[3]. The final diagnosis represented the most severe grade of dysplasia observed in the neoplastic epithelium. None of the included cases received pre-operative chemotherapy or radiation. Also eligible for inclusion were age- and gender-matched healthy controls with no current or prior history of pancreatic disease or symptoms who presented to Moffitt's Cancer Screening and Prevention Center during the same time period and donated blood through a related IRB-approved protocol using the same procedures.

Blood was collected from consented participants via phlebotomy in a 7-mL EDTA tube and processed for plasma within two hours using standard procedures[71]. The tube was inverted 3 times and spun at 3600 rpm for 8 minutes and then aliquoted into 0.5 mL bar-coded cryovials and banked at −80° C. Demographic, clinical, and epidemiologic data was collected from an electronic questionnaire, the medical record, Moffitt's cancer registry, and other sources.

RNA Isolation and Multiplexed Target Enrichment (MTE)

One 0.5 mL cryovial of plasma was retrieved and thawed for each study participant. To assess hemolysis, samples were visually inspected and spectrophotometric analysis was performed at 414, 541, and 576 nm[72]. Samples were classified as hemolyzed if the $A_{414}$, $A_{541}$, or $A_{576}$ value exceeded 0.2. Synthetic spike-in RNA representing NEFL (neurofilament 1), ENO2 (neuron-specific endonuclease) and GFAP (glial fibrillary acidic protein) were added to plasma to control for variance in the starting material and the efficiency of RNA extraction, according to vendor recommendations. Cell-free RNA was then isolated from 500 µl of plasma using the Plasma/Serum RNA Purification Midi Kit with a final elution volume of 50 µl (Norgen Biotek Corp, Ontario, CA). The extracted RNA was further purified and concentrated down to 30 µl using the Zymo RNA Clean and Concentrator-5 kit (Zymo Research Corp, Irvine, CA). The concentrated RNA was qualitatively assessed on the Agilent BioAnalyzer Total RNA Pico chip (Agilent Technologies, Santa Clara, CA). As the RNA was expected to be degraded, a BioAnalyzer peak from 25-200 nt indicated successful RNA recovery. Four µl of RNA was reverse transcribed into single-stranded cDNA using the Invitrogen SuperScript VILO cDNA Synthesis Kit and Master Mix (Thermo Fisher Scientific, Waltham, MA) following the nCounter Single Cell Gene Expression protocol (NanoString Technologies, Seattle, WA). The single-stranded cDNA was enriched using a highly multiplexed pool of target-specific PCR primer pairs targeting 28 lncRNAs. The MTE process was carried out using 22 cycles of PCR using the ABI TaqMan PreAmp MasterMix (Thermo Fisher Scientific, Waltham, MA) with the conditions described in the NanoString protocol.

Quality Control of the Multiplexed Target Enrichment and Hybridization

The resulting PCR products from the Multiplexed Target Enrichment were assessed using quantitative RT-PCR (qPCR) to evaluate the expression of several target genes and normalize the amount of MTE DNA input into the NanoString hybridization. The MTE PCR products were diluted 1:100 and assayed on an Illumina Eco using ABI SYBR Green PCR Master Mix for genes, GNAS and VIM, which were confirmed to be expressed stably based on initial data generated from the custom NanoString CodeSet (data not shown). The resulting Cq values for both genes were used to generate a dilution factor for each sample. Dilution factors were calculated by targeting each sample's effective Cq value (post-dilution) to equal 16 for GNAS and 19 for VIM, which were the approximate values generated by the successful pilot samples (those with binding densities between 0.05 and 2.25 spots per square micron). Samples with Cq values greater than the target values were not diluted, and in samples where calculations resulted in significantly different dilution factors, the higher dilution factor was selected in order to avoid cartridge overloading. Following the dilution of the MTE PCR product, the DNA was denatured for 2 minutes at 94° C. then snap cooled on ice for 5 minutes prior to hybridization. The samples were hybridized overnight at 65° C. with the custom codeset described below.

High-Throughput Measurement of lncRNA Abundance

A custom NCOUNTER Expression Assay codeset (Nanostring Technologies, Seattle, WA, USA) was used to quantify the abundance of 28 lncRNAs selected because of their role in the development or progression of pancreatic and other cancers after review of published literature[31-37]ADARB2-AS1, ANRIL, AS1DHRS4, BCYRN1, DDX6P, GAS5, GLIS3-AS1, H19, HOTAIR, HOTTIP, HOXD-AS1, HULC, LINC00244, LINC00469, LINC00472, LINC00491, lncRNA p21, MALAT1, MEG3, PANDA, PPP3CB, PTENP1, PVT1, SRA, TERC, UCA1, XIST, αHIF. The codeset also included positive controls, negative controls, three mRNA spike-in targets, four WBC cellular contamination targets (APOE, CD68, CD2, and CD3) three hemolysis/erythrocyte targets (MB, NGB, CYGB), and messenger RNA (mRNA) housekeeping genes (ACTB, PGK1, and PPIB). The NanoString cartridge was processed on the NanoString NCOUNTER Prep Station using the high sensitivity protocol and scanned at the highest sensitivity setting (550 fields of view) on the NCOUNTER Digital Analyzer. Data quality control was performed using the NanoString NSOLVER software, and were exported for normalization and analysis.

Data Processing and Quality Control

For each sample, background-corrected measures of lncRNA expression were estimated by subtracting the negative control average plus two standard deviation (SD) cutpoint from the raw lncRNA counts. lncRNAs with less than 20% of samples above the negative control cut-point (i.e., low-expression probes) were removed from downstream analysis. Possible WBC and erythrocyte sample contamination was evaluated using built-in controls. Data for each sample was normalized using the geometric mean of the three housekeeping genes (ACTB, PGK1 and PPIB), each of which appeared to be invariant/stable in the dataset. Normalized data was log 2-transformed prior to signature selection.

Statistical Analysis

Descriptive statistics were calculated using frequencies and percents for categorical variables and means and standard deviations (SD) for continuous variables. Data analysis was performed to identify a panel of lncRNAs that a) differentiate between IPMN cases and non-diseased controls and b) distinguish malignant (pathologically-confirmed as HG or invasive) from benign IPMNs (pathologically-confirmed as LG or MG).

Identification of Plasma lnRNA Signatures

Linear models for microarray data (LIMMA)[73] was used to identify lncRNAs that differentiate between IPMN cases and controls and between malignant and benign IPMNs, respectively. Since lncRNAs can be over- or under-expressed, we used principal component analysis (PCA) to combine the most deregulated lncRNAs and generate an overall 'IPMN-risk score' based on the first principal component (PC1), which accounts for the largest variability in the data and represents the overall combined effect of an IPMN-risk lncRNA signature. Specifically, IPMN-risk score, defined by PC1 as $\Sigma w_i x_i$, is a weighted average expression among the IPMN-risk lncRNAs, where $x_i$ represents lncRNA i expression level, $w_i$ is the corresponding weight (PC1's loading coefficient for lncRNA i) with $\Sigma w_i^2 = 1$, and the $w_i$ values maximize the variance of $\Sigma w_i x_i$. This approach has been used to derive gene signatures previously[22,74-77].

Receiver operating characteristic (ROC) curves were generated to measure the predictive power of the IPMN-risk signatures in discriminating between groups. Youdon method was used to determine the best threshold value for each model based on maximum of sum of sensitivities and specificities as the optimality criterion[78]. Estimates of sensitivity, specificity, positive predictive value (PPV), and negative predictive value (NPV) were calculated. For the analysis of malignant versus benign cases, we also conducted multivariable logistic regression analysis to assess whether the identified lncRNA signature was associated with malignant IPMN status independent of known prognostics factors (i.e., main-duct involvement, lesion size, serum CA-19-9 level)[10]. Finally, to assess the extent to which data types in addition to plasma lncRNAs and standard clinical and radiologic features may augment correct prediction of malignant versus benign pathology, logistic regression models and ROC curves were also generated for a subset of cases with existing pre-operative plasma miRNA and radiomic data produced according to methods described in previous studies[22,27] and reviewed below. P values were adjusted with a false discovery rate (FDR) approach using the Benjamini and Hochberg method[79].

miRNA Expression Data

Preoperative plasma miRNA expression data was generated previously[22] for 42 surgically-resected, pathologically-confirmed IPMN cases (21 malignant and 21 benign) using one 0.5-mL cryovial of plasma per case. Briefly, RNA spike-in miRNAs (synthetic control templates) were used and total RNA isolation was performed on 500 uL of plasma using the Plasma/Serum Circulating and Exosomal RNA Purification Mini Kit (Slurry Format) from Norgen Biotek (Ontario, Canada). The NCOUNTER Human v2 miRNA Expression Assay Codeset (NanoString Technologies, Seattle, WA, USA) was used to quantify the abundance of a pre-defined panel of 800 human miRNAs and built-in controls, and raw miRNA counts underwent technical and biological normalization and log 2-transformation. The most deregulated miRNAs were identified using the linear models for microarray data (LIMMA) method and a principal component analysis (PCA) approach (14). A focused analysis of the 42 IPMN cases showed that five miRNAs (miR-200a-3p, miR-1185-5p, miR-33a-5p, miR-574-3p, and miR-663b) had an AUC value of 0.73 (95% CI: 0.58-0.89) in discriminating between groups.

CT Acquisition and Radiomic Feature Selection and Extraction

Preoperative CT images were available for 38 of the 42 surgically-resected, pathologically-confirmed IPMN cases with available matched preoperative miRNA expression data generated previously[22]. CT images were obtained from Moffitt's GE Centricity Picture Archiving and Communication System (PACS). CT images were reviewed for standard radiologic features encompassing 'high-risk stigmata' and 'worrisome features' represented in consensus guidelines[10]. Axial venous phase images (3 mm) were used for most patients the region of interest (ROI) by helping to outline the peripheral margin of tumors in their entirety, capturing both solid (nodular) and cystic components. The radiomics team then marked the ROI using Definiens/GE AWS Advanced Visualization software. The entire tumors were identified (solid and cystic components) using a semi-manual version of a single click semi-automated ensemble segmentation algorithm within the Definiens Developer XD (Munich, Germany) software platform. Target lesions were segmented, with a second radiologist finalizing the segmentation boundaries on the CT slices. We then extracted categories of 18 non-texture and 94 texture features. Non-texture features measure tumor size (volume, diameter, border length), shape (compactness, asymmetry), and location, whereas texture features measure properties such as smoothness, coarseness, and regularity. We focused on evaluating two-dimensional (2D) quantitative features in the middle CT slice. In house algorithms for feature extraction and quantification of segmented regions were implemented by custom routines in the Definiens Platform. Logistic regression, PCA, and cross-validation analyses were used to examine associations between features and IPMN pathology. Fourteen features, most of which were textural, differentiated malignant from benign IPMNs and collectively had an AUC value of 0.77.

Cross-Validation Analysis

To evaluate model performance, repeated (10,000 times) 10-fold cross validation was performed. The average and 95% confidence intervals of accuracy, sensitivity, specificity, PPV and NPV were estimated. In each 10-fold cross-validation, data were split into 10 subsets. By holding one subset of data (test set), the remaining 9 subsets were used as a training set to build a model for prediction evaluation in the test set. The process continued until each subset was used as the test set. By testing the model on a test set (not used in estimation), cross-validation aimed to reduce over-fitting. All statistical analyses were performed using SAS version 9.4 and R version 3.2.5.

Results

Study Population

Pre-operative plasma samples were evaluated for 57 IPMN cases and 24 non-diseased controls frequency-matched by age-group and gender. Eight samples were excluded prior to normalization and statistical analysis due to: failure to amplify (1 case) and high binding density due to possible over-seeding of the NCOUNTER cartridge or erythrocyte contamination (5 cases, 2 controls), leaving samples from 73 participants (51 cases, 22 controls) for analysis. Study population characteristics are shown in Table 7. Cases and controls were well-matched on age (mean age: 68.5 vs 68.2 years). Most subjects were white, non-Hispanic. IPMN cases were more likely (47%) to have smoked cigarettes than controls (36%). The distribution of low-, moderate-, high-grade, and invasive IPMN cases was 12%, 29%, 24%, and 35%, respectively. Selected characteristics of the IPMN cohort are summarized in Table 8. Pre-operatively, compared to benign IPMNs (those with pathologically-confirmed low- or moderate grade dysplasia), malignant IPMNs (those with high-grade or invasive disease) were significantly (p<0.05) more likely to be associated with: jaundice as a presenting symptom, tumors in the pancreatic head, MD involvement, and a solid component or mural nodule.

TABLE 7

Characteristics of the Study Population (N = 73)

| Variable | IPMN cases (n = 51) | Healthy controls (n = 22) |
|---|---|---|
| Age at diagnosis/interview, mean (SD)(yrs) | 68.5 (10.0) | 68.2 (9.4) |
| Gender, male:female, n (%) | 27 (53):24 (47) | 11 (50):11 (50) |
| Race, n (%) | | |
| White, Non-Hispanic | 47 (92) | 22 (100) |
| Other | 4 (8) | 0 (0) |
| Ever Smoker, n (%) | | |
| Yes | 24 (47) | 8 (36) |
| No | 21 (41) | 8 (36) |
| Unknown | 6 (12) | 6 (27) |
| IPMN Grade, n (%) | | |
| Low | 6 (12) | — |
| Moderate | 15 (29) | — |
| High | 12 (24) | — |
| Invasive | 18 (35) | — |

Data represent counts (percentages) unless otherwise indicated. Counts may not add up to the total due to missing values, and percentages may not equal 100 due to rounding.

TABLE 8

Characteristics of IPMN cases in the cohort (N = 51)

| Variable | Benign[1] IPMNs (n = 21) | Malignant[2] IPMNs (n = 30) | pvalue |
|---|---|---|---|
| Age at diagnosis, mean (SD)(yrs) | 68.4 (9.8) | 68.6 (10.3) | 0.939 |
| Male:Female, n (%) | 8(38):13(62) | 19(63):11(37) | 0.075 |
| Body mass index (BMI), mean (SD) | 26.5 (4.6) | 27.9 (4.6) | 0.355 |
| Positive personal history of diabetes | 4 (19) | 4 (13) | 0.621 |
| Positive personal history of chronic pancreatitis | 5 (24) | 9 (30) | 0.126 |
| Had abdominal pain as presenting symptom | 7 (37) | 11 (37) | 0.165 |
| Had weight loss as presenting symptom | 3 (14) | 8 (27) | 0.110 |
| Had jaundice as presenting symptom | 1 (5) | 8 (27) | 0.012 |
| Pre-operative serum CA 19-9 levels, mean (SD)(ng/mL) | 91 (314) | 692 (1493) | 0.125 |
| Pre-operative serum albumin levels, mean (SD)(ng/mL) | 4.4 (0.98) | 3.9 (0.66) | 0.073 |

TABLE 8-continued

Characteristics of IPMN cases in the cohort (N = 51)

| Variable | Benign[1] IPMNs (n = 21) | Malignant[2] IPMNs (n = 30) | pvalue |
|---|---|---|---|
| Predominant tumor location | | | 0.013 |
| Pancreatic Head | 6 (29) | 14 (47) | |
| Pancreatic Body or Tail | 14 (67) | 12 (40) | |
| Diffuse | 1 (5) | 4 (13) | |
| Type of ductal communication | | | 0.003 |
| Main duct or mixed | 4 (22) | 10 (30) | |
| Branch duct | 14 (78) | 4 (13) | |
| Size of largest cyst on imaging, mean (range) (cm) | 2.8 (1.6) | 3.5 (1.4) | 0.145 |
| Solid component or mural nodule | | | 0.021 |
| Yes | 3 (14) | 8 (27) | |
| No | 15 (71) | 6 (20) | |

Data represent counts (percentages) unless otherwise indicated. Counts may not add up to the total due to missing values, and percentages may not equal 100 due to rounding.
[1]Benign IPMNs are represented by 6 low-grade and 15 moderate-grade IPMNs.
[2]Malignant IPMNs are represented by 12 high-grade and 18 invasive IPMNs.

Analysis of Plasma lncRNAs in IPMN Cases Versus Non-Diseased Controls

Each of the 28 lncRNAs had signals above background and was included in analyses. No statistically significant differences were observed between IPMN and control samples in the frequency or the amount of erythrocyte contamination. After normalization, two lncRNAs (GAS5 and SRA) differentiated the 51 IPMN samples from the 22 control samples using a threshold of p<0.05. Compared to controls, IPMN cases had 0.9-fold lower GAS5 expression and 1.2 fold higher SRA expression. The 2-lncRNA signature, represented by PC1, explained 60% of the variability in the data, suggesting it represents the signature well. The area under the curve (AUC) value was 72.9 (95% CI: 60.9-84.9). The sensitivity, specificity, positive predictive value (PPV), and negative predictive value (NPV) for IPMN detection were 82%, 59%, 82% and 59%, respectively.

Analysis of Plasma lncRNAs in Malignant Versus Benign IPMNs

Figure 5:
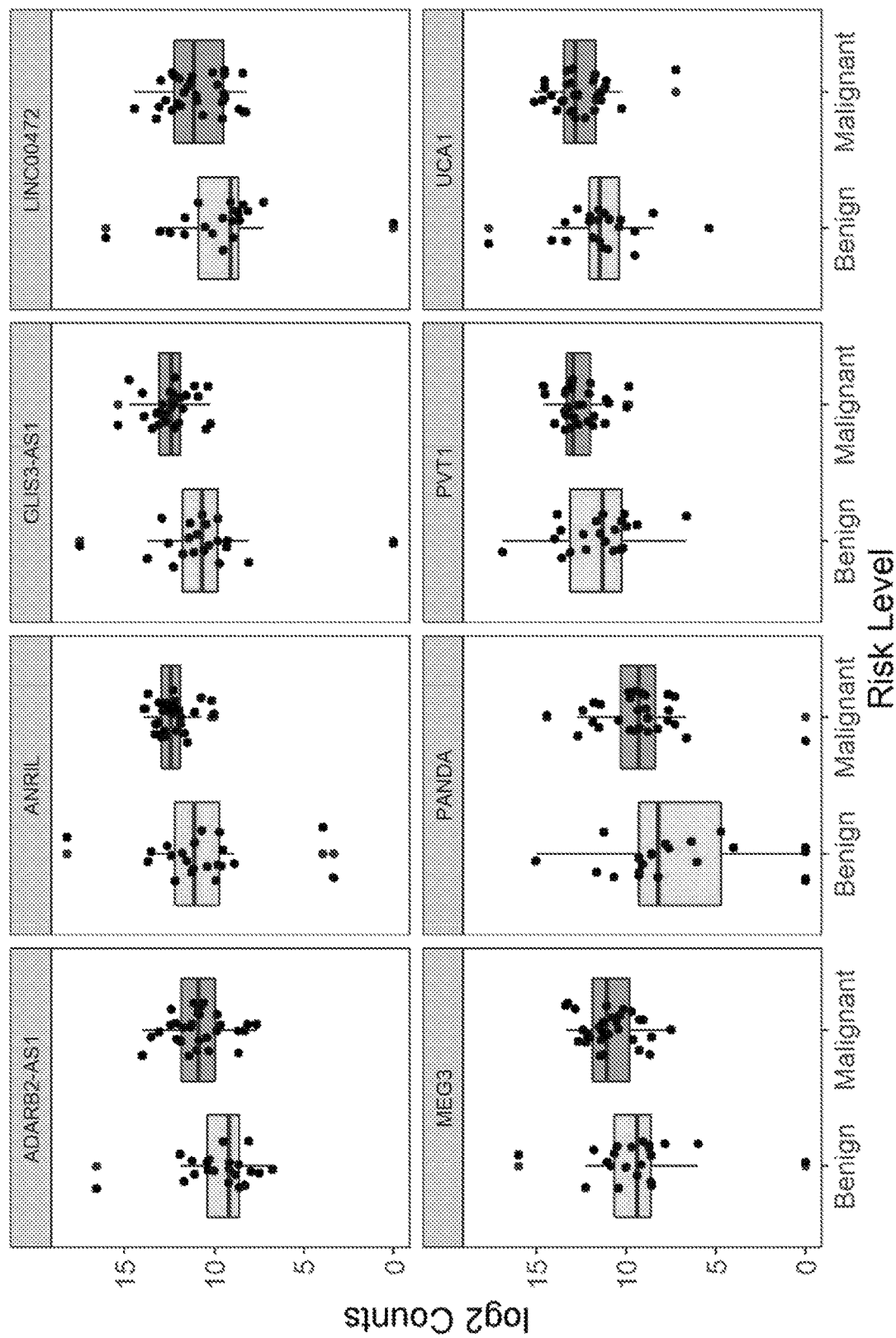
FIG. 5. Eight lncRNAs in circulation discriminated malignant (n=30) from benign (n=21) IPMN cases (p<0.05). Box plots displaying the distribution of the abundance of each individual lncRNA within the malignant and benign groups.
Figure 6A:
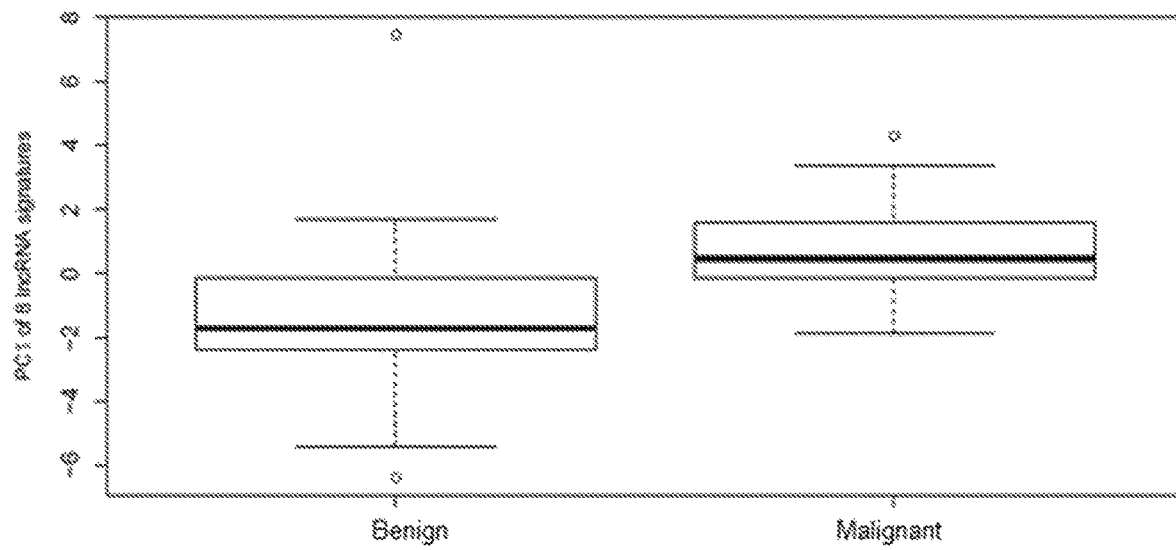
FIGS. 6A-6B. The 8-lncRNA signature associates with IPMN pathology.
Figure 6B:
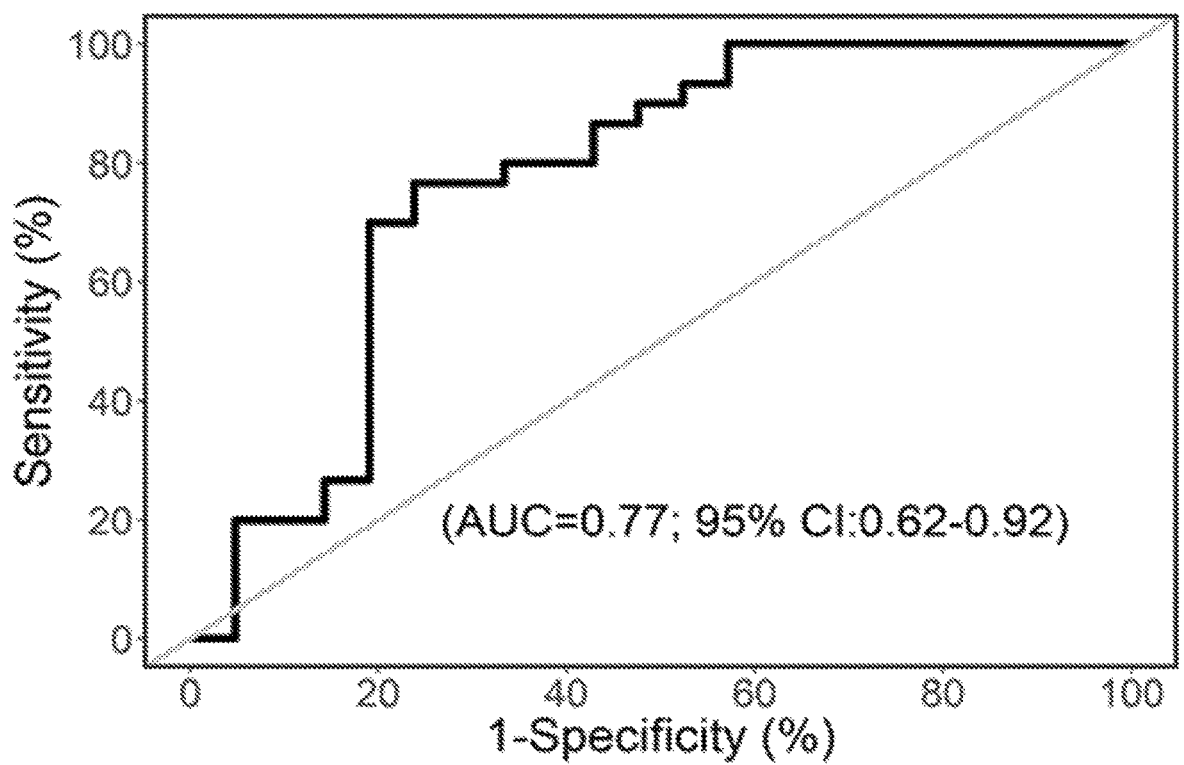

We evaluated the ability of the 2-lncRNA signature (identified in the analysis of IPMN cases versus non-diseased controls) to discriminate between the 30 malignant and 21 benign IPMNs and observed it did not perform well (AUC=55.1 (95% CI: 38.1-72.1)). However, a focused analysis of the 51 IPMN cases showed that a signature of eight lncRNAs (ADARB2-AS1, ANRIL, GLIS3-AS1, LINC00472, MEG3, PANDA, PVT1, and UCA1) discriminated between the malignant and benign IPMNs (p<0.05) (Table 9; FIG. 5). The 8-lncRNA signature was also characterized by a PC1 score and explained 67% of the variability. The overall expression of the 8-lncRNA signature was higher in malignant compared to benign IPMNs (p=0.001, FIG. 6), was significantly associated with malignant status (OR (95% CI): =1.56 (1.11-2.21), p=0.011), and had an AUC value of 0.77 (95% CI: 0.62-0.92) in discriminating between groups (FIG. 6). Estimates of sensitivity, specificity, PPV, and NPV of the 8-lncRNA signature in detecting malignant IPMNs were 77%, 76%, 82%, and 70%, respectively.

TABLE 9

LncRNA expression in malignant (n = 30) versus benign (n = 21) IPMN cases.

| LncRNA | Overall mean | Benign mean | Malignant mean | P value | False Discovery rate | Fold Change |
|---|---|---|---|---|---|---|
| GLIS3-AS1 | 11.7 | 10.6 | 12.4 | 0.005 | 0.120 | 1.2 |
| ANRIL | 11.7 | 10.7 | 12.3 | 0.009 | 0.120 | 1.2 |
| PANDA | 8.4 | 7.0 | 9.3 | 0.016 | 0.141 | 1.3 |
| MEG3 | 10.3 | 9.4 | 10.9 | 0.022 | 0.141 | 1.2 |
| PVT1 | 12.2 | 11.6 | 12.6 | 0.037 | 0.141 | 1.1 |
| ADARB2-AS1 | 10.4 | 9.8 | 10.8 | 0.039 | 0.141 | 1.1 |
| LINC00472 | 10.4 | 9.6 | 10.9 | 0.039 | 0.141 | 1.1 |
| UCA1 | 12.1 | 11.4 | 12.6 | 0.041 | 0.141 | 1.1 |
| PPP3CB | 13.5 | 13.1 | 13.8 | 0.058 | 0.176 | 1.1 |
| LINC00469 | 9.6 | 8.7 | 10.3 | 0.099 | 0.277 | 1.2 |
| LINC00491 | 9.9 | 9.2 | 10.5 | 0.133 | 0.337 | 1.1 |
| TERC | 9.2 | 8.7 | 9.5 | 0.153 | 0.355 | 1.1 |
| AS1DHRS4 | 13.4 | 13.0 | 13.7 | 0.183 | 0.365 | 1.0 |
| MALAT1 | 10.7 | 10.4 | 11.0 | 0.198 | 0.365 | 1.1 |
| H19 | 15.0 | 14.6 | 15.2 | 0.206 | 0.365 | 1.0 |
| PTENP1 | 6.5 | 5.8 | 6.9 | 0.209 | 0.365 | 1.2 |
| GAS5 | 15.2 | 14.9 | 15.4 | 0.240 | 0.379 | 1.0 |
| HOXD-AS1 | 7.1 | 6.6 | 7.4 | 0.245 | 0.379 | 1.1 |
| BCYRN1 | 0.2 | 0.4 | 0.1 | 0.336 | 0.506 | 0.1 |
| HULC | 2.1 | 1.5 | 2.5 | 0.395 | 0.531 | 1.6 |
| HOTAIR | 6.5 | 6.3 | 6.7 | 0.400 | 0.531 | 1.1 |
| XIST | 0.9 | 0.7 | 1.1 | 0.537 | 0.683 | 1.6 |
| LINC00244 | 0.9 | 0.7 | 1.0 | 0.594 | 0.690 | 1.4 |
| SRA | 5.5 | 5.4 | 5.6 | 0.624 | 0.690 | 1.0 |
| DDX6P | 2.9 | 2.6 | 3.1 | 0.632 | 0.690 | 1.2 |
| lncRNA-p21 | 5.9 | 5.7 | 6.0 | 0.642 | 0.690 | 1.0 |
| HOTTIP | 5.8 | 5.6 | 6.0 | 0.668 | 0.693 | 1.1 |
| aHIF | 9.6 | 9.6 | 9.5 | 0.849 | 0.849 | 1.0 |

Relationship Between Standard Clinical and Radiologic Data, IPMN Pathology, and lncRNA Expression Clinical factors associated (p<0.05) with an increased risk of malignancy included cyst size greater >3 cm (OR (95% CI)=2.60 (0.76-8.86, p=0.127), main duct involvement (OR (95% CI)=11.00 (2.26-53.63, p=0.003), and serum albumin levels (OR (95% CI)=0.35 (0.11-1.15, p=0.083). Cyst size positively correlated with the 8-lncRNA signature (Spearman correlation=0.243, p=0.125), while serum albumin levels negatively correlated with the 8-lncRNA signature (Spearman correlation=−0.158, p=0.356). Mean serum CA 19-9 levels were higher in the malignant compared to benign group, but the difference was not statistically significant (p=0.130). The 8-lncRNA signature was independently associated with malignant status after adjustment for MD involvement (p=0.033).

Combining lncRNA Data with miRNA and Radiomic Data

The inventors evaluated the possibility of using a multi-modal approach to predict IPMN pathology that combines a 5-miRNA signature and a 14-feature radiomic CT signature generated using previously described procedures[27] (see methods). It was shown that a model which integrates miRNA and radiomic data had an area under the curve (AUC) value of 0.92 in discriminating 18 malignant from 20 benign cases; this was far superior to the AUC value for standard radiologic worrisome features (AUC=0.54). In the current investigation, we integrated the 8-lncRNA signature with the 5-miRNA signature and the 14-feature radiomic CT signature and re-assessed diagnostic performance.

Figure 7:
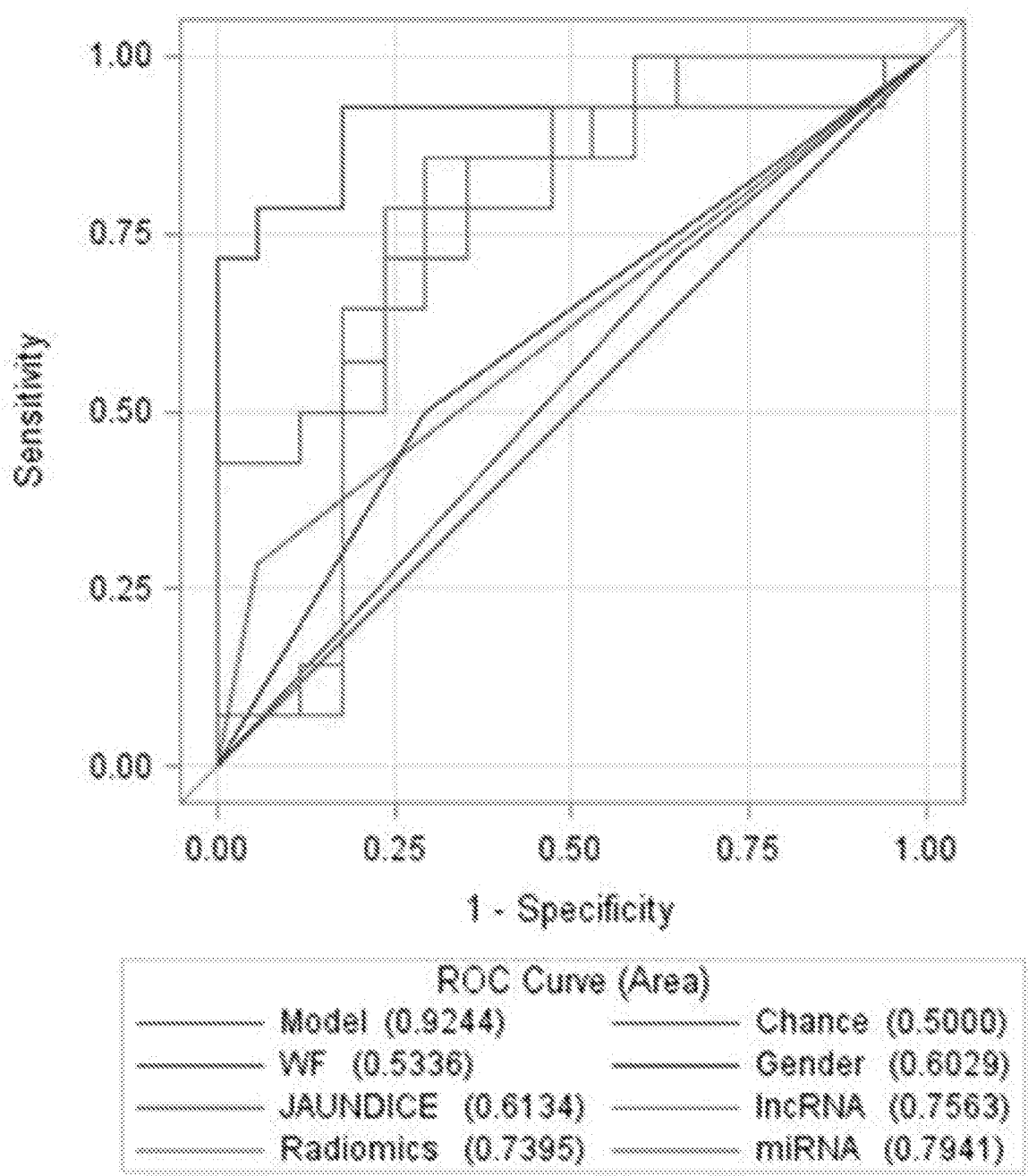
FIG. 7: ROC analysis suggests that genomic data (the 8-lncRNA signature and a 5-miRNA signature) and quantitative radiomic features are more accurate in predicting malignant IPMN pathology than standard worrisome radiologic features and certain demographic and clinical variables. A final model combining the 8-lncRNA signature, the 5-miRNA signature, radiomic features, standard worrisome features (WF), gender, and presence of jaundice has potential to have high accuracy in predicting malignant pathology, with an AUC value approximating 0.92.

Of the 51 IPMN cases represented in the current investigation of lncRNAs, 31 (14 malignant, 17 benign) have available paired pre-operative plasma miRNA data and CT data. As summarized in Table 10, diagnostic performance increased from an AUC value of 0.76 when considering the 8-lncRNA signature alone to 0.90 when combining the 8-lncRNA signature, the 5-miRNA signature, and the 14-feature radiomic signature due to an increase in specificity. Finally, by incorporating standard radiologic features (worrisome features in the absence of high risk stigmata), gender, and presence of jaundice, the AUC increased to 0.92 (95% CI: 0.82-1.00) and revealed estimates of sensitivity, specificity, PPV and NPV of 93%, 82%, 81%, and 93%, respectively (FIG. 7 and Table 10). As anticipated, models that considered presence of high-risk stigmata individually or in conjunction with other data types performed well.

Cross-Validation Analysis

Evaluation of uncertainty by 10-fold cross-validation showed fairly robust estimates of diagnostic performance with AUC above 0.70 for most models that incorporated lncRNAs. A model that combined lncRNAs, miRNAs, radiomics, and worrisome features had an AUC=0.77 (95% CI: 0.68-0.84) in cross-validation and was more accurate than standard demographic (gender), clinical (presence of jaundice), and radiologic variables (worrisome features) in predicting malignant pathology.

Described herein is lncRNA quantification using plasma from individuals newly-diagnosed with commonly detected PDAC precursors known as IPMNs. NCOUNTER technology was used to measure lncRNAs as an alternative to microarray and PCR-based methods to more accurately detect and quantify low lncRNA levels present in blood[46]. Similar to a prior study of circulating miRNAs[22], an extensive quality control and data analysis pipeline was implemented to control for pre-analytical and technical factors that may affect circulating lncRNA levels and result in biases that do not reflect underlying biology. We show that lncRNAs can be detected in plasma, and provide data to support the possibility that this class of noninvasive biomarkers may serve as an adjunct to help predict IPMN severity/pathology.

To evaluate whether lncRNAs may serve as diagnostic markers of PDAC, recent studies[37,39,47-50] have evaluated lncRNA expression in PDAC tumor tissue and adjacent normal tissue, and a few[51,52] have evaluated lncRNA expression in the circulation of PDAC patients, control patients, and healthy individuals using blood[51,53] or saliva[52]. Of the three biofluid-based studies[51,52], only one[51] focused on detection of early-stage PDAC and none studied PDAC

TABLE 10

Diagnostic performance of preliminary models to predict malignant IPMN pathology[1]

| Model/Variables included | AUC (95% CI) | p value | FDR | Accuracy | SE | SP | PPV | NPV |
| --- | --- | --- | --- | --- | --- | --- | --- | --- |
| Gender | 0.60 (0.43~0.78) | 0.242 | 0.252 | 0.61 | 0.50 | 0.71 | 0.58 | 0.63 |
| Jaundice | 0.61 (0.48~0.75) | 0.087 | 0.095 | 0.65 | 0.29 | 0.94 | 0.80 | 0.62 |
| High risk stigmata (HRS) | 0.84 (0.71~0.97) | 0.0002 | 0.004 | 0.84 | 0.86 | 0.82 | 0.80 | 0.88 |
| Worrisome features (WF) | 0.53 (0.36~0.70) | 0.690 | 0.690 | 0.52 | 0.71 | 0.35 | 0.48 | 0.60 |
| lncRNA signature | 0.76 (0.58~0.94) | 0.012 | 0.023 | 0.77 | 0.79 | 0.76 | 0.73 | 0.81 |
| miRNA signature | 0.79 (0.63~0.96) | 0.035 | 0.044 | 0.74 | 0.86 | 0.65 | 0.67 | 0.85 |
| Radiomics signature | 0.74 (0.55~0.93) | 0.014 | 0.024 | 0.77 | 0.86 | 0.71 | 0.71 | 0.86 |
| lncRNAs + Radiomics | 0.78 (0.61~0.95) | 0.010 | 0.022 | 0.81 | 1.00 | 0.65 | 0.70 | 1.00 |
| lncRNAs + miRNAs | 0.83 (0.67~0.99) | 0.013 | 0.024 | 0.81 | 0.79 | 0.82 | 0.79 | 0.82 |
| lncRNAs + Radiomics + miRNAs | 0.90 (0.78~1.00) | 0.004 | 0.011 | 0.87 | 0.71 | 1.00 | 1.00 | 0.81 |
| HRS + WF + lncRNAs | 0.91 (0.81~1.00) | 0.001 | 0.007 | 0.87 | 0.86 | 0.88 | 0.86 | 0.88 |
| HRS + WF + Radiomics | 0.85 (0.70~1.00) | 0.002 | 0.009 | 0.84 | 0.86 | 0.82 | 0.80 | 0.88 |
| HRS + WF + miRNAs | 0.94 (0.87~1.00) | 0.001 | 0.007 | 0.87 | 0.93 | 0.82 | 0.81 | 0.93 |
| HRS + WF + lncRNAs + Radiomics | 0.91 (0.81~1.00) | 0.003 | 0.009 | 0.87 | 0.86 | 0.88 | 0.86 | 0.88 |
| HRS + WF + lncRNAs + miRNAs | 0.95 (0.89~1.00) | 0.001 | 0.007 | 0.87 | 0.93 | 0.82 | 0.81 | 0.93 |
| HRS + WF + lncRNAs + Radiomics + miRNAs | 0.95 (0.89~1.00) | 0.003 | 0.009 | 0.87 | 0.93 | 0.82 | 0.81 | 0.93 |
| HRS + WF + gender + Jaundice + lncRNAs + Radiomics + miRNAs | 0.97 (0.91~1.00) | 0.010 | 0.022 | 0.90 | 0.93 | 0.88 | 0.87 | 0.94 |
| WF + lncRNAs | 0.76 (0.59~0.94) | 0.041 | 0.049 | 0.77 | 0.71 | 0.82 | 0.77 | 0.78 |
| WF + Radiomics | 0.78 (0.60~0.95) | 0.021 | 0.032 | 0.81 | 1.00 | 0.65 | 0.70 | 1.00 |
| WF + miRNAs | 0.79 (0.62~0.96) | 0.067 | 0.076 | 0.81 | 0.79 | 0.82 | 0.79 | 0.82 |
| WF + lncRNAs + Radiomics | 0.82 (0.66~0.97) | 0.015 | 0.025 | 0.77 | 0.86 | 0.71 | 0.71 | 0.86 |
| WF + lncRNAs + miRNAs | 0.84 (0.69~1.00) | 0.029 | 0.039 | 0.84 | 0.86 | 0.82 | 0.80 | 0.88 |
| WF + lncRNAs + Radiomics + miRNAs | 0.92 (0.83~1.00) | 0.007 | 0.020 | 0.87 | 0.93 | 0.82 | 0.81 | 0.93 |
| WF + gender + Jaundice+ lncRNAs + Radiomics + miRNAs | 0.92 (0.82~1.00) | 0.027 | 0.038 | 0.87 | 0.93 | 0.82 | 0.81 | 0.93 |

[1]31 IPMN cases (17 benign; 14 malignant) had data types (clinical data, miRNA, radiomic, lncRNA) included in these analyses.

FDR = false discovery rate; AUC = area underneath the curve; SE = sensitivity; SP = specificity; PPV = positive predictive value; NPV = negative predictive value; "High risk stigmata = main pancreatic duct involvement/dilatation > 10 mm, obstructive jaundice with a cystic lesion in the pancreatic head, or an enhanced solid component/nodule within the cyst; Worrisome features = main pancreatic duct dilation 5-9 mm, cyst size > 3 cm, thickened enhanced cyst walls, non-enhanced mural nodules, or acute pancreatitis"

precursors. Hence, lncRNA signatures derived from tissues, blood, or other biofluids from patients with IPMNs is innovative. Using plasma, the inventors show that two lncRNAs (GAS5 and SRA) can partially discriminate IPMN cases from non-diseased controls (AUC)=0.73 (95% CI: 0.61-0.85, p=0.004). GAS5 (growth arrest-specific 5) was found to have lower expression in IPMN cases compared to controls (p=0.028), consistent with data[33] showing that GAS5 expression is significantly decreased in pancreatic cancer tissues compared with normal pancreatic tissues. The authors[33] demonstrate that GAS5 inhibition induces a significant decrease in G0/G1 phase and an increase in S phase, whereas overexpression in PDAC cells inhibits cell proliferation by negatively regulating CDK6 (cyclin-dependent kinase 6) expression in vitro and in vivo. Furthermore, a recent study showed that decreased GAS5 levels in serum were associated with type 2 diabetes in a cohort of US military veteran[54], suggesting this lncRNA may help to identify individuals 'at-risk' for diabetes. GAS5 expression was not associated with presence of diabetes among IPMN cases in our small dataset (p=0.36), but given that diabetes is an established risk factor for PDAC and 'new-onset' diabetes may serve as a potential marker of early PDAC[55], further research may be indicated to explore a possible role for GAS5 in the molecular pathogenesis of diabetes-mediated PDAC. SRA (steroid receptor RNA activator) is responsible for coordinating functions of transcription factors and enhancing steroid receptor-dependent gene expression[56]. Specifically, as a nuclear receptor coactivator, SRA can coactivate androgen receptor (AR), estrogen receptor alpha (ERalpha), ERbeta, progesterone receptor (PR), glucocorticoid receptor (GR), thyroid hormone receptor and retinoic acid receptor (RAR). Emerging studies have revealed that SRA plays a key role in biological processes (such as myogenesis and steroidogenesis) and pathological changes (such as obesity and tumorigenesis)[56,57]. Thus, it is biologically plausible SRA could be expressed at higher levels in IPMNs compared to normal controls. Moreover, in our dataset, patients with malignant IPMNs had higher levels of SRA than those with benign IPMNs. Further investigation is needed in larger cohorts before conclusions can be reached.

Analysis also revealed an 8-lncRNA signature (comprising ADARB2-AS1, ANRIL, GLIS3-AS1, LINC00472, MEG3, PANDA, PVT1, and UCA1) that partially discriminates between malignant and benign IPMNs AUC=0.77 (95% CI: 0.62-0.92, p=0.006). These lncRNAs were upregulated in malignant compared to benign cases. Consistent with our findings, several of the identified lncRNAs (UCA1, PVT1) appear to have oncogenic functions in pancreatic carcinogenesis[47,48,52,53], inferring biological plausibility of the 8-lncRNA signature. Urothelial cancer-associated 1 (UCA1) is known for its role in bladder cancer progression and embryologic development, and in two separate investigations[47,48] has recently been shown to be upregulated in PDAC tissues (versus matched adjacent normal pancreas tissue), to be associated with several prognostic factors (such as stage, tumor size, and grade), and shorter survival. Furthermore, functional experiments have shown that UCA1 promotes invasion and proliferation of PDAC cells and that down-regulation of UCA1 inhibits cell proliferation and induces apoptosis and cell cycle arrest[47,48]. PVT1 (plasmacytoma variant translocation 1) has been shown to be upregulated in PDAC tissues, to be correlated with clinical stage and poor survival, to be overexpressed in the saliva of PDAC cases versus healthy controls, and to contribute to susceptibility to PDAC as part of a genome-wide association study[53,54,58,60,56]. Furthermore, PVT1 has been identified as a regulator of gemcitabine sensitivity; PVT1 inactivation led to enhanced gemcitabine sensitivity in human PDAC cells[59]. Thus, in addition to serving as prognostic markers and therapeutic targets, it is biologically plausible that UCA1 and PVT1 may also contribute to early pancreatic carcinogenesis (and malignant potential) as observed in this study. ANRIL (antisense non-coding RNA in the INK4 locus) was also shown to have higher expression in malignant versus benign IPMNs. Although we are unaware of reports of ANRIL dysregulation and PDAC, increased expression of this well-known lncRNA has been shown to contribute to the risk of diabetes[60], a risk factor for PDAC[55] and IPMNs[61].

Several of the lncRNAs highlighted in our investigation appear to have a tumor suppressor role in pancreatic neoplasms. For example, maternally expressed gene 3 (MEG3) was recently shown to inhibit PDAC proliferation via activation of p53 and to play a key role in the anti-tumor effects of fenofibrate, a PPAR-α agonist[62]. Additionally, epigenetic activation of MEG3 (and inactivation of its target c-MET) with DNA methylating drugs has been shown to have a therapeutic effect on pancreatic neuroendocrine tumors[63]. Analyses in breast[64] and ovarian tumors[65] support a tumor suppressor role for intergenic lncRNA, LINC00472, but functional investigations of this gene are lacking. A recent phenome-genome association study of pancreatic cancer[66] revealed several open reading frames associated with pancreatic neoplasms, and included candidates LINC00472, GLI3-AS1, and ADARB2-AS1. Finally, although reports of the candidate lncRNA PANDA (P21 associated noncoding RNA DNA damage-activated) and PDAC are lacking, data suggest it plays a role in stabilizing p53 in response to DNA damage[67] and in regulating senescence[68].

To increase diagnostic performance, we combined the 8-lncRNA signature with a 5-miRNA plasma signature, 'radiomic' imaging features, and clinical characteristics available through previous studies[22,27]. We showed that integration of multiple data types improves prediction of IPMN pathology beyond that provided by standard clinical and radiologic characteristics, especially worrisome features considered in consensus guidelines[10]. Although model overfitting may have contributed to our findings and warrants further interrogation in larger datasets, results of the cross-validation analysis suggest that these novel data types do have potential to add value in IPMN risk assessment.

Given that lncRNAs are typically expressed at low concentrations in circulation, we used the robust nCounter platform (as opposed to quantitative real time RT-PCR as others have done) and performed a pre-amplification procedure at the suggestion of the manufacturer and available literature. Although pre-amplification has potential to introduce amplification bias or assay cartridge saturation, head-to-head comparisons of plasma samples with and without pre-amplification have shown a higher level of linearity in samples with pre-amplification[40]. Furthermore, circulating lncRNAs have been shown to be stable under different experimental conditions[40]. Although mechanisms accounting for lncRNA stability are incompletely understood, data suggest they may be protected by exosome encapsulation and/or complex formation with proteins and miRNAs[38,69]. Thus, integrity of our findings may not have been significantly influenced by pre-amplification or sample instability. Our study is also limited in that we evaluated only 28 candidate lncRNAs. It is possible that lncRNAs not evaluated here (such as Linc-pint, a lncRNA observed in plasma to be a possible biomarker of early PDAC by Li et al[51]) could be important to IPMN pathogenesis.

Plasma is now being collected and processed pre- and post-surgery and during surveillance so that we can assess changes in biomarker levels over time. Due to the small or focal nature of IPMNs and the lack of ample tissue for molecular analyses for most cases, tissue microarrays (rather than whole sections) are being created to perform in situ hybridization for the most promising lncRNAs. Finally, the relatively small sample size of our study population limits the ability to draw meaningful conclusions. External validation in a large, multi-center prospective investigation of serial plasma lncRNA measurements is indicated for individuals newly-diagnosed with various types of pancreatic cysts and early-stage PDAC and those at high genetic risk for developing PDAC.

In summary, lncRNAs can be detected in plasma and may be used as part of a blood-based diagnostic adjunct to aid in IPMN management, especially in conjunction with other types of biomarkers (such as miRNAs) and quantitative radiologic features. Large-scale studies with rigorous designs and incorporation of epidemiologic and clinical data are needed to further explore the potential for circulating lncRNAs to be utilized as novel biomarkers for IPMN diagnosis and monitoring and as targets for intervention using RNA interference (RNA-i)-mediated approaches.

REFERENCES

1 American Cancer Society. Cancer Facts and Figures 2017. Atlanta: American Cancer Society. (2017).
2 Szajda, S. D., Waszkiewicz, N., Chojnowska, S. & Zwierz, K. Carbohydrate markers of pancreatic cancer. Biochem Soc Trans 39, 340-343, doi:10.1042/bst0390340 (2011).
3 Adsay N V, F. N., Furukawa T, Hruban R H, Klimstra D S, Kloppel G, et al, Intraductal Papillary Mucinous Neoplasm of the Pancreas. In: Bosman F T, Carneiro F, Hruban R H, Theise N D, editors. WHO classification of tumors of the digestive system. Lyon: WHO Press; 2010. p. 304-313.
4 Megibow, A. J., Baker, M. E., Gore, R. M. & Taylor, A. The incidental pancreatic cyst. Radiol Clin North Am 49, 349-359, doi:10.1016/jscl.2010.10.008 (2011).
5 Farrell, J. J. Prevalence, Diagnosis and Management of Pancreatic Cystic Neoplasms: Current Status and Future Directions. Gut and liver 9, 571-589, doi:10.5009/gnl15063 (2015).
6 Sachs, T., Pratt, W. B., Callery, M. P. & Vollmer, C. M., Jr. The incidental asymptomatic pancreatic lesion: nuisance or threat? J Gastrointest Surg 13, 405-415, doi:10.1007/s11605-008-0788-0 (2009).
7 Matthaei, H., Schulick, R. D., Hruban, R. H. & Maitra, A. Cystic precursors to invasive pancreatic cancer. Nat Rev Gastroenterol Hepatol 8, 141-150, doi:10.1038/nrgastro.2011.2 (2011).
8 Hines, O. J. & Reber, H. A. Pancreatic surgery. Curr Opin Gastroenterol 24, 603-611, doi:10.1097/MOG.0b013e32830b112e (2008).
9 Koh, Y. X. et al. Systematic review and meta-analysis of the spectrum and outcomes of different histologic subtypes of noninvasive and invasive intraductal papillary mucinous neoplasms. Surgery 157, 496-509, doi:10.1016/j.surg.2014.08.098 (2015).
10 Tanaka, M. et al. International consensus guidelines 2012 for the management of IPMN and MCN of the pancreas. Pancreatology 12, 183-197, doi:10.1016/j.pan.2012.04.004 (2012).
11 Panarelli, N. C. et al. Commercial molecular panels are of limited utility in the classification of pancreatic cystic lesions. Am J Surg Pathol 36, 1434-1443, doi:10.1097/PAS.0b013e31825d534a (2012).
12 Kim, K. W. et al. Imaging features to distinguish malignant and benign branch-duct type intraductal papillary mucinous neoplasms of the pancreas: a meta-analysis. Ann Surg 259, 72-81, doi:10.1097/SLA.0b013e31829385f7 (2014).
13 Roch, A. M. et al. International Consensus Guidelines parameters for the prediction of malignancy in intraductal papillary mucinous neoplasm are not properly weighted and are not cumulative. HPB: the official journal of the International Hepato Pancreato Biliary Association 16, 929-935, doi:10.1111/hpb.12305 (2014).
14 Sahora, K. et al. Branch duct intraductal papillary mucinous neoplasms: does cyst size change the tip of the scale? A critical analysis of the revised international consensus guidelines in a large single-institutional series. Ann Surg 258, 466-475, doi:10.1097/SLA.0b013e3182a18f48 (2013).
15 Fritz, S. et al. Pancreatic main-duct involvement in branch-duct IPMNs: an underestimated risk. Ann Surg 260, 848-855; discussion 855-846, doi:10.1097/sla.0000000000000980 (2014).
16 Goh, B. K. et al. Utility of the sendai consensus guidelines for branch-duct intraductal papillary mucinous neoplasms: a systematic review. J Gastrointest Surg 18, 1350-1357, doi:10.1007/s11605-014-2510-8 (2014).
17 Xi, Y. et al. Systematic analysis of microRNA expression of RNA extracted from fresh frozen and formalin-fixed paraffin-embedded samples. Rna 13, 1668-1674, doi:10.1261/rna.642907 (2007).
18 Li, J. et al. Comparison of miRNA expression patterns using total RNA extracted from matched samples of formalin-fixed paraffin-embedded (FFPE) cells and snap frozen cells. BMC Biotechnol 7, 36 (2007).
19 Mostert, B., Sieuwerts, A. M., Martens, J. W. & Sleijfer, S. Diagnostic applications of cell-free and circulating tumor cell-associated miRNAs in cancer patients. Expert Rev Mol Diagn 11, 259-275, doi:10.1586/erm.11.11 (2011).
20 Cortez, M. A. et al. MicroRNAs in body fluids—the mix of hormones and biomarkers. Nat Rev Clin Oncol 8, 467-477, doi:10.1038/nrclinonc.2011.76 (2011).
21 Shi, X., Sun, M., Liu, H., Yao, Y. & Song, Y. Long non-coding RNAs: A new frontier in the study of human diseases. Cancer Lett, doi:10.1016/j.canlet.2013.06.013 (2013).
22 Permuth-Wey, J. et al. Plasma MicroRNAs as Novel Biomarkers for Patients with Intraductal Papillary Mucinous Neoplasms of the Pancreas. Cancer Prev Res (Phila), doi:10.1158/1940-6207.capr-15-0094 (2015).
23 Permuth-Wey, J. et al. A Genome-Wide Investigation of MicroRNA Expression Identifies Biologically-Meaningful MicroRNAs That Distinguish between High-Risk and Low-Risk Intraductal Papillary Mucinous Neoplasms of the Pancreas. PLoS One 10, e0116869, doi:10.1371/journal.pone.0116869 (2015).
24 Li, A. et al. MicroRNA Array Analysis Finds Elevated Serum miR-1290 Accurately Distinguishes Patients with Low-Stage Pancreatic Cancer from Healthy and Disease Controls. Clin Cancer Res, doi:10.1158/1078-0432.ccr-12-3092 (2013).
25 Lubezky, N. et al. MicroRNA expression signatures in intraductal papillary mucinous neoplasm of the pancreas. Surgery 153, 663-672, doi:10.1016/j.surg.2012.11.016 (2013).

26 Matthaei, H. et al. miRNA biomarkers in cyst fluid augment the diagnosis and management of pancreatic cysts. Clin Cancer Res 18, 4713-4724, doi:10.1158/1078-0432.ccr-12-0035 (2012).

27 Permuth, J. B. et al. Combining radiomic features with a miRNA classifier may improve prediction of malignant pathology for pancreatic intraductal papillary mucinous neoplasms. Oncotarget, doi:10.18632/oncotarget.11768 (2016).

28 Kapranov, P. et al. RNA maps reveal new RNA classes and a possible function for pervasive transcription. Science (New York, N.Y.) 316, 1484-1488, doi:10.1126/science.1138341 (2007).

29 Gibb, E. A., Brown, C. J. & Lam, W. L. The functional role of long non-coding RNA in human carcinomas. Molecular cancer 10, 38, doi:10.1186/1476-4598-10-38 (2011).

30 Guil, S. & Esteller, M. Cis-acting noncoding RNAs: friends and foes. Nat Struct Mol Biol 19, 1068-1075, doi:10.1038/nsmb.2428 (2012).

31 Li, J. et al. Long non-coding RNAs expressed in pancreatic ductal adenocarcinoma and lncRNA BC008363 an independent prognostic factor in PDAC. Pancreatology 14, 385-390, doi:10.1016/j.pan.2014.07.013 (2014).

32 Liu, J. H., Chen, G., Dang, Y. W., Li, C. J. & Luo, D. Z. Expression and prognostic significance of lncRNA MALAT1 in pancreatic cancer tissues. Asian Pacific journal of cancer prevention: APJCP 15, 2971-2977 (2014).

33 Lu, X. et al. Downregulation of gas5 increases pancreatic cancer cell proliferation by regulating CDK6. Cell and tissue research 354, 891-896, doi:10.1007/s00441-013-1711-x (2013).

34 Pang, E. J., Yang, R., Fu, X. B. & Liu, Y. F. Overexpression of long non-coding RNA MALAT1 is correlated with clinical progression and unfavorable prognosis in pancreatic cancer. Tumour biology: the journal of the International Society for Oncodevelopmental Biology and Medicine, doi:10.1007/s13277-014-2850-8 (2014).

35 Peng, W., Gao, W. & Feng, J. Long noncoding RNA HULC is a novel biomarker of poor prognosis in patients with pancreatic cancer. Medical oncology (Northwood, London, England) 31, 346, doi:10.1007/s12032-014-0346-4 (2014).

36 Sun, Y. W. et al. A novel long non-coding RNA ENST00000480739 suppresses tumour cell invasion by regulating OS-9 and HIF-1alpha in pancreatic ductal adenocarcinoma. Br J Cancer 111, 2131-2141, doi:10.1038/bjc.2014.520 (2014).

37 Tahira, A. C. et al. Long noncoding intronic RNAs are differentially expressed in primary and metastatic pancreatic cancer. Molecular cancer 10, 141, doi:10.1186/1476-4598-10-141 (2011).

38 Kishikawa, T. et al. Circulating RNAs as new biomarkers for detecting pancreatic cancer. World journal of gastroenterology: WJG 21, 8527-8540, doi:10.3748/wjg.v21.i28.8527 (2015).

39 Zhou, M. et al. Construction and analysis of dysregulated lncRNA-associated ceRNA network identified novel lncRNA biomarkers for early diagnosis of human pancreatic cancer. Oncotarget 7, 56383-56394, doi:10.18632/oncotarget.10891 (2016).

40 Arita, T. et al. Circulating long non-coding RNAs in plasma of patients with gastric cancer. Anticancer research 33, 3185-3193 (2013).

41 Isin, M. et al. Investigation of circulating lncRNAs in B-cell neoplasms. Clinica chimica acta; international journal of clinical chemistry 431, 255-259, doi:10.1016/j.cca.2014.02.010 (2014).

42 Ren, S. et al. Long non-coding RNA metastasis associated in lung adenocarcinoma transcript 1 derived miniRNA as a novel plasma-based biomarker for diagnosing prostate cancer. Eur J Cancer 49, 2949-2959, doi:10.1016/j.ejca.2013.04.026 (2013).

43 Wu, Y. et al. A serum-circulating long noncoding RNA signature can discriminate between patients with clear cell renal cell carcinoma and healthy controls. Oncogenesis 5, e192, doi:10.1038/oncsis.2015.48 (2016).

44 Xie, H., Ma, H. & Zhou, D. Plasma HULC as a Promising Novel Biomarker for the Detection of Hepatocellular Carcinoma. BioMed research international 2013, 136106, doi:10.1155/2013/136106 (2013).

45 Veldman-Jones, M. H. et al. Evaluating Robustness and Sensitivity of the NanoString Technologies nCounter Platform to Enable Multiplexed Gene Expression Analysis of Clinical Samples. Cancer Res 75, 2587-2593, doi:10.1158/0008-5472.can-15-0262 (2015).

46 Schultz, N. A. et al. MicroRNA biomarkers in whole blood for detection of pancreatic cancer. JAMA 311, 392-404, doi:10.1001/jama.2013.284664 (2014).

47 Fu, X. L. et al. Analysis of long non-coding RNA expression profiles in pancreatic ductal adenocarcinoma. Sci Rep 6, 33535, doi:10.1038/srep33535 (2016).

48 Chen, P. et al. Long non-coding RNA UCA1 promotes the tumorigenesis in pancreatic cancer. Biomedicine & pharmacotherapy=Biomedecine & pharmacotherapie 83, 1220-1226, doi:10.1016/j.biopha.2016.08.041 (2016).

49 Wang, Y. et al. Expression profile of long non-coding RNAs in pancreatic cancer and their clinical significance as biomarkers. Oncotarget 6, 35684-35698, doi:10.18632/oncotarget.5533 (2015).

50 Zhou, Y. et al. Microarray expression profile analysis of long non-coding RNAs in pancreatic ductal adenocarcinoma. International journal of oncology 48, 670-680, doi:10.3892/ijo.2015.3292 (2016).

51 Li, L. et al. Plasma and tumor levels of Linc-pint are diagnostic and prognostic biomarkers for pancreatic cancer. Oncotarget, doi:10.18632/oncotarget.12365 (2016).

52 Xie, Z. et al. Salivary HOTAIR and PVT1 as novel biomarkers for early pancreatic cancer. Oncotarget 7, 25408-25419, doi:10.18632/oncotarget.8323 (2016).

53 Huang, C. S. et al. Increased expression of the lncRNA PVT1 is associated with poor prognosis in pancreatic cancer patients. Minerva medica (2015).

54 Carter, G. et al. Circulating long noncoding RNA GAS5 levels are correlated to prevalence of type 2 diabetes mellitus. BBA clinical 4, 102-107, doi:10.1016/j.bbacli.2015.09.001 (2015).

55 Yeo, T. P. Demographics, epidemiology, and inheritance of pancreatic ductal adenocarcinoma. Seminars in oncology 42, 8-18, doi:10.1053/j.seminoncol.2014.12.002 (2015).

56 Liu, C. et al. Steroid receptor RNA activator: Biologic function and role in disease. Clinica chimica acta; international journal of clinical chemistry 459, 137-146, doi: 10.1016/j.cca.2016.06.004 (2016).

57 Xu, B. et al. Multiple roles for the non-coding RNA SRA in regulation of adipogenesis and insulin sensitivity. PLoS One 5, e14199, doi:10.1371/journal.pone.0014199 (2010).

58 Wolpin, B. M. et al. Genome-wide association study identifies multiple susceptibility loci for pancreatic cancer. Nat Genet 46, 994-1000, doi:10.1038/ng.3052 (2014).
59 You, L., Chang, D., Du, H. Z. & Zhao, Y. P. Genome-wide screen identifies PVT1 as a regulator of Gemcitabine sensitivity in human pancreatic cancer cells. Biochemical and biophysical research communications 407, 1-6, doi: 10.1016/j.bbrc.2011.02.027 (2011).
60 Kong, Y., Sharma, R. B., Nwosu, B. U. & Alonso, L. C. Islet biology, the CDKN2A/B locus and type 2 diabetes risk. Diabetologia 59, 1579-1593, doi:10.1007/s00125-016-3967-7 (2016).
61 Capurso, G. et al. Risk factors for intraductal papillary mucinous neoplasm (IPMN) of the pancreas: a multi-centre case-control study. The American journal of gastroenterology 108, 1003-1009, doi:10.1038/ajg.2013.42 (2013).
62 Hu, D. et al. Fenofibrate inhibited pancreatic cancer cells proliferation via activation of p53 mediated by upregulation of LncRNA MEG3. Biochemical and biophysical research communications 471, 290-295, doi:10.1016/j.bbrc.2016.01.169 (2016).
63 Modali, S. D., Parekh, V. I., Kebebew, E. & Agarwal, S. K. Epigenetic regulation of the lncRNA MEG3 and its target c-MET in pancreatic neuroendocrine tumors. Molecular endocrinology (Baltimore, Md.) 29, 224-237, doi:10.1210/me.2014-1304 (2015).
64 Shen, Y. et al. LINC00472 expression is regulated by promoter methylation and associated with disease-free survival in patients with grade 2 breast cancer. Breast cancer research and treatment 154, 473-482, doi:10.1007/s10549-015-3632-8 (2015).
65 Fu, Y. et al. Long non-coding RNAs, ASAP1-IT1, FAM215A, and LINC00472, in epithelial ovarian cancer. Gynecologic oncology, doi:10.1016/j.ygyno.2016.09.021 (2016).
66 Narayanan, R. Phenome-Genome Association Studies of Pancreatic Cancer: New Targets for Therapy and Diagnosis. Cancer genomics & proteomics 12, 9-19 (2015).
67 Kotake, Y. et al. Long Non-coding RNA, PANDA, Contributes to the Stabilization of p53 Tumor Suppressor Protein. Anticancer research 36, 1605-1611 (2016).
68 Puvvula, P. K. et al. Long noncoding RNA PANDA and scaffold-attachment-factor SAFA control senescence entry and exit. Nature communications 5, 5323, doi: 10.1038/ncomms6323 (2014).
69 Dong, L. et al. Circulating Long RNAs in Serum Extracellular Vesicles: Their Characterization and Potential Application as Biomarkers for Diagnosis of Colorectal Cancer. Cancer epidemiology, biomarkers & prevention: a publication of the American Association for Cancer Research, cosponsored by the American Society of Preventive Oncology 25, 1158-1166, doi:10.1158/1055-9965.epi-16-0006 (2016).
70 Fenstermacher, D. A., Wenham, R. M., Rollison, D. E. & Dalton, W. S. Implementing personalized medicine in a cancer center. Cancer J 17, 528-536, doi:10.1097/PPO.0b013e318238216e (2011).
71 Blondal, T. et al. Assessing sample and miRNA profile quality in serum and plasma or other biofluids. Methods 59, 164-169, doi:10.1016/j.ymeth.2012.09.015 (2013).
72 Kirschner, M. B. et al. The Impact of Hemolysis on Cell-Free microRNA Biomarkers. Front Genet 4, 94, doi:10.3389/fgene.2013.00094 (2013).
73 Smyth, G. K. Linear models and empirical bayes methods for assessing differential expression in microarray experiments. Stat Appl Genet Mol Biol 3, Article3, doi:10.2202/1544-6115.1027 (2004).
74 Chen, D. T. et al. Prognostic and predictive value of a malignancy-risk gene signature in early-stage non-small cell lung cancer. Journal of the National Cancer Institute 103, 1859-1870, doi:10.1093/jnci/djr420 (2011).
75 Chen, D. T. et al. Proliferative genes dominate malignancy-risk gene signature in histologically-normal breast tissue. Breast cancer research and treatment 119, 335-346, doi:10.1007/s10549-009-0344-y (2010).
76 Marchion, D. C. et al. BAD phosphorylation determines ovarian cancer chemosensitivity and patient survival. Clinical cancer research: an official journal of the American Association for Cancer Research 17, 6356-6366, doi:10.1158/1078-0432.CCR-11-0735 (2011).
77 Hopewell, E. L. et al. Lung tumor NF-kappaB signaling promotes T cell-mediated immune surveillance. The Journal of clinical investigation, doi:10.1172/JCI67250 (2013).
78 Youden, W. J. Index for rating diagnostic tests. Cancer 3, 32-35 (1950).
79 Benjamini, Y. H., Y. Controlling the False Discovery Rate: a Practical and Powerful Approach to Multiple Testing. Journal of the Royal Statistical Society B 57, 289-300 (1995).

Example 4—Combining Radiomic Features with an miRNA Classifier to Improve Prediction of Malignant Pathology for Pancreatic IPMNs IPMNs are pancreatic cancer precursors incidentally discovered by cross-sectional imaging. Consensus guidelines for IPMN management rely on standard radiologic features to predict pathology, but they lack accuracy. Using a retrospective cohort of 38 surgically-resected, pathologically-confirmed IPMNs (20 benign; 18 malignant) with preoperative computed tomography (CT) images and matched plasma-based 'miRNA genomic classifier (MGC)' data, we determined whether quantitative "radiomic" CT features (+/− the MGC) can more accurately predict IPMN pathology than standard radiologic features "high-risk" or "worrisome" for malignancy. Logistic regression, principal component analyses, and cross-validation were used to examine associations. Sensitivity, specificity, positive and negative predictive value (PPV, NPV) were estimated. The MGC, "high-risk", and "worrisome" radiologic features had area under the receiver operating characteristic curve (AUC) values of 0.83, 0.84, and 0.54, respectively. Fourteen radiomic features differentiated malignant from benign IPMNs ($p<0.05$) and collectively had an AUC=0.77. Combining radiomic features with the MGC revealed an AUC=0.92 and superior sensitivity (83%), specificity (89%), PPV (88%), and NPV (85%) than other models. Evaluation of uncertainty by 10-fold cross-validation retained an AUC>0.80 (0.87 (95% CI: 0.84-0.89)). This proof-of-concept study suggests a noninvasive radiogenomic approach may more accurately predict IPMN pathology than "worrisome" radiologic features considered in consensus guidelines.

To revolutionize the early detection of cancer, there is a need to replace invasive and risky tissue biopsies not representative of the entire tumor with noninvasive tests reflecting the tumor and its environment. Such a discovery is sorely needed for pancreatic ductal adenocarcinoma (PC), the deadliest of the leading causes of cancer death in the United States, with a five-year survival rate of only 8% [1,2]. PC is currently the third leading cause of cancer death, and is projected to become the second leading cause around 2020. Most cases (85%) present with metastases because of the lack of accurate methods to detect disease at an early, operable stage [1]. The detection and treatment of precursor lesions offers great promise for reducing morbidity and mortality.

IPMNs are PC precursors accounting for nearly half of the 150,000 asymptomatic pancreatic cysts detected incidentally in up to 2.6% of computed tomography (CT) scans and 19.9% of magnetic resonance imaging (MM) studies each year [2,3]. IPMNs are challenging to manage due to the inability to predict which lesions can be safely monitored, which may progress to invasion, and which have associated invasion [3]. The only way to treat IPMNs and examine severity (which ranges from low- and moderate-grade dysplasia to high-grade dysplasia and invasive carcinoma) is through surgical resection and pathological evaluation. However, pancreatic resection is associated with an operative mortality of 2-4% and morbidity of 40-50% [4]. One clue regarding histologic severity can be obtained radiologically by investigating whether the IPMN(s) present within the main pancreatic duct (MD-IPMN), side branch ducts (BD-IPMN), or both (mixed-IPMN); surgical series confirm that IPMNs with MD involvement harbor a higher risk of malignancy (~60%, range: 11-81%) and more rapid growth compared to BD-IPMNs (26%, range: 6-47%) [5]. Consensus guidelines for IPMN management known as "Sendai guidelines" exist [5] and rely on standard radiographic and clinical features. These guidelines [5] suggest that patients with "high risk stigmata" (MD involvement/dilatation ≥10 mm, obstructive jaundice with a cystic lesion in the pancreatic head, or an enhanced solid component/nodule within the cyst) undergo resection, as most harbor high-grade or invasive disease [5]. On the other hand, it is recommended that presumed BD-IPMNs with "worrisome features" (MD dilation 5-9 mm, cyst size ≥3 cm, thickened enhanced cyst walls, non-enhanced mural nodules, or acute pancreatitis) undergo surveillance with an invasive endoscopic ultrasound-guided fine needle aspirate (EUS-FNA) procedure despite poor sensitivity and technical complications [3,6]. Although the consensus guidelines provide a valuable framework for management, the agreement between the preoperative diagnosis and pathologic examination is inaccurate in a substantial proportion (30-70%) of cases [5,7-11]. Thus, novel markers of malignant pathology are needed, especially for cases that do not appear to present with high-risk stigmata.

miRNAs are excellent candidate biomarkers of pancreatic tumorigenesis because of their tissue-specific expression, stability in biofluids, and their ability to regulate hundreds of genes and biological pathways [12]. We recently conducted genome-wide miRNA analysis using tissue [13] and blood plasma [14] from a cohort of 42 patients with surgically-resected, pathologically-confirmed IPMNs. Our unbiased analysis of 800 miRNAs from archived plasma using Nanostring's NCOUNTER digital technology [14] revealed a 5-miRNA genomic classifier (MGC) that included miR-200a-3p, miR-1185-5p, miR-33a-5p, miR-574-4p, and miR-664b and discriminated between 21 malignant (classified as high-grade or invasive) and 21 benign IPMNs (classified as low- or moderate-grade) (p=0.005, area under the receiver operating characteristic curve (AUC)=0.73 (95% CI: 0.58-0.89). These miRNAs had 2-3 fold lower expression in malignant compared to benign cases, supporting a tumor suppressor role. Recent studies of other cancers [15, 16] suggest the ability to predict lesion severity may improve further by combining genomic data with quantitative radiologic features.

Radiomics refers to the high-throughput extraction and analysis of quantitative features from standard-of-care medical images with the intent of generating mineable databases that can be used to build predictive models relating imaging features (or "radiophenotypes") to clinical outcomes [17]. Categories of radiomic features such as tumor signal intensity, shape characterization, and texture have the following advantages over and/or provide enhancements to standard radiologic features [18-24]: they i.) represent quantitative, objective measures, ii.) reflect tumor heterogeneity and sub-regional habitats, iii.) can be more strongly linked to clinical outcomes, iv.) can be more reproducible and stable, [22] and v.) can improve diagnostic accuracy when combined with standard radiologic features [22,36].

The inventors hypothesized that adopting a radiomic approach could enhance preoperative prediction of IPMN malignancy (either alone or in combination with the MGC) by uncovering diagnostic and biologic information "hidden" in routinely acquired images. CTs are the most widely used imaging modality in oncology and have emerged as a preferred modality for the detection and characterization of pancreatic cysts because of its widespread availability, high spatial and temporal resolution, short scanning duration, high-quality multiplanar image display [25], and similar accuracy as MRIs for characterizing pancreatic cysts as benign or malignant [26]. Radiomics evaluations of pre-treatment CT scans have been conducted by our team [19,21,22,24,27] and others [18,28-32], with associations reported between radiophenotypes and clinical outcomes. Moreover, "radiogenomics" approaches have been used to link imaging features to underlying genomic information [15,33-39]. The goal of this study was to determine whether radiomic features extracted from preoperative CT scans, either alone or with miRNA data, may improve prediction of IPMN pathology beyond that provided by standard radiologic or clinical features encompassed by current consensus guidelines [5].

Materials & Methods

Study Population and Data

A prospectively maintained clinical database was retrospectively reviewed to identify individuals who underwent a pancreatic resection for an IPMN between 2006 and 2011 at Moffitt Cancer Center and Research Institute (Moffitt) and had provided written consent for blood, imaging, and clinical data to be donated pre-operatively for research through protocols approved by the Institutional Review Board (IRB) of the University of South Florida, including Total Cancer Care [47]. IRB approval was granted for the research described herein (IRB #Pro4971). For all cases, demographic and clinical data (presenting systems, age at diagnosis, past medical and surgical history, current and past medication use, and information on a uniform set of known and suspected cancer risk factors such as smoking and alcohol history, family history, and body mass index) was obtained from the electronic medical record and patient questionnaire. Detailed imaging studies, surgical details, pathology results, lab values (serum CA-19-9, bilirubin, albumin), and treatment information was collected from the medical record and Moffitt's Cancer Registry.

Histopathologic Analysis

Pathologists with expertise in PDAC and IPMN pathology (KJ, DC, BAC) used hematoxylin and eosin (H&E)

stained slides from selected blocks to histologically confirm the diagnosis and degree of dysplasia using World Health Organization guidelines [48]. The final diagnosis represented the most severe grade of dysplasia observed in the neoplastic epithelium. None of the cases received preoperative chemotherapy or radiation. "Malignant" cases were defined by high-grade dysplasia or invasive carcinoma and 'benign' cases were defined by low- or moderate-grade dysplasia.

miRNA Expression Data

Preoperative plasma miRNA expression data was previously generated [14] for 42 surgically-resected, pathologically-confirmed IPMN cases (21 malignant and 21 benign). Briefly, one 0.5-mL cryovial of plasma was retrieved and thawed for each identified case. To control for variance in starting material and efficiency of RNA extraction, RNA spike-in miRNAs (synthetic control templates) were used. Total RNA isolation was performed on 500 uL of plasma using the Plasma/Serum Circulating and Exosomal RNA Purification Mini Kit (Slurry Format) from Norgen Biotek (Ontario, Canada), and total RNA concentration and integrity was assessed using the NanoDrop spectrophotometer (NanoDrop Technologies, Waltham, MA) and an Agilent Bioanalyzer (Agilent, Santa Clara, CA). Since hemolysis can confound studies of plasma miRNAs, the possibility of hemolysis was assessed.

The NCOUNTER Human v2 miRNA Expression Assay Codeset (Nanostring Technologies, Seattle, WA, USA) was used to quantify the abundance of a pre-defined panel of 800 human miRNAs and built-in controls. Raw miRNA counts underwent technical and biological normalization and log 2-transformation. The most deregulated miRNAs that differed between the benign and malignant groups were identified using the linear models for microarray data (LIMMA) method and a principal component analysis (PCA) approach (14). Since miRNAs can be over- or under-expressed, we used PCA to combine the most deregulated miRNAs and generate an overall "IPMN-risk score" based on the first principal component (PC1). A focused analysis of the 42 IPMN cases showed that five miRNAs (miR-200a-3p, miR-1185-5p, miR-33a-5p, miR-574-3p, and miR-663b), a miRNA genomic classifier ("MGC"), discriminated between malignant and benign IPMNs (p<0.05). The overall expression of PC1 was lower in malignant compared to benign IPMNs (p=0.005), was significantly associated with malignant status (OR (95% CI): 0.36 (0.16, 0.83), p=0.017), and had an AUC value of 0.73 (95% CI: 0.58-0.89) in discriminating between groups.

CT Imaging

The majority of CT scans from this series of patients were obtained on the Siemens Sensation (16, 40, or 64) using a CT angio (CTA) pancreas protocol (Table 14). Our standard operating procedure includes obtaining 3 mm axial CT slice images of the abdomen from the superior liver capsule to the iliac crests without contrast. Optiray-370 contrast is then injected intravenously at a rate of 3.5 ml/sec. The volume of Optiray-370 contrast injected follows a weight-based scale. Arterial phase imaging is triggered by contrast bolus tracking of the abdominal aorta at a Hounsfield Unit of 100-120. Arterial phase images of the abdomen are obtained ~20 seconds after contrast injection, and venous phase images of the abdomen are obtained ~60 seconds after injection. 3 mm coronal reconstruction images (B30/B31f) of the abdomen are also performed for each phase (noncontrast, arterial phase, venous phase).

CT Acquisition and Feature Selection and Extraction

Preoperative CT images were available for 38 of the 42 surgically-resected, pathologically-confirmed IPMN cases with available matched preoperative miRNA expression data generated in our previous publication [14]. Thus, overlap exists for 38 of the study participants in the current report and our previous publication [14]; the prior article [14] dealt with the development of a miRNA classifier whereas in this manuscript we emphasize standard radiologic features and radiomic features as predictors of IPMN pathology with and without the miRNA classifier. CT images were obtained from Moffitt's GE Centricity Picture Archiving and Communication System (PACS). Most cases underwent contrast-enhanced CTs within 3 months prior to surgery. Our lead radiologist who has over 5 years of experience reviewing IPMN cases (J.C.) and the entire analytic team were blinded to the pathological diagnosis. CT images were reviewed for standard radiologic features encompassing "high-risk stigmata" and "worrisome features" represented in consensus guidelines [5]. The scan reconstruction and central slice was selected by J.C. Axial venous phase images (3 mm) were used for most patients because of the tumor/background contrast. Arterial phase or coronal images were used as needed. In the event multifocal disease was present, we characterized the most concerning cyst that corresponded to one that was ultimately resected. J.C. identified the region of interest (ROI) by helping to outline the peripheral margin of tumors in their entirety, capturing both solid (nodular) and cystic components. The radiomics team then marked the ROI using Definiens/GE AWS Advanced Visualization software. Based on previous successes [19,21], the entire tumors were identified (solid and cystic components) using a semi-manual version of a single click semi-automated ensemble segmentation algorithm within the Definiens Developer XD (Munich, Germany) software platform. Target lesions were segmented, with a second radiologist (Q.L, Resident Radiologist with over 2 years of experience) finalizing the segmentation boundaries on the CT slices. This approach eliminates the need for a manually drawn boundary while providing robust, reproducible, and consistent delineation of the tumor region across CT slices [19,21]. The segmentation algorithm has also been shown to reduce inter-observer variability while capturing intricacies of the tumor boundary [42].

We then extracted categories of non-texture and texture features. Non-texture features measure tumor size (volume, diameter, border length), shape (compactness, asymmetry), and location, whereas texture features measure properties such as smoothness, coarseness, and regularity. We focused on evaluating two-dimensional (2D) quantitative features in the middle CT slice. To minimize analysis problems inherent with testing hundreds of features in a limited sample size, we reduced dimensionality by limiting the number of imaging features to 112. Of the 112 features, 18 were non-textural and 94 were textural (10 histogram in hounsfield units, 27 co-occurrence/run-length, and 57 laws and wavelets). In house algorithms for feature extraction and quantification of segmented regions were implemented by custom routines in the Definiens Platform.

Statistical Analyses

For a selected set of variables, descriptive statistics were calculated using frequencies and percents for categorical variables and means and standard deviations (SD) for continuous variables.

After feature extraction, the Pearson correlation coefficient was used to identify and filter out 55 highly correlated (or redundant) radiomic features, leaving 57 features for analysis. Simple logistic regression models were used to explore associations with IPMN pathology. Principal component analysis (PCA) was also performed to reduce radiomic feature data dimensionality and to generate an index score defined by the first principal component (PC1); PC1 was evaluated for its association with malignant status using logistic regression. The sensitivity, specificity, positive predictive value (PPV), negative predictive value (NPV), and accuracy of the new radiomic features were calculated by estimating the optimal cutpoint using Youden's index [49], with pathological diagnosis as the gold standard. Estimates of diagnostic performance generated from radiomic models were generated with and without the MGC data and were compared to those obtained when evaluating standard radiologic and clinical features [5]. DeLong's test was used to compare the area under correlated ROC curves [50]. To evaluate model performance, repeated (10,000 times) 10-fold cross validation was performed. The average and 95% confidence intervals of accuracy, sensitivity, specificity, PPV and NPV were estimated. In each 10-fold cross-validation, data were split into 10 subsets. By holding one subset of data (test set), the remaining 9 subsets were used as a training set to build a model for prediction evaluation in the test set. The process continued until each subset was used as the test set. By testing the model on a test set (not used in estimation), the cross-validation approach aimed to reduce over-fitting. Although prediction on the test set (treated as new data) would likely increase uncertainty and therefore reduce performance, it provides a great tool to evaluate robustness of the model. Finally, we evaluated if the most statistically significant imaging features were correlated with one another or the MGC using two-sample t-tests or Wilcoxon rank sum tests.

Results

Study Population Characteristics

Selected clinical, epidemiologic, and imaging characteristics of the 38 cases (20 benign; 18 malignant) having matched pre-operative CT and MGC data are in Table 11. Seventy-two percent with malignant pathology had MD involvement on CT vs. 20% with benign pathology (p=0.003). Mean cyst size was lower in the benign compared to the malignant group (2.8 vs. 3.9 cm), p=0.018. Consistent with published data (8, 9, 48), most cases (83%) with malignant pathology had ≥1 "high risk stigmata" (MD involvement/dilatation ≥10 mm, obstructive jaundice with a cystic lesion in the pancreatic head, or an enhanced solid component within the cyst), vs. 15% of those with benign pathology (p<0.001). Having one or more "worrisome" features (i.e., MD dilation 5-9 mm, cyst size ≥3 cm, thickened enhanced cyst walls, non-enhanced mural nodules, or acute pancreatitis) was not associated with malignancy (p=0.73), suggesting surgery may not have been indicated. PC1 of the MGC was significantly lower in the malignant group compared to the benign group (p<0.001).

Analysis of Standard Radiologic and Clinical Characteristics and miRNA Data

Using variables from Table 11, multiple logistic regression analyses revealed that only high risk stigmata and the MGC retained significance (OR (95% CI): 43.0 (4.64-398), p=0.001 and OR (95% CI): 0.30 (0.10-0.86), p=0.026, respectively). The AUC value was 0.95 for the model with both variables, compared to 0.84 and 0.83 for high risk stigmata (p=0.063) and the MGC (p=0.038) individually (FIG. 9).

Since medical management is less clear for the estimated 60% of presumed BD-IPMN cases who have worrisome features (and do not present with high risk stigmata) (5), it was most important that we assess the added value of the MGC in that subset of patients. While worrisome features alone could not predict malignant pathology much better than chance (AUC=0.54), the AUC increased to 0.83 when incorporating the MGC, primarily due to increased specificity. For example, when restricting to the 20 patients who did not present with high-risk stigmata, the specificity of the MGC and worrisome features were 70.6% and 35.3%, respectively. Finally, a model that solely considered demographic and clinical predictors of IPMN pathology highlighted previously (49-53) (age at diagnosis, gender, presence of symptoms) had an AUC (95% CI)=0.73 (0.56-0.89).

Analysis of Radiomic Data

Radiomic features were successfully extracted for 37 of the 38 cases; features could not be extracted for one benign case from an outside hospital because only digitized film was available and there were no coronal views. Univariate analysis of the 112 radiomic CT features revealed 14 features (11 textural, including histogram, wavelet, laws, and co-occurrence/run-length, and 3 non-textural, all size &shape) that differentiated malignant from benign IPMNs (P<0.05) (Table 12). The most statistically significant features were textural and included histogram entropy layer 1 (OR (95% CI): 3.77 (1.34-10.63), p=0.012) and run-length features G1 D0 LGRE Layer 1 (OR (95% CI): 4.30 (1.37-13.49), p=0.013). Statistically significant non-textural features that were associated with an increased likelihood of malignant pathology included border length and width, whereas radius of the largest enclosed ellipse was associated with a decreased likelihood of malignant pathology (Table 12). Collectively, the 14 radiomic features (defined as "Features PC1") had a diagnostic accuracy higher than worrisome features (AUC=0.77 versus 0.54). "Features PC1" explained 61% of the variability in the data, suggesting it represents the 14 most promising radiomic features well. Of clinical importance, there were three cases for whom the final pathology was benign that had worrisome features on preoperative imaging yet were correctly classified as true negatives (benign) via radiomics using the Features PC1 score; thus radiomic features may have helped to avoid overtreatment with surgery. An image from one of these cases is displayed in FIG. 8A. On the other hand, there was one case for whom the final lesion pathology was malignant but there were no high risk stigmata on preoperative imaging (only one worrisome feature of cyst size >3 cm) and radiomics classified the case as a true positive (malignant); thus radiomics may have aided in directing management towards a necessary surgery to remove what turned out to be a high-grade lesion (FIG. 8B).

Integration of Radiomic Data with Other Data Types

A model that combined radiomic features and the MGC had an AUC=0.92 and estimates of sensitivity (83%), specificity (89%), PPV (88%), and NPV (85%) that were superior to models not based on these data types that relied on demographic or standard imaging features alone, particularly worrisome features (Table 13). When integrating standard worrisome radiologic features with radiomic features and the MGC, the diagnostic performance of the model increased further (AUC=0.93 (95% CI: 0.85-1.00) (FIG. 11) than the models based on worrisome features alone (p<0.001) and radiomic PC1 alone (p=0.037), with enhanced estimates of sensitivity, PPV, and NPV, each at 89%. As expected, models that considered presence of high-risk stigmata in conjunction with radiomic data performed well.

Cross-Validation and Correlative Analysis

Evaluation of uncertainty by 10-fold cross-validation showed robust estimates of diagnostic performance with AUC above 0.75 for most models (Table 15). Specifically, a model that combined radiomic features with the MGC had an AUC=0.87 (95% CI: 0.84-0.89) and was more accurate than demographic characteristics and worrisome features at predicting malignant pathology. Finally, preliminary analyses revealed that the radiomic "features PC1" was associated with high risk stigmata (p=0.0009) and worrisome features (p=0.0006), but not with the MGC (P>0.05).

Due to their malignant potential, the identification of an IPMN generates anxiety, the need for subsequent imaging, possible invasive testing or surgery, and huge economic costs (54). Thus, the value of developing a noninvasive, cost-effective approach to accurately distinguish malignant from benign IPMNs cannot be overstated because it would enable individuals with malignant lesions to undergo life-saving surgery while sparing those with benign lesions the inconvenience, morbidity, and cost of major surgery. Here we conducted the first proof-of-concept radiogenomic study to noninvasively evaluate the clinical utility of radiomic features as predictors of malignant IPMNs alone and in combination with a blood-based miRNA genomic classifier discovered by our team [14]. Consistent with data from other cancers which suggest that complementary biomarkers will increase specificity of standard-of-care images [31,40,41], our preliminary data infer that incorporating radiomic and miRNA expression data from images and blood obtained through standard of care has potential to accelerate discovery of a noninvasive multimodal approach to rapidly provide clinically-actionable information to improve pre-operative prediction of IPMN malignancy, especially for patients who do not present with high-risk stigmata. Such an approach would also minimize the potential for sampling bias and risks associated with tissue biopsy-dependent approaches that do not capture tumor heterogeneity.

Radiomics provides a noninvasive, fast, low cost, and repeatable way of investigating quantitative radiophenotypes that may potentially personalize care for patients with pancreatic cancer precursors. After applying a semiautomatic segmentation process that minimizes operator interaction and has been shown to provide accurate and reproducible boundaries [19,21,42], we successfully extracted 112 preoperative CT radiomic features, and revealed 14 features that differentiated malignant from benign IPMNs (p<0.05). Of the 14 features, 11 were textural (histogram, wavelets, laws, or run-length/co-occurrence) and 3 were non-textural and from the size and shape category. Texture of CT scans to a clinical radiologist is usually attributed to gray-level changes seen by the expert whereas texture in traditional image processing refers to the spatial arrangement of color or intensity in a localized region or whole scene. It is of interest that in this and other radiomic investigations [43], the most important characteristics to separate the two clinical outcomes were textural based on run length and co-occurrence (with few others). Interestingly, Hanania et al. (submitted, Oncotarget) recently conducted a study in which they describe the use of quantitative radiomic features for risk stratification of IPMNs. Hanania et al. also identified fourteen top-performing radiomic features (all textural within the gray-level co-occurrence matrix) as differentiating between benign and malignant pathology. Using a cross-validated design, the top-performing logistic regression model yielded an AUC=0.96, with a sensitivity and specificity of 97% and 88%, respectively. Because the study by Hanania et al. does not have matched plasma miRNA data and our groups used different methodology for acquisition, segmentation, feature extraction, and analysis, the opportunity for meaningful independent validation of each other's findings is not possible at this point in time. However, our teams plan to work together to prospectively evaluate this topic area and develop standard operating procedures though mechanisms such as the Molecular and Cellular Characterization of Screen-Detected Lesions (MCL) U01 consortium, supported by NCI's Divisions of Cancer Prevention and Cancer Biology.

In the current study, when the 14 textural and non-textural features were combined via PCA to generate a feature PC1 score that explained 61% of the variability in the data, the radiomic features had a diagnostic accuracy for predicting malignant pathology that was higher than standard worrisome radiologic features or demographic and clinical data elements, especially when combined with the blood-based MGC (Table 13). Indeed, blood-based biomarkers have potential to reduce the false positive and overdiagnosis rates of CT scans [44]. To date, no blood-based biomarker has proven useful in clinical practice for the early detection of PC [45]. miRNAs represent ideal candidates for overcoming limitations of single blood-based biomarkers because they can reflect physiological and pathological conditions and act as extracellular messengers of biological signals derived from the cross talk between the tumor and its microenvironment [46]. We performed cross-validation analyses which indicated robustness of the model using the combination of a MGC with radiomic features from preoperative CT scans. The results suggest these data types may significantly improve the ability to noninvasively risk stratify IPMNs for resection or surveillance. Additionally, external validation in an independent data set is warranted; plans are underway to do this as part of a multi-center prospective study since MGC data is not available for additional retrospective cohort participants.

We recognize that the retrospective design of the current investigation is vulnerable to selection bias since the main inclusion criteria was having a pathologic diagnosis obtained through surgical resection. However, a key advantage of this retrospective series is the ability to integrate several important data types in a relatively large sample size compared to other recent radiomic studies. Another challenge is that CT imaging protocols and scanners, acquisition procedures, slice selection and thickness, and reconstruction parameters may change over time and be coupled with confounding factors stemming from imaging variability and heterogeneity within and between patient cohorts. We acknowledge that inconsistencies and heterogeneity in scans derived from standard diagnostic procedures may play a role in the derived inference and that improvements in diagnostic performance attributed to radiomic features may be minimal in this small dataset. Furthermore, specific to IPMNs, it may be necessary to separate segmentation of nodular and cystic components in future investigations. In our experience, only a subset of IPMN cases had a separate soft tissue component that could be clearly delineated from cystic components; this is an area we plan to evaluate further in the future. Nevertheless, we expect the contribution of radiomic features in the prediction models will be greater once CT acquisition procedures are harmonized. In previous analyses of lung lesions and other cancers [21,27], we evaluated reproducibility of CT-based image features subjected to typical patient level variability; known stable features were used to show the translational potential for multi-institutional application of radiomics [27]. To ensure robust decision support for patients with IPMNs, a radiomics-based classifier will require inclusion of informative, non-redundant features that have high reducibility and stability and are scanner independent. Moreover, engineers and domain expertise are needed to validate models across platforms, potentially using deep learning approaches such as neural net pathway analyses. Furthermore, as part of the National Cancer Institute (NCI) Quantitative Imaging Network (QIN) (imaging.cancer.gov/informatics/qin), we plan to work with other leaders in the field to assess variability of radiomic metrics across institutions due to system and reader inputs (segmentation, seeding, etc.).

In summary, this proof of concept study represents the first we are aware of to integrate clinical factors, radiomic features, and blood-based miRNA expression data [14] into a statistical model that could potentially provide a robust and noninvasive predictor of malignant IPMN pathology. Our preliminary data and that of Hanania et al. (submitted, Oncotarget) suggest a radiomic CT approach could have a previously unappreciated impact, value, and practicality in capturing readily available information not currently analyzed in CT imaging studies to aid in managing pancreatic cysts, a goal in line with QIN initiatives. Larger studies are needed to prospectively explore the diagnostic performance of textural and non-textural radiomic CT features (and possibly features extracted from other modalities such as MRIs or PET/CTs) and the blood-based miRNA classifier as noninvasive predictors of malignant IPMN pathology. If proven useful, such a multimodal approach may lead to a reduction in pancreatic resections and missed opportunities for cures.

TABLE 11

Characteristics of IPMN patients with pre-operative CTs and miRNA data (N = 38).

| Variable | Benign IPMNs[1] (n = 20) | Malignant IPMNs[2] (n = 18) | P-value |
|---|---|---|---|
| Age at diagnosis, mean (SD)(yrs) | 68.0 (10.4) | 70.9 (11.7) | 0.422 |
| Gender | | | |
| Male | 5 (25) | 8 (44) | 0.096 |
| Female | 15 (75) | 10 (56) | |
| Race | | | |
| White, Non-Hispanic | 20 (100) | 16 (89) | 0.218 |
| Black | 0 (0) | 2 (11) | |
| Pre-operative serum CA 19-9 levels, mean (SD)(ng/mL) | 165 (330) | 88.9 (305) | 0.300 |
| Pre-operative serum albumin levels, mean (SD)(ng/mL) | 4.4 (1.0) | 3.9 (0.6) | 0.012 |
| Predominant tumor location | | | |
| Pancreatic Head | 5 (25) | 8 (13) | 0.023 |
| Pancreatic Body or Tail | 15 (75) | 5 (53) | |
| Diffuse | 0 (0) | 2 (13) | |
| Type of ductal communication | | | |
| Main duct or mixed | 4 (20) | 13 (72) | 0.003 |
| Branch duct | 16 (80) | 5 (28) | |
| Main duct (MD)dilatation | | | |
| Diffuse | 1 (5) | 8 (50) | <0.001 |
| Segmental | 3 (15) | 5 (31) | |
| None | 16 (80) | 3 (19) | |
| Size of largest cyst, mean (range) (cm) | 2.8 (1.1-6.6) | 3.9 (1.6-5.4) | 0.018 |
| Solid component or mural nodule | | | |
| Yes | 3 (15) | 9 (50) | 0.035 |
| No | 17 (85) | 9 (50) | |
| High risk stigmata[3] | | | |
| Yes | 3 (15) | 15 (83) | <0.001 |
| No | 17 (85) | 3 (17) | |
| Worrisome features[4] | | | |
| Yes | 13 (65) | 13 (72) | 0.734 |
| No | 7 (35) | 5 (28) | |
| 5 miRNA genomic classifier, mean (SD) | 0.7 | −0.7 | <0.001 |

Data represent counts (percentages) unless otherwise indicated. Counts may not add up to the total due to missing values, and percentages may not equal 100 due to rounding.
[1]Benign IPMNs are represented by 4 low-grade and 16 moderate-grade IPMNs.
[2]Malignant IPMNs are represented by 11 high-grade and 7 invasive IPMNs.
[3]High risk stigmata = MD involvement/dilatation ≥ 10 mm, obstructive jaundice in cyst in pancreatic head, or an enhanced solid component within the cyst.
[4]Worrisome features = MD dilation 5-9 mm, cyst size ≥ 3 cm, thickened enhanced cyst walls, non-enhanced mural nodules, or acute pancreatitis.

TABLE 12

Pre-operative radiomic CT features associated with IPMN pathology.

| Radiomic Feature | Category | Odds Ratio | Lower 95% CI | Upper 95% CI | AUC (95% CI) | P-value |
|---|---|---|---|---|---|---|
| Fourier Descriptor Layer 1 | Texture | 0.42 | 0.18 | 0.97 | 0.69 (0.51-0.87) | 0.043 |
| Histogram Energy Layer 1 | Texture: Histogram | 0.18 | 0.05 | 0.73 | 0.79 (0.64-0.94) | 0.017 |
| Histogram Entropy Layer 1 | Texture: Histogram | 3.77 | 1.34 | 10.6 | 0.77 (0.62-0.93) | 0.012 |
| Co-occurrence matrix features OF1 G1 CONTRAST Layer 1 | Texture: Co-occurrence/ Run-length | 8.08 | 1.40 | 46.7 | 0.79 (0.64-0.94) | 0.020 |
| Run-length features G0 D0 HGRE Layer 1 | Texture: Co-occurrence/ Run-length | 4.30 | 1.37 | 13.5 | 0.79 (0.63-0.95) | 0.013 |
| Run-length features G1 D0 LGRE Layer 1 | Texture: Co-occurrence/ Run-length | 0.11 | 0.01 | 0.88 | 0.79 (0.64-0.94) | 0.038 |
| Laws features E5 E5 Energy Layer 1 | Texture: Laws | 0.06 | 0.01 | 0.65 | 0.74 (0.58-0.91) | 0.020 |
| Laws features L5 S5 Energy Layer 1 | Texture: Laws | 0.21 | 0.05 | 0.91 | 0.73 (0.56-0.89) | 0.037 |
| Laws features R5 E5 Energy Layer 1 | Texture: Laws | 0.20 | 0.05 | 0.91 | 0.71 (0.53-0.89) | 0.038 |
| Wavelet decomposition. P1 L3 C1 Layer 1 | Texture: Wavelet | 2.80 | 1.07 | 7.34 | 0.74 (0.57-0.91) | 0.036 |
| Wavelet decomposition. P1 L3 C2 Layer 1 | Texture: Wavelet | 2.69 | 1.02 | 7.12 | 0.75 (0.59-0.92) | 0.046 |
| Border length (Pxl) | Non-texture: Size & Shape | 2.61 | 1.08 | 6.31 | 0.74 (0.57-0.92) | 0.033 |
| Width (Pxl) | Non-texture: Size & Shape | 2.76 | 1.20 | 6.32 | 0.77 (0.61-0.93) | 0.017 |
| Radius of largest enclosed ellipse | Non-texture: Size & Shape | 0.44 | 0.19 | 0.99 | 0.78 (0.61-0.94) | 0.048 |

TABLE 13

Diagnostic performance of preliminary models to predict malignant IPMN pathology in the study cohort.

| Model[a] | Variables included | AUC (95% CI) | Sensitivity | Specificity | Positive Predictive value | Negative Predictive value |
|---|---|---|---|---|---|---|
| Demographic and clinical data | Age at diagnosis, gender, presence of symptoms | 0.73 (0.56-0.89) | 0.83 | 0.55 | 0.63 | 0.79 |
| Standard imaging data | High risk stigmata | 0.84 (0.72-0.96) | 0.83 | 0.85 | 0.83 | 0.85 |
| Genomic data | 5-miRNA genomic classifier (MGC) | 0.83 (0.69-0.97) | 0.78 | 0.80 | 0.78 | 0.80 |
| Standard imaging + genomic data | High risk stigmata, MGC | 0.95 (0.88-1.00) | 0.94 | 0.90 | 0.89 | 0.95 |
| Standard imaging data | Worrisome features | 0.54 (0.38-0.69) | 0.72 | 0.35 | 0.50 | 0.58 |
| Standard imaging + genomic data | Worrisome features, MGC | 0.83 (0.69-0.97) | 0.83 | 0.80 | 0.79 | 0.84 |
| Radiomic data | Radiomic PC1 classifier | 0.77 (0.61-0.93) | 0.83 | 0.74 | 0.75 | 0.82 |
| Radiomic + genomic data | Radiomic PC1 classifier + MGC | 0.92 (0.83-1.00) | 0.83 | 0.89 | 0.88 | 0.85 |
| Standard imaging + radiomic + genomic data | Worrisome features, Radiomic PC1 classifier + MGC | 0.93 (0.85-1.00) | 0.89 | 0.89 | 0.89 | 0.89 |

[a]Full models include 20 benign and 18 malignant IPMNs.

TABLE 14

CT scanner parameters.

| Manufacturer | Model | Count | Convolutional Kernel | Tube Current (ma) | Software | Institutions |
|---|---|---|---|---|---|---|
| Seimens | Sensation 16 (22) | 34 | B30f (15) | 188-401 | Syngo-CT2006G (11), VA70C (6), VB10B(5) | Moffitt Cancer Center (32), Consortium Centers (2) |
|  | Sensation 40 (6) |  | B31f (15) | 153-520 | Syngo-CT2007S |  |
|  | Sensation 64 (3) |  | B31S (3) | 136-169 | Syngo-CT2007S |  |
|  | Volume zoom (3) |  | B40f (1) | 107 | VA47C |  |
| Toshiba | Acquilion | 2 | FC11 (2) | 300 | V1.41ER001 | Consortium Centers (2) |
| GE | Light Speed 16 | 1 | Standard (1) | 340 | LightSpeedApps405I.2_H4.0M5 | Consortium Centers (1) |

TABLE 15

Diagnostic performance of preliminary models to predict malignant IPMN pathology in the study cohort based on 10-fold cross validation.

| Variables | AUC | Accuracy | Sensitivity | Specificity | PPV | NPV |
|---|---|---|---|---|---|---|
| Age at diagnosis, gender, presence of symptoms | 0.6 (0.55-0.64) | 0.57 (0.5-0.66) | 0.6 (0.44-0.72) | 0.54 (0.45-0.65) | 0.54 (0.47-0.62) | 0.6 (0.52-0.69) |
| High risk stigmata | 0.74 (0.72-0.76) | 0.84 (0.84-0.84) | 0.83 (0.83-0.83) | 0.85 (0.85-0.85) | 0.83 (0.83-0.83) | 0.85 (0.85-0.85) |
| MGC | 0.79 (0.75-0.82) | 0.72 (0.68-0.76) | 0.78 (0.78-0.78) | 0.66 (0.6-0.75) | 0.67 (0.64-0.74) | 0.77 (0.75-0.79) |
| High risk stigmata, MGC | 0.87 (0.82-0.89) | 0.85 (0.79-0.89) | 0.88 (0.78-0.94) | 0.81 (0.75-0.9) | 0.81 (0.76-0.89) | 0.89 (0.8-0.94) |
| Worrisome features | 0.38 (0.26-0.47) | 0.47 (0.32-0.53) | 0.66 (0.5-0.72) | 0.29 (0.15-0.35) | 0.46 (0.35-0.5) | 0.49 (0.25-0.58) |
| Worrisome features, MGC | 0.77 (0.72-0.8) | 0.75 (0.71-0.79) | 0.76 (0.67-0.83) | 0.74 (0.65-0.8) | 0.73 (0.67-0.78) | 0.77 (0.71-0.83) |
| Radiomic PC1 | 0.75 (0.73-0.77) | 0.76 (0.76-0.78) | 0.83 (0.83-0.83) | 0.69 (0.68-0.74) | 0.72 (0.71-0.75) | 0.81 (0.81-0.82) |
| Radiomic PC1, MGC | 0.87 (0.84-0.89) | 0.83 (0.78-0.86) | 0.77 (0.67-0.83) | 0.88 (0.79-0.89) | 0.86 (0.78-0.88) | 0.8 (0.74-0.85) |
| Worrisome features, Radiomic PC1, MGC | 0.85 (0.81-0.88) | 0.81 (0.76-0.86) | 0.83 (0.78-0.89) | 0.79 (0.68-0.89) | 0.79 (0.71-0.88) | 0.83 (0.78-0.89) |

REFERENCES

1. American Cancer Society. Cancer Facts and FIGS. 2016. Atlanta: American Cancer Society. 2016.
2. Rahib L, Smith B D, Aizenberg R, Rosenzweig A B, Fleshman J M and Matrisian L M. Projecting cancer incidence and deaths to 2030: the unexpected burden of thyroid, liver, and pancreas cancers in the United States. Cancer Res. 2014; 74(11):2913-2921.
3. Farrell J J. Prevalence, Diagnosis and Management of Pancreatic Cystic Neoplasms: Current Status and Future Directions. Gut and liver. 2015; 9(5):571-589.
4. Hines O J and Reber H A. Pancreatic surgery. Curr Opin Gastroenterol. 2008; 24(5):603-611.
5. Tanaka M, Fernandez-del Castillo C, Adsay V, Chari S, Falconi M, Jang J Y, Kimura W, Levy P, Pitman M B, Schmidt C M, Shimizu M, Wolfgang C L, Yamaguchi K, et al. International consensus guidelines 2012 for the management of IPMN and MCN of the pancreas. Pancreatology. 2012; 12(3):183-197.
6. Panarelli N C, Sela R, Schreiner A M, Crapanzano J P, Klimstra D S, Schnoll-Sussman F, Pochapin M B and Yantiss R K. Commercial molecular panels are of limited utility in the classification of pancreatic cystic lesions. Am J Surg Pathol. 2012; 36(10): 1434-1443.
7. Kim K W, Park S H, Pyo J, Yoon S H, Byun J H, Lee M G, Krajewski K M and Ramaiya N H. Imaging features to distinguish malignant and benign branch-duct type intraductal papillary mucinous neoplasms of the pancreas: a meta-analysis. Ann Surg. 2014; 259(1):72-81.
8. Roch A M, Ceppa E P, DeWitt J M, Al-Haddad M A, House M G, Nakeeb A and Schmidt C M. International Consensus Guidelines parameters for the prediction of malignancy in intraductal papillary mucinous neoplasm are not properly weighted and are not cumulative. HPB:

9. Sahora K, Mino-Kenudson M, Brugge W, Thayer S P, Ferrone C R, Sahani D, Pitman M B, Warshaw A L, Lillemoe K D and Fernandez-del Castillo C F. Branch duct intraductal papillary mucinous neoplasms: does cyst size change the tip of the scale? A critical analysis of the revised international consensus guidelines in a large single-institutional series. Ann Surg. 2013; 258(3):466-475.
10. Fritz S, Klauss M, Bergmann F, Strobel O, Schneider L, Werner J, Hackert T and Buchler M W. Pancreatic main-duct involvement in branch-duct IPMNs: an underestimated risk. Ann Surg. 2014; 260(5):848-855; discussion 855-846.
11. Goh B K, Tan D M, Ho M M, Lim T K, Chung A Y and Ooi L L. Utility of the sendai consensus guidelines for branch-duct intraductal papillary mucinous neoplasms: a systematic review. J Gastrointest Surg. 2014; 18(7):1350-1357.
12. Subramani R, Gangwani L, Nandy S B, Arumugam A, Chattopadhyay M and Lakshmanaswamy R. Emerging roles of microRNAs in pancreatic cancer diagnosis, therapy and prognosis (Review). International journal of oncology. 2015; 47(4):1203-1210.
13. Permuth-Wey J, Chen Y A, Fisher K, McCarthy S, Qu X, Lloyd M C, Kasprzak A, Fournier M, Williams V L, Ghia K M, Yoder S J, Hall L, Georgeades C, et al. A Genome-Wide Investigation of MicroRNA Expression Identifies Biologically-Meaningful MicroRNAs That Distinguish between High-Risk and Low-Risk Intraductal Papillary Mucinous Neoplasms of the Pancreas. PLoS One. 2015; 10(1):e0116869.
14. Permuth-Wey J, Chen D T, Fulp W J, Yoder S J, Zhang Y, Georgeades C, Husain K, Centeno B A, Magliocco A M, Coppola D and Malafa M. Plasma MicroRNAs as Novel Biomarkers for Patients with Intraductal Papillary Mucinous Neoplasms of the Pancreas. Cancer Prev Res (Phila). 2015.
15. Jamshidi N, Diehn M, Bredel M and Kuo M D. Illuminating radiogenomic characteristics of glioblastoma multiforme through integration of MR imaging, messenger RNA expression, and DNA copy number variation. Radiology. 2014; 270(1):1-2.
16. Nicolasjilwan M, Hu Y, Yan C, Meerzaman D, Holder C A, Gutman D, Jain R, Colen R, Rubin D L, Zinn P O, Hwang S N, Raghavan P, Hammoud D A, et al. Addition of MR imaging features and genetic biomarkers strengthens glioblastoma survival prediction in TCGA patients. Journal of neuroradiology Journal de neuroradiologie. 2014.
17. Kumar V, Gu Y, Basu S, Berglund A, Eschrich S A, Schabath M B, Forster K, Aerts H J, Dekker A, Fenstermacher D, Goldgof D B, Hall L O, Lambin P, et al. Radiomics: the process and the challenges. Magnetic resonance imaging. 2012; 30(9):1234-1248.
18. Coroller T P, Grossmann P, Hou Y, Rios Velazquez E, Leijenaar R T, Hermann G, Lambin P, Haibe-Kains B, Mak R H and Aerts H J. CT-based radiomic signature predicts distant metastasis in lung adenocarcinoma. Radiother Oncol. 2015; 114(3):345-350.
19. Grove O, Berglund A E, Schabath M B, Aerts H J, Dekker A, Wang H, Velazquez E R, Lambin P, Gu Y, Balagurunathan Y, Eikman E, Gatenby R A, Eschrich S, et al. Quantitative computed tomographic descriptors associate tumor shape complexity and intratumor heterogeneity with prognosis in lung adenocarcinoma. PLoS One. 2015; 10(3):e0118261.
20. Leijenaar R T, Carvalho S, Velazquez E R, van Elmpt W J, Parmar C, Hoekstra O S, Hoekstra C J, Boellaard R, Dekker A L, Gillies R J, Aerts H J and Lambin P. Stability of FDG-PET Radiomics features: an integrated analysis of test-retest and inter-observer variability. Acta oncologica (Stockholm, Sweden). 2013; 52(7):1391-1397.
21. Balagurunathan Y, Gu Y, Wang H, Kumar V, Grove O, Hawkins S, Kim J, Goldgof D B, Hall L O, Gatenby R A and Gillies R J. Reproducibility and Prognosis of Quantitative Features Extracted from CT Images. Translational oncology. 2014; 7(1):72-87.
22. Balagurunathan Y, Kumar V, Gu Y, Kim J, Wang H, Liu Y, Goldgof D B, Hall L O, Korn R, Zhao B, Schwartz L H, Basu S, Eschrich S, et al. Test-retest reproducibility analysis of lung CT image features. Journal of digital imaging. 2014; 27(6):805-823.
23. Gatenby R A, Grove O and Gillies R J. Quantitative imaging in cancer evolution and ecology. Radiology. 2013; 269(1):8-15.
24. Zhou M, Hall L, Goldgof D, Russo R, Balagurunathan Y, Gillies R and Gatenby R. Radiologically defined ecological dynamics and clinical outcomes in glioblastoma multiforme: preliminary results. Translational oncology. 2014; 7(1):5-13.
25. Sahani D V, Sainani N I, Blake M A, Crippa S, Mino-Kenudson M and del-Castillo C F. Prospective evaluation of reader performance on MDCT in characterization of cystic pancreatic lesions and prediction of cyst biologic aggressiveness. AJR Am J Roentgenol. 2011; 197(1):W53-61.
26. Lee H J, Kim M J, Choi J Y, Hong H S and Kim K A. Relative accuracy of CT and MRI in the differentiation of benign from malignant pancreatic cystic lesions. Clin Radiol. 2011; 66(4):315-321.
27. Aerts H J, Velazquez E R, Leijenaar R T, Parmar C, Grossmann P, Carvalho S, Bussink J, Monshouwer R, Haibe-Kains B, Rietveld D, Hoebers F, Rietbergen M M, Leemans C R, et al. Decoding tumour phenotype by noninvasive imaging using a quantitative radiomics approach. Nature communications. 2014; 5:4006.
28. Smith A D, Gray M R, Del Campo S M, Shlapak D, Ganeshan B, Zhang X and Carson W E, 3rd. Predicting Overall Survival in Patients With Metastatic Melanoma on Antiangiogenic Therapy and RECIST Stable Disease on Initial Posttherapy Images Using CT Texture Analysis. AJR Am J Roentgenol. 2015; 205(3):W283-293.
29. Skogen K, Ganeshan B, Good C, Critchley G and Miles K. Measurements of heterogeneity in gliomas on computed tomography relationship to tumour grade. Journal of neuro-oncology. 2013; 111(2):213-219.
30. Ganeshan B, Goh V, Mandeville H C, Ng Q S, Hoskin P J and Miles K A. Non-small cell lung cancer: histopathologic correlates for texture parameters at CT. Radiology. 2013; 266(1):326-336.
31. Ganeshan B, Panayiotou E, Burnand K, Dizdarevic S and Miles K. Tumour heterogeneity in non-small cell lung carcinoma assessed by CT texture analysis: a potential marker of survival. European radiology. 2012; 22(4):796-802.
32. Ganeshan B, Skogen K, Pressney I, Coutroubis D and Miles K. Tumour heterogeneity in oesophageal cancer assessed by CT texture analysis: preliminary evidence of an association with tumour metabolism, stage, and survival. Clin Radiol. 2012; 67(2):157-164.

33. Segal E, Sirlin C B, Ooi C, Adler A S, Gollub J, Chen X, Chan B K, Matcuk G R, Barry C T, Chang H Y and Kuo M D. Decoding global gene expression programs in liver cancer by noninvasive imaging. Nat Biotechnol. 2007; 25(6):675-680.
34. Kuo M D, Gollub J, Sirlin C B, Ooi C and Chen X. Radiogenomic analysis to identify imaging phenotypes associated with drug response gene expression programs in hepatocellular carcinoma. J Vasc Interv Radiol. 2007; 18(7):821-831.
35. Nair V S, Gevaert O, Davidzon G, Napel S, Graves E E, Hoang C D, Shrager J B, Quon A, Rubin D L and Plevritis S K. Prognostic PET 18F-FDG uptake imaging features are associated with major oncogenomic alterations in patients with resected non-small cell lung cancer. Cancer Res. 2012; 72(15):3725-3734.
36. Gevaert O, Xu J, Hoang C D, Leung A N, Xu Y, Quon A, Rubin D L, Napel S and Plevritis S K. Non-small cell lung cancer: identifying prognostic imaging biomarkers by leveraging public gene expression microarray data—methods and preliminary results. Radiology. 2012; 264(2):387-396.
37. Diehn M, Nardini C, Wang D S, McGovern S, Jayaraman M, Liang Y, Aldape K, Cha S and Kuo M D. Identification of noninvasive imaging surrogates for brain tumor gene-expression modules. Proc Natl Acad Sci USA. 2008; 105(13):5213-5218.
38. Yamamoto S, Maki D D, Korn R L and Kuo M D. Radiogenomic analysis of breast cancer using MRI: a preliminary study to define the landscape. AJR Am J Roentgenol. 2012; 199(3):654-663.
39. Li W B, Chen H Y, Zhang W, Yan W, Shi R, Li S W and Jiang T. Relationship between magnetic resonance imaging features and miRNA gene expression in patients with glioblastoma multiforme. Chin Med J (Engl). 2013; 126(15):2881-2885.
40. Sozzi G, Boeri M, Rossi M, Verri C, Suatoni P, Bravi F, Roz L, Conte D, Grassi M, Sverzellati N, Marchiano A, Negri E, La Vecchia C, et al. Clinical utility of a plasma-based miRNA signature classifier within computed tomography lung cancer screening: a correlative MILD trial study. Journal of clinical oncology: official journal of the American Society of Clinical Oncology. 2014; 32(8): 768-773.
41. Pecot C V, Li M, Zhang X J, Rajanbabu R, Calitri C, Bungum A, Jett J R, Putnam J B, Callaway-Lane C, Deppen S, Grogan E L, Carbone D P, Worrell J A, et al. Added value of a serum proteomic signature in the diagnostic evaluation of lung nodules. Cancer epidemiology, biomarkers & prevention: a publication of the American Association for Cancer Research, cosponsored by the American Society of Preventive Oncology. 2012; 21(5):786-792.
42. Gu Y, Kumar V, Hall L O, Goldgof D B, Li C Y, Korn R, Bendtsen C, Velazquez E R, Dekker A, Aerts H, Lambin P, Li X, Tian J, et al. Automated Delineation of Lung Tumors from CT Images Using a Single Click Ensemble Segmentation Approach. Pattern Recognit. 2013; 46(3):692-702.
43. Wang H, Schabath M B, Liu Y, Berglund A E, Bloom G C, Kim J, Stringfield O, Eikman E A, Klippenstein D L, Heine J J, Eschrich S A, Ye Z and Gillies R J. Semiquantitative Computed Tomography Characteristics for Lung Adenocarcinoma and Their Association With Lung Cancer Survival. Clinical lung cancer. 2015.
44. Boeri M, Verri C, Conte D, Roz L, Modena P, Facchinetti F, Calabro E, Croce C M, Pastorino U and Sozzi G. MicroRNA signatures in tissues and plasma predict development and prognosis of computed tomography detected lung cancer. Proc Natl Acad Sci USA. 2011; 108(9):3713-3718.
45. Goggins M. Markers of pancreatic cancer: working toward early detection. Clin Cancer Res. 2011; 17(4):635-637.
46. Challagundla K B, Fanini F, Vannini I, Wise P, Murtadha M, Malinconico L, Cimmino A and Fabbri M. microRNAs in the tumor microenvironment: solving the riddle for a better diagnostics. Expert review of molecular diagnostics. 2014; 14(5):565-574.
47. Fenstermacher D A, Wenham R M, Rollison D E and Dalton W S. Implementing personalized medicine in a cancer center. Cancer J. 2011; 17(6):528-536.
48. Adsay N V F T, Hruban R H, Klimstra D S, Kloppel G, et al, Intraductal Papillary Mucinous Neoplasm of the Pancreas. In: Bosman F T, Carneiro F, Hruban R H, Theise N D, editors. WHO classification of tumors of the digestive system. Lyon: WHO Press; 2010. p.304-313.
49. Šimundic' A-M. Measures of diagnostic accuracy: basic definitions. (http://www.ifcc.org/ifccfiles/docs/190404200805.pdf)
50. DeLong E R, DeLong D M and Clarke-Pearson D L. Comparing the areas under two or more correlated receiver operating characteristic curves: a nonparametric approach. Biometrics. 1988; 44(3):837-845.

Sequences

TABLE 16

| Gene Name | Accession No. | Target region | Probe NSID | Isoform hits by probe |
|---|---|---|---|---|
| GKN2 | NM_182536.2 | 461-560 | NM_182536.2:460 | NM_182536 |
| CD19 | NM_001178098.1 | 815-914 | NM_001178098.1:814 | NM_001178098; XM_006721103; NM_001770; XR_950871 |
| BRCA1 | NM_007305.2 | 1276-1375 | NM_007305.2:1275 | NM_007305; NM_007300; NM_007297; NM_007299; NM_007294; NM_007298; NR_027676 |
| HRAS | NM_005343.2 | 397-496 | NM_005343.2:396 | NM_005343; NM_176795; XR_430702; |

TABLE 16-continued

| Gene Name | Accession No. | Target region | Probe NSID | Isoform hits by probe |
|---|---|---|---|---|
| CXCL17 | NM_198477.1 | 441-540 | NM_198477.1:440 | XR_242795; NM_001130442 NM_198477 |
| ESR1 | NM_000125.2 | 2391-2490 | NM_000125.2:2390 | NM_000125; XM_011535546; XM_006715375; XM_006715374; XM_011535548; XM_011535544; XM_011535549; NM_001291230; NM_001122741; NM_001291241; NM_001122740; XM_011535543; XM_011535545; NM_001122742 |
| FGFR3 | NM_022965.2 | 3171-3270 | NM_022965.2:3170 | NM_022965; XM_006713870; XM_006713873; XM_006713868; XM_006713872; NM_000142; XM_011513422; XM_011513420; XM_006713869; NM_001163213; XM_006713871 |
| GEMIN4 | NM_015721.2 | 1926-2025 | NM_015721.2:1925 | NM_015721; XM_011523910; XM_005256670; XM_011523913; XM_005256667; XM_011523911; XM_011523912; XM_005256668 |
| MSH6 | NM_000179.1 | 3526-3625 | NM_000179.1:3525 | NM_000179; NM_001281492; XM_011532800; XM_005264271; XM_011532798; NM_001281493; XM_011532799; NM_001281494 |
| MYC | NM_002467.3 | 1611-1710 | NM_002467.3:1610 | NM_002467 |
| PPARG | NM_015869.3 | 1036-1135 | NM_015869.3:1035 | NM_015869; NM_138712; XM_011533842; NM_138711; NM_005037; XM_011533841; XM_011533840 |
| WNT1 | NM_005430.2 | 351-450 | NM_005430.2:350 | NM_005430 |

TABLE 17

| Gene Name | Forward primer sequence | Reverse primer sequence |
|---|---|---|
| GKN2 | TCCAGCAAATACACCTGGG (SEQ ID NO: 1) | CAGGAGCCCAGCCTTTG (SEQ ID NO: 2) |
| CD19 | GACGGGTCTGTTGTTGCC (SEQ ID NO: 3) | CAGGACCAGGGCTCTTTG (SEQ ID NO: 4) |
| BRCA1 | GGCCTTTCTGCTGACAAGTT (SEQ ID NO: 5) | TGGCCCAGACTCTTCCAG (SEQ ID NO: 6) |
| HRAS | GCCTGTTGGACATCCTGG (SEQ ID NO: 7) | CTTGTTCCCACCAGCAC (SEQ ID NO: 8) |
| CXCL17 | AGGCACCACAGAAAGCCA (SEQ ID NO: 9) | TGGGAGAGTGAGGTGGGA (SEQ ID NO: 10) |
| ESR1 | GGGAACAGCCAAAGGGAT (SEQ ID NO: 11) | GGCAAAATGTCTACTCTCC AGG (SEQ ID NO: 12) |
| FGFR3 | GGTCTCACCCATGCAAGC (SEQ ID NO: 13) | CGGCGGGATAAACCTTCT (SEQ ID NO: 14) |
| GEMIN4 | TCTCACTGCCTTCCCTGC (SEQ ID NO: 15) | AGCACCTCGTCTGGCTCA (SEQ ID NO: 16) |
| MSH6 | CTGGACCAAATATGGGGG (SEQ ID NO: 17) | CATGCATGAGTATGCTGGC (SEQ ID NO: 18) |
| MYC | AACCGAAAATGCACCAGC (SEQ ID NO: 19) | CTCCTCTGCTTGGACGGA (SEQ ID NO: 20) |

TABLE 17-continued

| Gene Name | Forward primer sequence | Reverse primer sequence |
|---|---|---|
| PPARG | AGTTCAAACACATCACCCCC (SEQ ID NO: 21) | TTCATCAAGGAGGCCAGC (SEQ ID NO: 22) |
| WNT1 | CGTAGCCTCCTCCACGAA (SEQ ID NO: 23) | AGTGGGACAGTTCCAGCG (SEQ ID NO: 24) |

TABLE 18

| LncRNAs | Accession No. | Target region | Probe NSID | Isoform hits by probe |
|---|---|---|---|---|
| GAS5 | NR_002578.2 | 301-400 | NR_002578.2:300 | NR_002578 |
| SRA | NM_001035235.2 | 1696-1795 | NM_001035235.2:1695 | NM_001035235; NR_045587; NM_001253764; NR_045586 |
| ADARB2-AS1 | NR_033387.1 | 479-578 | NR_033387.1:478 | NR_033387 |
| ANRIL | NR_003529.3 | 176-275 | NR_003529.3:175 | NR_003529; NR_047536; NR_047537; NR_047538; NR_047539; NR_047533; NR_047542; NR_120536; NR_047534; NR_047543; NR_047541; NR_047532; NR_047535; NR_047540 |
| GLIS3-AS1 | NR_026663.1 | 485-584 | NR_026663.1:484 | NR_026663 |
| LINC00472 | NR_026807.1 | 1081-1180 | NR_026807.1:1080 | NR_026807; NR_121613; NR_121612; NR_121614 |
| MEG3 | NR_002766.2 | 692-791 | NR_002766.2:691 | NR_002766; NR_046466; NR_033359; NR_033358; NR_003530; NR_046470; NR_033360; NR_046464; NR_003531; NR_046471; NR_046465; NR_046467; NR_046473; NR_046469; NR_046468; NR_046472 |
| PANDA | NR_109836.1 | 394-493 | NR_109836.1:393 | NR_109836 |
| PVT1 | NR_003367.1 | 412-511 | NR_003367.1:411 | NR_003367 |
| UCA1 | NR_015379.2 | 1081-1180 | NR_015379.2:1080 | NR_015379 |

TABLE 19

| LncRNAs | Forward primer sequence | Reverse primer sequence |
|---|---|---|
| GAS5 | CATGGATGACTTGCTTGGG (SEQ ID NO: 25) | GGGTGAGGCAAGACCCTT (SEQ ID NO: 26) |
| SRA | GGAAGGGATCTGCTGGGT (SEQ ID NO: 27) | TCAAGGGTGATACAGTGCAAA (SEQ ID NO: 28) |
| ADARB2-AS1 | ATCTTCCTGCCCCTGACC (SEQ ID NO: 29) | TTGGAGGTGAAAATTGTCTGG (SEQ ID NO: 30) |
| ANRIL | GCTCCCCTCGTCGAAAGT (SEQ ID NO: 31) | GCGTGCAGCGGTTTAGTT (SEQ ID NO: 32) |
| GLIS3-AS1 | GGCCTCCTGGAGTCACAA (SEQ ID NO: 33) | GGCAGTCTTTTCGGGCA (SEQ ID NO: 34) |
| LINC00472 | CCTTGGCTCAGGTGCTGT (SEQ ID NO: 35) | TTTGCAAAAGCTAGATCCCAA (SEQ ID NO: 36) |
| MEG3 | GGGCTTCTGGAATGAGCA (SEQ ID NO: 37) | AGCAAGAGGGGTGGGAAG (SEQ ID NO: 38) |
| PANDA | ACATCCCCCAGCTTGTTG (SEQ ID NO: 39) | TGCAGACAAACCACCCCT (SEQ ID NO: 40) |
| PVT1 | AGGGCCTGATCTTTTGGC (SEQ ID NO: 41) | CAGCCACAGCCTCCCTTA (SEQ ID NO: 42) |

TABLE 19-continued

| LncRNAs | Forward primer sequence | Reverse primer sequence |
|---|---|---|
| UCA1 | CATATGGGGCCAGTTCCA (SEQ ID NO: 43) | TGTGAGTGGCGGTCTGAA (SEQ ID NO: 44) |

TABLE 20

Anti-Cancer Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6 - TG | Nilutamide |
| 6 - Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |

TABLE 20-continued

Anti-Cancer Agents

| | |
|---|---|
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoetin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL - 2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin - 2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |

TABLE 20-continued

Anti-Cancer Agents

| | |
|---|---|
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

---

We claim:

1. A method for detecting microRNAs (miRNA) and long non-coding RNAs (lncRNAs) in human blood and assessing radiomic features, from a human subject having an intraductal papillary mucinous neoplasm (IPMN) comprising:
   detecting a level of each of the following miRNAs in a blood sample from the human subject: miR-200a-3p, miR-1185-5p, miR-33a-5p, miR-574-4p, and miR-663b; wherein said detecting is carried out using a method selected from among hybridization assay, RNA sequencing, or amplification assay;
   detecting a level of each of the following lncRNAs in the blood sample from the human subject: ADARB2-AS1, ANRIL, GLIS3-AS1, LINC00472, MEG3, PANDA, PVT1, and UCA1; and
   extracting quantitative radiomic features from an image of abdominal visceral fat from the human subject; wherein the quantitative radiomic features comprise one or more of the following: Fourier Descriptor Layer 1, Histogram Energy Layer 1, Histogram Entropy Layer 1, Co-occurrence matrix features OF1G1 CONTRAST Layer 1, Run-length features G1 DO HGRE Layer 1, Run-length features G1 DO LGRE Layer 1, Laws features E5 E5 Energy Layer 1, Laws features L5 S5 Energy Layer 1, Laws features R5 E5 Energy Layer 1, Wavelet decomposition P1 L3 C1 Layer 1, Wavelet decomposition P1 L3 C2 Layer 1, Border length (Pxl), Width (Pxl), and Radius of largest enclosed ellipse.

2. The method of claim 1, wherein the blood sample is a sample of whole blood, serum, or plasma.

3. The method of claim 1, wherein the blood sample is plasma.

4. The method of claim 1, wherein said detecting is carried out using a method selected from among microarray hybridization, RNA-Seq, or polymerase chain reaction.

5. The method of claim 1, wherein the image is produced by a computed tomography (CT) scan or magnetic resonance imaging (MRI).

6. The method of claim 1, wherein the quantitative radiomic features comprise each of the following radiomic features: Fourier Descriptor Layer 1, Histogram Energy Layer 1, Histogram Entropy Layer 1, Co-occurrence matrix features OF1G1 CONTRAST Layer 1, Run-length features G1DO HGRE Layer 1, Run-length features G1 DO LGRE Layer 1, Laws features E5E5 Energy Layer 1, Laws features L5S5 Energy Layer 1, Laws features R5E5 Energy Layer 1, Wavelet decomposition P1 L3 C1 Layer 1, Wavelet decomposition P1 L3 C2 Layer 1, Border length (Pxl), Width (Pxl), and Radius of largest enclosed ellipse.

7. The method of claim 1, wherein the image is produced by a computed tomography (CT) scan, and wherein the blood sample is a sample of plasma.

8. A method of classifying an intraductal papillary mucinous neoplasm (IPMN) in a human subject as malignant, the method comprising:
   detecting a level of each of the following miRNAs in a blood sample from the human subject: miR-200a-3p, miR-1185-5p, miR-33a-5p, miR-574-4p, and miR-663b, wherein said detecting is carried out using a method selected from among hybridization assay, RNA sequencing, or amplification assay;
   detecting a level of each of the following lncRNAs in the blood sample from the human subject: ADARB2-AS1, ANRIL, GLIS3-AS1, LINC00472, MEG3, PANDA, PVT1, and UCAI;
   extracting each of the following quantitative radiomic features from an image of abdominal visceral fat from the human subject: Fourier Descriptor Layer 1, Histogram Energy Layer 1, Histogram Entropy Layer 1, Co-occurrence matrix features OF 1 G1 CONTRAST Layer 1, Run-length features G1DO HGRE Layer 1, Run-length features G1 DO LGRE Layer 1, Laws features E5E5 Energy Layer 1, Laws features L5S5 Energy Layer 1, Laws features R5E5 Energy Layer 1, Wavelet decomposition P1 L3 C1 Layer 1, Wavelet decomposition P1 L3 C2 Layer 1, Border length (Pxl), Width (Pxl), and Radius of largest enclosed ellipse;
   classifying the IPMN in the human subject as malignant using a classifier that integrates the level of each of said miRNAs, the level of each of said lncRNAs, and each of said quantitative radiomic features, wherein said classifier has an AUC of 0.90.

9. The method of claim 8, wherein the blood sample is a sample of whole blood, serum, or plasma.

10. The method of claim 8, wherein the blood sample is plasma.

11. The method of claim 8, wherein said detecting is carried out using a method selected from among microarray hybridization, RNA-Seq, or polymerase chain reaction.

12. The method of claim 8, wherein the image is produced by a computed tomography (CT) scan or magnetic resonance imaging (MRI).

13. The method of claim 8, wherein the image is produced by a computed tomography (CT) scan, and wherein the blood sample is a sample of plasma.

14. A method of classifying an intraductal papillary mucinous neoplasm (IPMN) in a human subject as malignant and treating the malignant IPMN, the method comprising:
   detecting a level of each of the following miRNAs in a blood sample from the human subject: miR-200a-3p, miR-1185-5p, miR-33a-5p, miR-574-4p, and miR-663b, wherein said detecting is carried out using a method selected from among hybridization assay, RNA sequencing, or amplification assay;
   detecting a level of each of the following lncRNAs in the blood sample from the human subject: ADARB2-AS1, ANRIL, GLIS3-AS1, LINC00472, MEG3, PANDA, PVT1, and UCAI;
   extracting each of the following quantitative radiomic features from an image of abdominal visceral fat from the human subject: Fourier Descriptor Layer 1, Histogram Energy Layer 1, Histogram Entropy Layer 1, Co-occurrence matrix features OF 1 G1 CONTRAST Layer 1, Run-length features G1DO HGRE Layer 1, Run-length features G1 DO LGRE Layer 1, Laws features E5E5 Energy Layer 1, Laws features L5S5 Energy Layer 1, Laws features R5E5 Energy Layer 1, Wavelet decomposition P1 L3 C1 Layer 1, Wavelet decomposition P1 L3 C2 Layer 1, Border length (Pxl), Width (Pxl), and Radius of largest enclosed ellipse;
   classifying the IPMN in the human subject as malignant using a classifier that integrates the level of each of said miRNAs, the level of each of said lncRNAs, and each of said quantitative radiomic features, wherein said classifier has an AUC of 0.90; and
   treating the malignant IPMN in the human subject with a surgical intervention, radiation therapy, or anti-cancer agent.

15. The method of claim 14, wherein the image is produced by a computed tomography (CT) scan, and wherein the blood sample is a sample of plasma.

* * * * *